(12) United States Patent
Harris et al.

US011738023B2

(10) Patent No.: US 11,738,023 B2
(45) Date of Patent: *Aug. 29, 2023

(54) TREATMENT AND PREVENTION OF SLEEP DISORDERS

(71) Applicant: Purdue Pharma L.P., Stamford, CT (US)

(72) Inventors: Stephen C. Harris, Weston, CT (US); Ram P. Kapil, Princeton Junction, NJ (US); Donald J. Kyle, Yardley, PA (US); Garth Whiteside, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/195,434

(22) Filed: Mar. 8, 2021

(65) Prior Publication Data

US 2021/0330994 A1 Oct. 28, 2021

Related U.S. Application Data

(63) Continuation of application No. 16/318,686, filed as application No. PCT/IB2017/054506 on Jul. 25, 2017, now Pat. No. 10,974,081.

(60) Provisional application No. 62/536,097, filed on Jul. 24, 2017, provisional application No. 62/366,960, filed on Jul. 26, 2016.

(51) Int. Cl.
*A61K 31/498* (2006.01)
*A61P 25/20* (2006.01)
*A61M 21/00* (2006.01)

(52) U.S. Cl.
CPC ............ *A61K 31/498* (2013.01); *A61P 25/20* (2018.01); *A61M 21/00* (2013.01)

(58) Field of Classification Search
CPC ....... A61K 31/498; A61P 25/20; A61M 21/00
USPC ......................................................... 514/396
See application file for complete search history.

(56) References Cited

U.S. PATENT DOCUMENTS

| 7,566,728 B2 | 7/2009 | Teshima et al. |
| 8,476,271 B2 | 7/2013 | Tsuno et al. |
| 9,040,533 B2 | 5/2015 | Marra et al. |
| 2005/0119308 A1 | 6/2005 | Teshima et al. |

FOREIGN PATENT DOCUMENTS

| JP | 2011528707 A | 11/2011 |
| JP | 2019523269 A | 8/2019 |
| WO | 2005028466 A1 | 3/2005 |
| WO | 2006025267 A1 | 3/2006 |
| WO | 2009027820 A2 | 3/2009 |
| WO | 2010010458 A1 | 1/2010 |
| WO | 2014102590 A1 | 7/2014 |
| WO | 2014102592 A2 | 7/2014 |
| WO | WO-2018020418 A1 | 2/2018 |

OTHER PUBLICATIONS

Florin et al., "Autoradiographic localization of [3H]nociceptin binding sites in the rat brain," Brain Research 880 (2000) 11-16.
International Search Report corersponding to International Application No. PCT/IB2017/054506 dated Oct. 18, 2017.
Mollereau et al., "Tissue distribution of the opioid receptor-like (ORL1) receptor," Peptides 21, pp. 907-917 (2000).
Post et al., "Proof-of-Concept Study to Assess the Nociceptin Receptor Antagonist LY2940094 as a New Treatment for Alcohol Dependence," Alcoholism: Clinical and Experimental Research, vol. 40, No. 9 (2016).
Sugino et al., "Role of nociceptin and opioid receptor like 1 on entrainment function in the rat suprachiasmatic nucleus," Neuroscience 137 (2006) 537-544.
Teshima et al., "Nonphotic entrainment of the circadian body temperature rhythm by the selective ORL1 receptor agonist W-212393 in rats," British Journal of Pharmacology, 2005, vol. 146, p. 33-40.
Toll et al., "Nociceptin/Orphanin FQ Receptor Structure, Signaling, Ligands, Functions, and Interactionswith Opioid Systems," Pharmacol Rev 68:419-457(2016).
Woodcock et al., "The Efficacy of a NOP1 Agonist (SCH486757) in Subacute Cough," Lung (2010) 188(Suppl 1): S47-S52.

*Primary Examiner* — Yevgeny Valenrod
(74) *Attorney, Agent, or Firm* — Sterne, Kessler, Goldstein & Fox PLLC

(57) ABSTRACT

The disclosure relates to methods for treating or preventing a sleep disorder by administering a compound of formula (1)(1), or a compound of formula (1A), (1B), (1C), (1D), (1E), or (1F) to an animal in need of such treatment. In certain embodiments, such compounds effectively treat or prevent a sleep disorder in the animal, while producing reduced side effects compared to previously available compounds.

20 Claims, 20 Drawing Sheets (1)

TREATMENT AND PREVENTION OF SLEEP DISORDERS

This application is a continuation of U.S. application Ser. No. 17/195,434, which is a national stage of International application serial no. PCT/IB2017/054506, filed Jul. 25, 2017, which claims the benefit under 35 U.S.C. § 119(e) of U.S. provisional application No. 62/536,097, filed Jul. 24, 2017 and U.S. provisional application No. 62/366,960, filed Jul. 26, 2016, the contents of all of which are incorporated herein by reference.

1. FIELD

The disclosure relates to methods for treating or preventing a sleep disorder by administering a compound of formula (1), (1A), (1B), or (1C) or a pharmaceutically acceptable salt or solvate thereof, or a compound of formula (1D), (1E), or (1F) or a solvate thereof to an animal, e.g., a human, in need of such treatment. In certain embodiments, such compounds effectively treat or prevent a sleep disorder in the animal, while producing fewer or reduced side effects compared to previously available compounds.

2. BACKGROUND

Sleep disorders are widely prevalent world-wide and in the United States. Under one classification scheme, six broad categories of sleep disorders have been identified: (i) insomnia, (ii) hypersomnia, (iii) parasomnia, (iv) circadian rhythm sleep-wake disorders, (v) sleep-related breathing disorders, and (vi) sleep movement disorders. Under another classification scheme, ten broad primary categories of sleep disorders have been identified: (1) insomnia disorder, (2) hypersomnolence disorder, (3) narcolepsy, (4) breathing-related sleep disorders, (5) circadian rhythm sleep-wake disorders, (6) non-rapid eye movement ("NREM") sleep arousal disorders, (7) nightmare disorder, (8) rapid eye movement sleep behavior disorder, (9) restless leg syndrome, and (10) substance/medication-induced sleep disorder. Under either scheme, multiple subcategories are recognized within each of the broad categories.

Insomnia has been defined as the condition, with no obvious cause, of difficulty in falling asleep and/or staying asleep. Insomnia is the most common sleep disorder affecting millions of people as either a primary or comorbid condition. Insomnia has been defined as both a disorder (see, e.g., Espie, "Insomnia: Conceptual Issues in the Development, Persistence and Treatment of Sleep Disorder in Adults," *Ann. Reviews Psychology* 53:215-243 (2002)) and a symptom (see, e.g., Hirshkowitz, "Neuropsychiatric Aspects of Sleep and Sleep Disorders," Chapter 10 (pp. 315-340) in *Essentials of Neuropsychiatry and Clinical Neurosciences*, Yudofsy et al., eds., $4^{th}$ Ed., American Psychiatric Publishing, Arlington, Va. (2004)), and this distinction may affect its conceptualization from both research and clinical perspectives. Whether insomnia is viewed as a disorder or a symptom, however, it nevertheless has a profound effect on the individual and on society. Insomnia disorder results in significant distress and/or functional impairments in those who suffer from the condition, underscoring the need for appropriate treatment.

Estimates of the prevalence of insomnia depend on the criteria used in its definition and, more importantly, the population studied. A general consensus developed from a number of population-based studies drawing from different countries is that approximately 30% of adults report one or more of the symptoms of insomnia: difficulty initiating sleep, difficulty maintaining sleep, waking up too early and, in some cases, nonrestorative or poor quality of sleep. If the diagnostic criteria include perceived daytime impairment or distress as a result of the insomnia, in 2005 the NIH determined the prevalence of insomnia in the U.S. to be approximately 10%. If insomnia persists for at least one month and is not due to another sleep disorder, mental disorder, substance use disorder, or medical condition, the prevalence is approximately 6%.

Alcohol dependence is a very common substance use disorder worldwide. Alcohol use disorder, defined according to Diagnostic and Statistical Manual of Mental Disorders criteria (DSM-5, $5^{th}$ Ed. Amer. Psychiatric Publishing, Arlington, Va. (2013)), including all severity classifications, has a lifetime occurrence of about 29% in the United States (Grant et al., "Epidemiology of DSM-5 Alcohol Use Disorder," *JAMA Psychiatry* 72(8):757-766 (2015)). Additionally, alcohol dependence, classified as a separate condition under the DSM $4^{th}$ Edition (DSM-IV, $4^{th}$ Ed., Amer. Psychiatric Publishing, Arlington, Va. (1994)) has a lifetime occurrence of about 12.5% in the United States (Hasin et al., "Prevalence, correlates, disability, and comorbidity of DSM-IV alcohol abuse and dependence in the United States," *Arch. Gen. Psychiatry* 64:830-842 (2007)).

It is known that sleep disorders are more common among alcoholics than among non-alcoholics (Brower, "Alcohol's Effects on Sleep in Alcoholics," *Alcohol Res. Health* 25(2): 110-125 (2001)). For example, Brower discloses, in the general population in the prior 6 months, insomnia affected 18% of alcoholics but only 10% of non-alcoholics and that rates of insomnia are even higher among patients admitted for alcoholism treatment, ranging from 36% to 72%, depending on sample characteristics, the type of sleep-measuring instrument, the amount of time elapsed since the last drink, and the presence of other disorders. Another reference discloses that 91% of alcoholic participants in a sleep study suffered from a sleep disturbance as measured by the well-accepted Pittsburgh Sleep Quality Index ("PSQI") (Conroy et al., "Perception of Sleep in Recovering Alcohol Dependent Patients with Insomnia: Relationship to Future Drinking," *Alcohol Clin. Exp. Res.* 30(12):1992-1999 (2006)).

Polysomnography ("PSG") is a multiparametric test used for studying sleep and for diagnosing sleep disorders. A polysomnography evaluation involves the comprehensive measurement and recording of biophysiological changes occurring during sleep. This typically involves, during the time in bed, continuous recording (in the form of a polysomnogram) of the brain waves (electroencephalogram or EEG), heart rate and rhythm (electrocardiogram or "ECG"), eye movements (electrooculogram or "EOG"), muscle activity and limb movements (electromyogram or "EMG"), blood oxygen level, breathing pattern and air flow, body position, and snoring and other noises made during sleep. Exclusive of the eyes, EMG typically evaluates chin muscle tone, leg movements, chest wall movement, and upper abdominal wall movement.

Existing drugs are known to moderate sleep via a variety of mechanisms. For example, benzodiazepines (e.g., lorazepam, temazepam, triazolam), barbiturates (e.g., phenobarbital, pentobarbital, secobarbital), and so-called "z-drugs" (e.g., zaleplon, zolpidem, zopiclone) all increase sleep by potentiating the action of GABA via action on the GABAa receptor. The benzodiazepines potentiate GABA by increasing the frequency of chloride channel opening. The barbiturates potentiate GABA by increasing the duration of chloride channel opening. The z-drugs are agonists at the GABAαγ1 subunit. Other existing drugs increase sleep by different mechanisms, for example, ramelteon (ROZEREM) is an agonist for the two high-affinity G protein-coupled receptors, termed $MT_1$ and $MT_2$, in the suprachiasmatic nucleus ("SCN") while other drugs (e.g., suvorexant) are orexin receptor antagonists. Many of these existing drugs are classified as controlled substances under the Controlled Substances Act and thus carry the risk of abuse and addiction. For example, lorazepam, temazepam, triazolam, phenobarbital, zaleplon, zolpidem, zopiclone, and suvorexant are all classified as Schedule IV Controlled Substances pursuant to 21 CFR § 1308.14 while pentobarbital and secobarbital are each classified as Schedule II Controlled Substances, that is, substances that have a high potential for abuse which may lead to severe psychological or physical dependence. Cautionary warnings also pertain to certain of these existing drugs. For example, the March 2017 prescribing information for zolpidem tartrate (AMBIEN) states that persons with a history of addiction to, or abuse of, alcohol are at increased risk for misuse, abuse and addiction to zolpidem; avoid AMBIEN use in patients with severe hepatic impairment; and persons experiencing insomnia are instructed to advise their physician if they have a history of alcohol abuse or addiction and/or have liver or kidney disease. Still other existing drugs or drug-like substances are known to decrease sleep, for example, modafinil, tricyclic antidepressants (e.g., desipramine, protriptyline, trimipramine), selective serotonin reuptake inhibitors (e.g., citalopram, fluoxetine, paroxetine), norepinephrine reuptake inhibitors (e.g., atomoxetine, maprotiline, reboxetine), and stimulants (e.g., amphetamine, caffeine).

Identification of the ORL-1 receptor as distinct from the three long-known major classes of opioid receptors in the central nervous system—mu, kappa, and delta—resulted from experimentation on these opioid receptor classes. The ORL-1 receptor was identified and classified as an opioid receptor based only on amino acid sequence homology, as the ORL-1 receptor did not exhibit overlapping pharmacology with the classic mu opioid receptor. It was initially demonstrated that non-selective ligands having a high affinity for mu, kappa, and delta receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand—nociceptin/orphanin FQ," *Trends Pharmacol. Sci.* 18(8):293-300 (1997). Subsequent research led to the isolation and structure of the endogenous ligand of the ORL-1 receptor (i.e., nociceptin; also known as orphanin FQ or OFQ), a seventeen amino acid peptide structurally similar to members of the opioid peptide family. For a general discussion of ORL-1 receptors, see Cab' et al., "Pharmacology of nociceptin and its receptor: a novel therapeutic target," *Br. J. Pharmacol.* 129:1261-1283 (2000).

U.S. Pat. Nos. 8,476,271 and 9,145,408 disclose compounds having an affinity for the ORL-1 receptor.

U.S. Pat. Nos. 7,566,728 and 8,003,669 purport to disclose ORL-1 receptor agonist compounds useful for treating circadian rhythm sleep disorder.

Teshima et al. ("Nonphotic entrainment of the circadian body temperature rhythm by the selective ORL1 receptor agonist W-212393 in rats," *Brit. J. Pharmacol.* 146:33-40 (2005)) describes that the ORL-1 receptor agonist W-212393 may influence circadian entrainment in rats.

Zaveri ("Nociceptin Opioid Receptor (NOP) as a Therapeutic Target: Progress in Translation from Preclinical Research to Clinical Utility," *J. Med. Chem.* 59(15):7011-7028 (2016)) reviews recent progress towards validating the NOP system as a therapeutic target.

The present disclosure provides certain ORL-1 receptor modulators useful for treating or preventing sleep disorders.

Citation of any reference in Section 2 of this application is not to be construed as an admission that such reference is prior art to the present application.

3. SUMMARY

In one aspect, the disclosure provides methods for treating a sleep disorder in an animal comprising administering a therapeutically effective amount of one or more compounds of formula (1), (1A), (1B), or (1C):

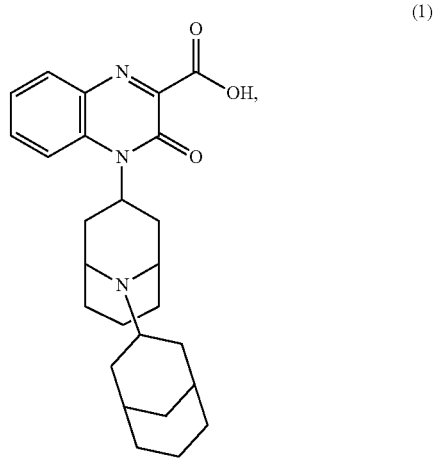 [SMILES: O=C(O)c1nc2ccccc2n(C2CC3CCCC(C2)N3C2CC3CCCC(C3)C2)c1=O]

(1)

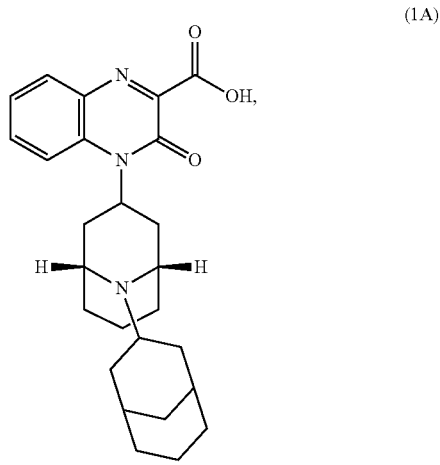 [SMILES: O=C(O)c1nc2ccccc2n([C@H]2C[C@H]3CCC[C@@H](C2)N3C2CC3CCCC(C3)C2)c1=O]

(1A)

(1B)
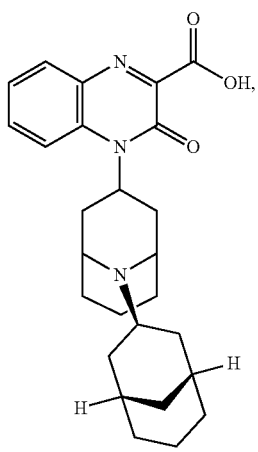

(1C)
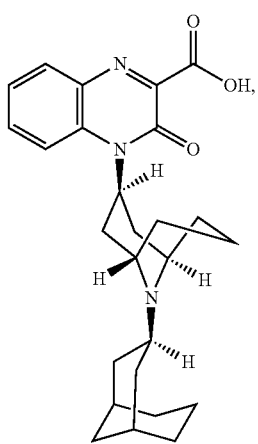

or pharmaceutically acceptable salt or solvate thereof, or compounds of formula (1D), (1E), or (1F):

(1D)
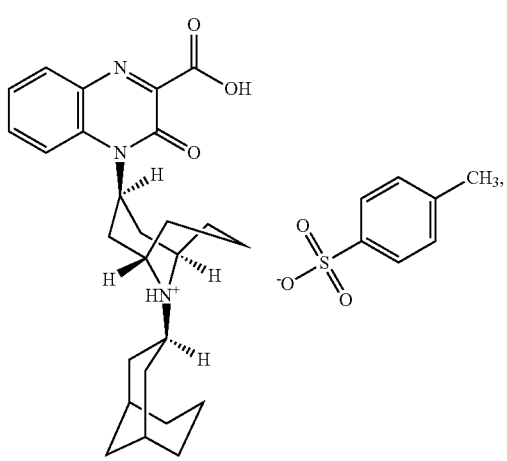

(1E)
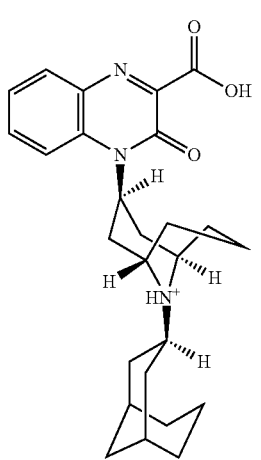

(1F)
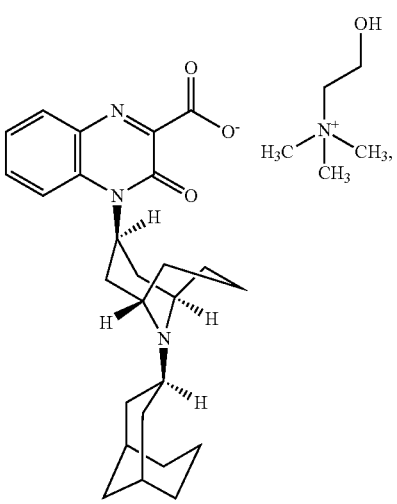

i.e., Compound (1D), Compound (1E), and Compound (1F), respectively, or a solvate thereof, to an animal in need of such treatment. In certain embodiments, such compounds of formula (1), (1A), (1B), or (1C) or a pharmaceutically acceptable salt or solvate thereof, or the compounds of formula (1D), (1E), or (1F) or a solvate thereof, effectively treat a sleep disorder in the animal, while producing fewer or reduced side effects compared to previously available compounds. In certain embodiments, such compounds of formula (1), (1A), (1B), or (1C) or a pharmaceutically acceptable salt or solvate thereof, or the compounds of formula (1D), (1E), or (1F) or a solvate thereof, exhibit affinity for the ORL-1 receptor.

In another embodiment of the disclosure, compositions are disclosed which comprise an effective amount of a compound of formula (1), (1A), (1B), or (1C) or a pharmaceutically acceptable salt or solvate thereof, or a compound of formula (1D), (1E), or (1F) or a solvate thereof, and a pharmaceutically acceptable carrier or excipient. The compositions are useful for treating or preventing a sleep disorder in an animal.

In another embodiment of the disclosure, an effective amount of a compound of formula (1), (1A), (1B), or (1C) or a pharmaceutically acceptable salt or solvate thereof, or a compound of formula (1D), (1E), or (1F) or a solvate thereof, or composition comprising the same, can be used to treat or prevent a sleep disorder including, but not limited to insomnia (e.g., "adult" insomnia, child insomnia, middle-of-the-night insomnia, and short sleeper disorder); hypersomnia (such as insufficient sleep syndrome); circadian rhythm sleep-wake disorder (e.g., delayed sleep-wake phase, advanced sleep-wake phase, irregular sleep-wake rhythm, non-24-hour sleep-wake rhythm, shift work syndrome, and jet lag); an alcohol-induced sleep disorder (e.g., insomnia-type alcohol-induced sleep disorder, daytime sleepiness type alcohol-induced sleep disorder, parasomnia type alcohol-induced sleep disorder, and mixed type alcohol-induced sleep disorder); insomnia in alcohol use disorder; a sleep disturbance associated with alcohol cessation (e.g., insomnia associated with alcohol cessation); or any combination thereof.

In another embodiment of the disclosure, an effective amount of a compound of formula (1), (1A), (1B), or (1C) or a pharmaceutically acceptable salt or solvate thereof, or a compound of formula (1D), (1E), or (1F) or a solvate thereof, or composition comprising the same, can be used to treat or prevent a sleep disorder including, but not limited to insomnia (e.g., "adult" insomnia, child insomnia, middle-of-the-night insomnia, and short sleeper disorder); hypersomnia (such as insufficient sleep syndrome); circadian rhythm sleep-wake disorder (e.g., delayed sleep-wake phase, advanced sleep-wake phase, irregular sleep-wake rhythm, non-24-hour sleep-wake rhythm, shift work syndrome, and jet lag); or any combination thereof.

In another embodiment of the disclosure, an effective amount of a compound of formula (1), (1A), (1B), or (1C) or a pharmaceutically acceptable salt or solvate thereof, or a compound of formula (1D), (1E), or (1F) or a solvate thereof, or composition comprising the same, can be used to treat or prevent a sleep disorder including, but not limited to, an alcohol-induced sleep disorder (e.g., insomnia-type alcohol-induced sleep disorder, daytime sleepiness type alcohol-induced sleep disorder, parasomnia type alcohol-induced sleep disorder, and mixed type alcohol-induced sleep disorder); insomnia in alcohol use disorder; sleep disturbances associated with alcohol cessation (e.g., insomnia associated with alcohol cessation); or any combination thereof.

The disclosure can be understood more fully by reference to the following detailed description and illustrative examples, which are intended to exemplify non-limiting embodiments of the disclosure.

4. BRIEF DESCRIPTION OF THE FIGURES

5. DETAILED DESCRIPTION

Figure 1:
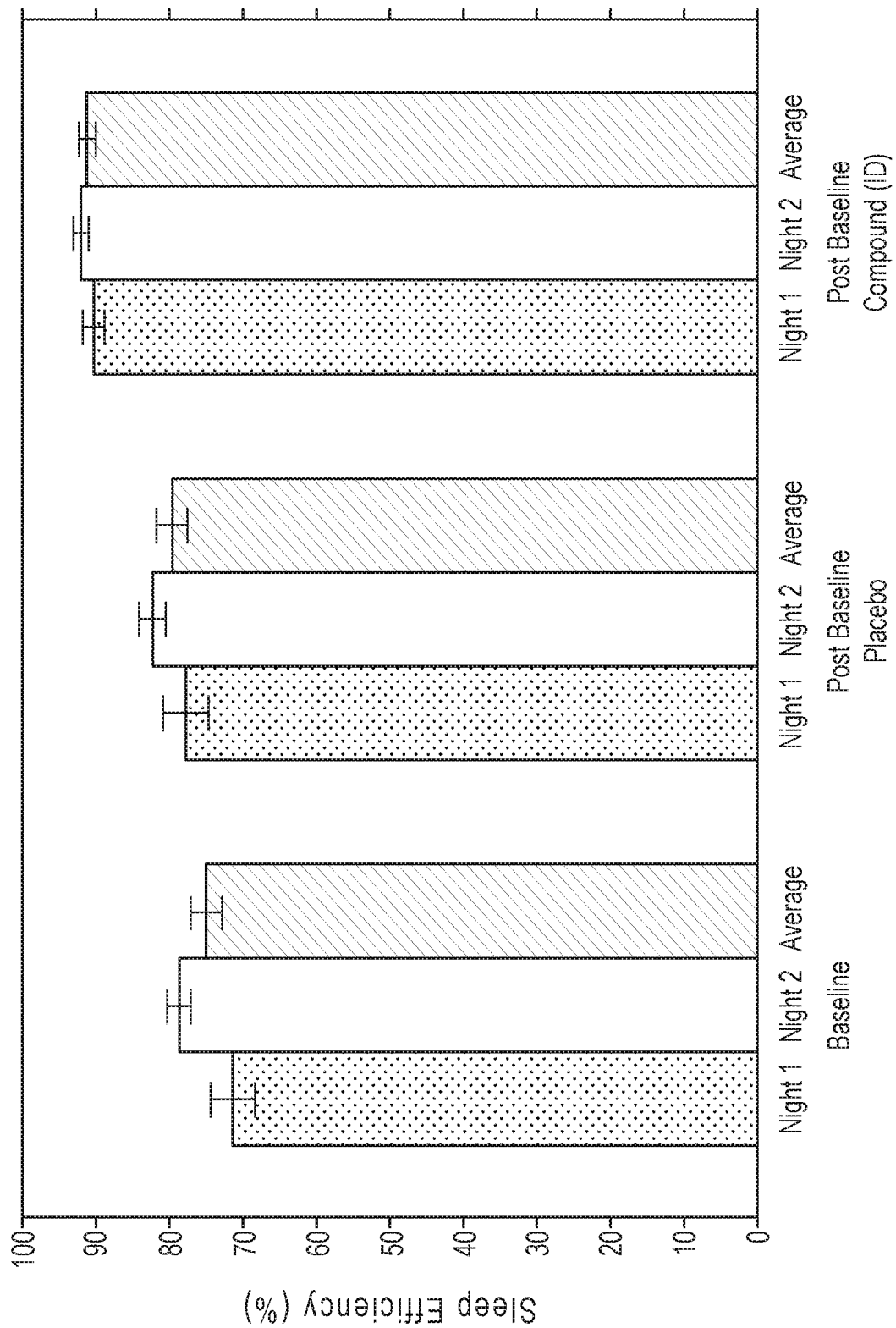
FIG. 1 shows a bar chart summarizing the human Sleep Efficiency ("SE") results in Example 3 for the full analysis population with the standard error bars as indicated.

The invention includes the following:

(1) A method for treating or preventing a sleep disorder, comprising administering to an animal in need thereof a therapeutically effective amount of a compound of Formula (1)

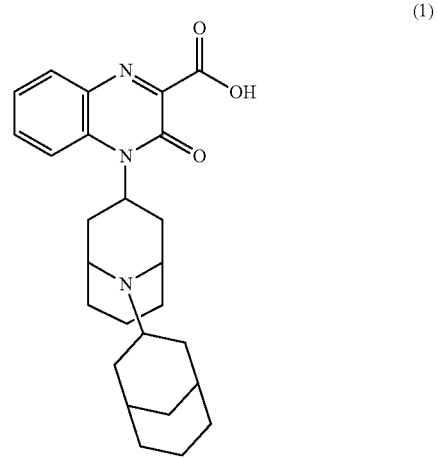

or a pharmaceutically acceptable salt thereof.

(2) The method of the above (1), wherein the compound is a compound of Formula (1A)

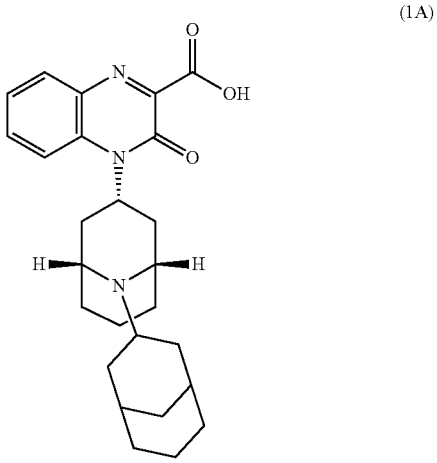

or a pharmaceutically acceptable salt thereof.

(3) The method of the above (1), wherein the compound is a compound of Formula (1B)

(1B)

[Structure of Formula (1B)]

or a pharmaceutically acceptable salt thereof.

(4) The method of any one of the above (1)-(3), wherein the compound is a compound of Formula (1C)

(1C)

[Structure of Formula (1C)]

or a pharmaceutically acceptable salt thereof.

(5) The method of any one of the above (1)-(4), wherein the compound is a compound of Formula (1D)

(1D)

[Structure of Formula (1D)]

(6) The method of any one of the above (1)-(4), wherein the compound is a compound of Formula (1E)

(1E)

[Structure of Formula (1E)]

(7) The method of any one of the above (1)-(4), wherein the compound is a compound of Formula (1F)

(1F)

[Structure of Formula (1F)]

(8) The method of any one of the above (1)-(7), wherein the sleep disorder is an insomnia condition, a hypersomnia condition, a circadian rhythm sleep-wake disorder, an alcohol-induced sleep disorder, or any combination thereof.

(9) The method of the above (8), wherein the alcohol-induced sleep disorder is insomnia-type alcohol-induced sleep disorder, daytime sleepiness type alcohol-induced sleep disorder, parasomnia type alcohol-induced sleep disorder, mixed type alcohol-induced sleep disorder, insomnia in alcohol use disorder, a sleep disorder associated with alcohol cessation, insomnia associated with alcohol cessation, or any combination thereof.

(10) The method of the above (9), wherein the alcohol-induced sleep disorder is treated.

(11) The method of the above (9), wherein the alcohol-induced sleep disorder is prevented.

(12) The method of any one of the above (1)-(8), wherein the sleep disorder is an insomnia condition, a hypersomnia condition, a circadian rhythm sleep-wake disorder, or any combination thereof.

(13) The method of the above (12), wherein the insomnia condition is insomnia, child insomnia, middle-of-the-night insomnia, short sleeper disorder, or any combination thereof.

(14) The method of the above (13), wherein the insomnia condition is treated.

(15) The method of the above (13), wherein the insomnia condition is prevented.

(16) The method of the above (8) or (12), wherein the hypersomnia condition is insufficient sleep syndrome.

(17) The method of the above (16), wherein the hypersomnia condition is treated.

(18) The method of the above (16), wherein the hypersomnia condition is prevented.

(19) The method of the above (8) or (12), wherein the circadian rhythm sleep-wake disorder is delayed sleep-wake phase, advanced sleep-wake phase, irregular sleep-wake rhythm, non-24-hour sleep-wake rhythm, shift work syndrome, jet lag, or any combination thereof.

(20) The method of the above (19), wherein the circadian rhythm sleep-wake disorder is treated.

(21) The method of the above (19), wherein the circadian rhythm sleep-wake disorder is prevented.

(22) The method of any one of the above (1)-(21), wherein sleep efficiency of an animal administered a single daily dose of the compound or a pharmaceutically acceptable salt thereof on two consecutive days is at least about 1.10 times the sleep efficiency of an animal administered a placebo.

(23) The method of any one of the above (1)-(22), wherein latency to persistent sleep of an animal administered a single daily dose of the compound or a pharmaceutically acceptable salt thereof on two consecutive days is at most about 0.65 times the latency to persistent sleep of an animal administered a placebo.

(24) The method of any one of the above (1)-(23), wherein wake after sleep onset (WASO) of an animal administered a single daily dose of the compound or a pharmaceutically acceptable salt thereof on two consecutive days is at most about 0.50 times the WASO of an animal administered a placebo.

(25) The method of any one of the above (1)-(24), wherein administration of the compound or a pharmaceutically acceptable salt thereof is by at least one route selected from oral, parenteral, intravenous, intramuscular, buccal, gingival, sublingual, intraocular, transdermal, and transmucosal.

(26) The method of the above (25), wherein administration of the compound or pharmaceutically acceptable salt thereof is by oral, sublingual, gingival, or buccal administration.

(27) The method of the above (25), wherein administration of the compound or pharmaceutically acceptable salt thereof is by oral or sublingual administration.

(28) The method of any one of the above (1)-(27), wherein the dosage of the compound or pharmaceutically acceptable salt thereof is from about 0.003 mg/kg/day to about 100 mg/kg/day based on the body weight of the animal administered the dosage.

(29) The method of any one of the above (25)-(28), wherein the dosage of the compound or pharmaceutically acceptable salt thereof is from about 0.003 mg/kg/day to about 10 mg/kg/day based on the body weight of the animal administered the dosage.

(30) The method of any one of the above (25)-(29), wherein the dosage of the compound or pharmaceutically acceptable salt thereof is from about 0.003 mg/kg/day to about 5 mg/kg/day based on the body weight of the animal administered the dosage.

(31) The method of any one of the above (25)-(30), wherein the dosage of the compound or pharmaceutically acceptable salt thereof is from about 0.003 mg/kg/day to about 1.0 mg/kg/day based on the body weight of the animal administered the dosage.

(32) The method of any one of the above (25)-(31), wherein the dosage of the compound or pharmaceutically acceptable salt thereof is from about 0.003 mg/kg/day to about 0.15 mg/kg/day.

(33) The method of any one of the above (25)-(32), wherein the dosage of the compound or pharmaceutically acceptable salt thereof is from about 0.010 mg/kg/day to about 1.0 mg/kg/day.

(34) The method of any one of the above (25)-(33), wherein the dosage of the compound or pharmaceutically acceptable salt thereof is from about 0.010 mg/kg/day to about 0.10 mg/kg/day.

(35) The method of any one of the above (1)-(27), wherein the single daily human dose of the compound or pharmaceutically acceptable salt thereof is from about 0.05 mg to about 50 mg.

(36) The method of the above (35), wherein the single daily human dose of the compound or pharmaceutically acceptable salt thereof is from about 0.10 mg to about 15 mg.

(37) The method of the above (35) or (36), wherein the single daily human dose of the compound or pharmaceutically acceptable salt thereof is from about 0.2 mg to about 6.0 mg.

(38) The method of any one of the above (1)-(4) and (8)-(37), wherein the free base of the compound is administered.

(39) The method of any one of the above (1)-(37), wherein a pharmaceutically acceptable salt of the compound is administered.

(40) The method of any one of the above (1)-(6), (8)-(37), and (39), wherein the pharmaceutically acceptable salt is a hydrochloric acid salt, a p-toluenesulfonic acid salt, a sulfate salt, or a phosphoric acid salt.

(41) The method of any one of the above (1)-(5), (8)-(37), (39), and (40), wherein the pharmaceutically acceptable salt is a p-toluenesulfonic acid salt.

(42) The method of the above (41), wherein the pharmaceutically acceptable salt is the mono-tosylate salt.

(43) Use of the compound or a pharmaceutically acceptable salt thereof as defined in any one of the above (1)-(4), (6), (7), and (38)-(42) or the compound as defined in the above (5) in the preparation of a medicament for the treatment or prevention of a sleep disorder.

(44) The use of the above (43), wherein a sleep disorder is treated.

(45) The use of the above (43), wherein a sleep disorder is prevented.

(46) The use of any one of the above (43)-(45), wherein the sleep disorder is an insomnia condition, a hypersomnia condition, a circadian rhythm sleep-wake disorder, an alcohol-induced sleep disorder, or any combination thereof.

(47) The use of the above (46), wherein the sleep disorder is an alcohol-induced sleep disorder which is insomnia-type alcohol-induced sleep disorder, daytime sleepiness type alcohol-induced sleep disorder, parasomnia type alcohol-induced sleep disorder, mixed type alcohol-induced sleep disorder, insomnia in alcohol use disorder, a sleep disorder associated with alcohol cessation, insomnia associated with alcohol cessation, or any combination thereof.

(48) The use of the above (46) or (47), wherein the alcohol-induced sleep disorder is insomnia-type alcohol-induced sleep disorder.

(49) The use of the above (46) or (47), wherein the alcohol-induced sleep disorder is daytime sleepiness type alcohol-induced sleep disorder.

(50) The use of the above (46) or (47), wherein the alcohol-induced sleep disorder is parasomnia type alcohol-induced sleep disorder.

(51) The use of the above (46) or (47), wherein the alcohol-induced sleep disorder is mixed type alcohol-induced sleep disorder.

(52) The use of the above (46) or (47), wherein the alcohol-induced sleep disorder is insomnia in alcohol use disorder.

(53) The use of the above (46) or (47), wherein the alcohol-induced sleep disorder is a sleep disorder associated with alcohol cessation.

(54) The use of the above (46) or (47), wherein the alcohol-induced sleep disorder is insomnia associated with alcohol cessation.

(55) The use of any one of the above (43)-(45), wherein the sleep disorder is an insomnia condition, a hypersomnia condition, a circadian rhythm sleep-wake disorder, or any combination thereof.

(56) The use of the above (55), wherein the sleep disorder is an insomnia condition which is insomnia, child insomnia, middle-of-the-night insomnia, short sleeper disorder, or any combination thereof.

(57) The use of the above (55) or (56), wherein the insomnia condition is insomnia.

(58) The use of the above (55) or (56), wherein the insomnia condition is child insomnia.

(59) The use of the above (55) or (56), wherein the insomnia condition is middle-of-the-night insomnia.

(60) The use of the above (55) or (56), wherein the insomnia condition is short sleeper disorder.

(61) The use of the above (55), wherein the sleep disorder is a hypersomnia condition which is insufficient sleep syndrome.

(62) The use of the above (55), wherein the sleep disorder is a circadian rhythm sleep-wake disorder which is delayed sleep-wake phase, advanced sleep-wake phase, irregular sleep-wake rhythm, non-24-hour sleep-wake rhythm, shift work syndrome, jet lag, or any combination thereof.

(63) The use of the above (55) or (62), wherein the circadian rhythm sleep-wake disorder is delayed sleep-wake phase.

(64) The use of the above (55) or (62), wherein the circadian rhythm sleep-wake disorder is advanced sleep-wake phase.

(65) The use of the above (55) or (62), wherein the circadian rhythm sleep-wake disorder is irregular sleep-wake rhythm.

(66) The use of the above (55) or (62), wherein the circadian rhythm sleep-wake disorder is non-24-hour sleep-wake rhythm.

(67) The use of the above (55) or (62), wherein the circadian rhythm sleep-wake disorder is shift work syndrome.

(68) The use of the above (55) or (62), wherein the circadian rhythm sleep-wake disorder is jet lag.

(69) A pharmaceutical composition for treating or preventing a sleep disorder, comprising the compound or a pharmaceutically acceptable salt thereof as defined in any one of the above (1)-(4), (6), (7), and (38)-(42) or the compound as defined in the above (5).

(70) The pharmaceutical composition of the above (69), wherein the sleep disorder is an insomnia condition, a hypersomnia condition, a circadian rhythm sleep-wake disorder, an alcohol-induced sleep disorder, or any combination thereof.

(71) The pharmaceutical composition of the above (70), wherein the alcohol-induced sleep disorder is insomnia-type alcohol-induced sleep disorder, daytime sleepiness type alcohol-induced sleep disorder, parasomnia type alcohol-induced sleep disorder, mixed type alcohol-induced sleep disorder, insomnia in alcohol use disorder, a sleep disorder associated with alcohol cessation, insomnia associated with alcohol cessation, or any combination thereof.

(72) The pharmaceutical composition of the above (71), wherein the alcohol-induced sleep disorder is treated.

(73) The pharmaceutical composition of the above (71), wherein the alcohol-induced sleep disorder is prevented.

(74) The pharmaceutical composition of the above (69) or (70), wherein the sleep disorder is an insomnia condition, a hypersomnia condition, a circadian rhythm sleep-wake disorder, or any combination thereof.

(75) The pharmaceutical composition of the above (69) or (74), wherein the insomnia condition is insomnia, child insomnia, middle-of-the-night insomnia, short sleeper disorder, or any combination thereof.

(76) The pharmaceutical composition of the above (75), wherein the insomnia condition is treated.

(77) The pharmaceutical composition of the above (75), wherein the insomnia condition is prevented.

(78) The pharmaceutical composition of the above (69) or (74), wherein the hypersomnia condition is insufficient sleep syndrome.

(79) The pharmaceutical composition of the above (78), wherein the hypersomnia condition is treated.

(80) The pharmaceutical composition of the above (78), wherein the hypersomnia condition is prevented.

(81) The pharmaceutical composition of the above (69) or (74), wherein the circadian rhythm sleep-wake disorder is delayed sleep-wake phase, advanced sleep-wake phase, irregular sleep-wake rhythm, non-24-hour sleep-wake rhythm, shift work syndrome, jet lag, or any combination thereof.

(82) The pharmaceutical composition of the above (81), wherein the circadian rhythm sleep-wake disorder is treated.

(83) The pharmaceutical composition of the above (81), wherein the circadian rhythm sleep-wake disorder is prevented.

(84) The pharmaceutical composition of any one of the above (69)-(83), wherein the composition further comprises a pharmaceutically acceptable carrier or excipient.

In one embodiment, a compound of formula (1), (1A), (1B), or (1C) or a pharmaceutically acceptable salt or solvate thereof, or a compound of formula (1D), (1E), or (1F) or a solvate thereof, demonstrates suitable aqueous solubility at a pH of about 6.8. In other embodiments, the aqueous solubility at a pH of about 6.8 of a compound of formula (1), (1A), (1B), or (1C) or a pharmaceutically acceptable salt or solvate thereof, or a compound of formula (1D), (1E), or (1F) or a solvate thereof, is at least about 20 μM, at least about 25 μM, at least about 30 μM, at least about 32 μM, at least about 33 μM, at least about 34 μM, at least about 35 μM, at least about 36 μM, at least about 37 μM, at least about 40 μM, at least about 45 μM, at least about 50 μM, at least about 55 μM, at least about 60 μM, at least about 70 μM, or greater than about 50 μM. In other embodiments, the aqueous solubility at a pH of about 6.8 of a compound of formula (1), (1A), (1B), or (1C) or a pharmaceutically acceptable salt or solvate thereof, or a compound of formula (1D), (1E), or (1F) or a solvate thereof, is from about 20 μM to greater than about 50 µM, from about 25 µM to greater than about 50 µM, from about 30 µM to greater than about 50 µM, from about 32 µM to greater than about 50 µM, from about 33 µM to greater than about 50 µM, from about 34 µM to greater than about 50 µM, from about 35 µM to greater than about 50 µM, from about 36 µM to greater than about 50 µM, from about 37 µM to greater than about 50 µM, from about 40 µM to greater than about 50 µM, from about 20 µM to about 70 µM, from about 25 µM to about 70 µM, from about 30 µM to about 70 µM, from about 32 µM to about 70 µM, from about 33 µM to about 70 µM, from about 34 µM to about 70 µM, from about 35 µM to about 70 µM, from about 36 µM to about 70 µM, from about 37 µM to about 70 µM, or from about 40 µM to about 70 µM. It should be noted that a compound that is insoluble in aqueous solution has an aqueous solubility <0.1 µM. The aqueous solubility values, at a pH of about 6.8, in this paragraph can be determined by the procedure provided in Example 7 herein.

In one embodiment, a compound of formula (1), (1A), (1B), or (1C) or a pharmaceutically acceptable salt or solvate thereof, or a compound of formula (1D), (1E), or (1F) or a solvate thereof, demonstrates suitable rat metabolic stability. In other embodiments, the rat metabolic stability of a compound of formula (1), (1A), (1B), or (1C) or a pharmaceutically acceptable salt or solvate thereof, or a compound of formula (1D), (1E), or (1F) or a solvate thereof, is at least about 60%, at least about 70%, at least about 75%, at least about 80%, at least about 85%, at least about 90%, at least about 91%, at least about 92%, at least about 93%, at least about 94%, or at least about 95%. The rat metabolic stability values in this paragraph can be determined by the in vitro procedure provided in Example 8 herein.

In one embodiment, a compound of formula (1), (1A), (1B), or (1C) or a pharmaceutically acceptable salt or solvate thereof, or a compound of formula (1D), (1E), or (1F) or a solvate thereof, demonstrates suitable human metabolic stability. In other embodiments, the human metabolic stability of a compound of formula (1), (1A), (1B), or (1C) or a pharmaceutically acceptable salt or solvate thereof, or a compound of formula (1D), (1E), or (1F) or a solvate thereof, is at least about 35%, at least about 40%, at least about 45%, at least about 50%, at least about 55%, at least about 60%, at least about 70%, at least about 75%, at least about 80%, at least about 85%, at least about 90%, at least about 91%, at least about 92%, at least about 93%, at least about 94%, or at least about 95%. The human metabolic stability values in this paragraph can be determined by the in vitro procedure provided in Example 8 herein.

In one embodiment, a compound of formula (1), (1A), (1B), or (1C) or a pharmaceutically acceptable salt or solvate thereof, or a compound of formula (1D), (1E), or (1F) or a solvate thereof, demonstrates suitable bioavailability in an animal. In other embodiments, the average bioavailability of a compound of formula (1), (1A), (1B), or (1C) or a pharmaceutically acceptable salt or solvate thereof, or a compound of formula (1D), (1E), or (1F) or a solvate thereof, is at least about 20%, at least about 25%, at least about 30%, at least about 35%, at least about 40%, at least about 45%, at least about 50%, at least about 55%, or at least about 60%. In other embodiments, the average bioavailability of a compound of formula (1), (1A), (1B), or (1C) or a pharmaceutically acceptable salt or solvate thereof, or a compound of formula (1D), (1E), or (1F) or a solvate thereof, is from about 20% to about 60%, from about 25% to about 60%, from about 30% to about 55%, from about 35% to about 50%, from about 35% to about 50%, from about 40% to about 50%, or from about 40% to about 45%. The average bioavailability values in this paragraph can be determined by the procedure provided in Example 9 herein.

In one embodiment, a compound of formula (1), (1A), (1B), or (1C) or a pharmaceutically acceptable salt or solvate thereof, or a compound of formula (1D), (1E), or (1F) or a solvate thereof, demonstrates a suitable fraction unbound. In other embodiments, the fraction unbound of a compound of formula (1), (1A), (1B), or (1C) or a pharmaceutically acceptable salt or solvate thereof, or a compound of formula (1D), (1E), or (1F) or a solvate thereof, is at least about 25%, at least about 30%, at least about 35%, at least about 40%, at least about 45%, at least about 50%, at least about 55%, at least about 60%, at least about 62%, at least about 63%, at least about 64%, at least about 65%, at least about 66%, at least about 67%, at least about 68%, at least about 69%, or at least about 70%. In other embodiments, the fraction unbound of a compound of formula (1), (1A), (1B), or (1C) or a pharmaceutically acceptable salt or solvate thereof, or a compound of formula (1D), (1E), or (1F) or a solvate thereof, is from about 25% to about 90%, from about 25% to about 80%, from about 30% to about 80%, from about 35% to about 80%, from about 40% to about 80%, from about 45% to about 80%, from about 50% to about 80%, from about 55% to about 80%, from about 60% to about 80%, from about 60% to about 75%, from about 62% to about 75%, from about 62% to about 73%, from about 63% to about 72%, or from about 64% to about 72%. The fraction unbound values in this paragraph can be determined by the in vitro procedure provided in Example 10 herein.

In one embodiment, a compound of formula (1), (1A), (1B), or (1C) or a pharmaceutically acceptable salt or solvate thereof, or a compound of formula (1D), (1E), or (1F) or a solvate thereof, demonstrates minimal penetration across the central nervous system ("CNS") blood-brain barrier in an animal Such minimally-penetrating compounds are referred to as "peripherally restricted". In connection with this tissue selectivity, it is useful to define as $K_p$ as the ratio of the quantity of a compound that penetrates across an animal's blood-brain barrier into the CNS (e.g., as determined from the quantity of the compound in a whole brain homogenate) to the quantity of the compound circulating in the animal's plasma.

In other embodiments, the CNS:plasma ratio (or $K_p$) of a peripherally restricted compound of formula (1), (1A), (1B), or (1C) or a pharmaceutically acceptable salt or solvate thereof, or a compound of formula (1D), (1E), or (1F) or a solvate thereof, is about 1:3, about 1:4, about 1:5, about 1:10, about 1:15, about 1:17, about 1:20, about 1:23, about 1:24, about 1:25, about 1:26, about 1:27, about 1:30, about 1:35, about 1:37, about 1:38, about 1:40, about 1:42, about 1:45, about 1:50, about 1:60, about 1:100, about 1:250, about 1:500, about 1:1,000, about 1:5,000, or about 1:10,000. In other embodiments, the CNS:plasma ratio of a peripherally restricted compound of formula (1), (1A), (1B), or (1C) or a pharmaceutically acceptable salt or solvate thereof, or a compound of formula (1D), (1E), or (1F) or a solvate thereof, is from about 1:3 to about 1:250, from about 1:4 to about 1:250, from about 1:5 to about 1:100, from about 1:10 to about 1:50, from about 1:15 to about 1:60, from about 1:20 to about 1:50, from about 1:23 to about 1:45, or from about 1:25 to about 1:40. The CNS:plasma ratio values in this paragraph can be determined by the in vivo procedure provided in Example 11 herein.

A compound of formula (1), (1A), (1B), or (1C) or a pharmaceutically acceptable salt or solvate thereof, or a compound of formula (1D), (1E), or (1F) or a solvate thereof, can be tested for the ability to penetrate into the CNS using in vitro and in vivo methods known in the art such as, e.g., the in vivo method disclosed in Example 11 herein. Certain compounds of formula (1), (1A), (1B), or (1C) or a pharmaceutically acceptable salt or solvate thereof, or compounds of formula (1D), (1E), or (1F) or a solvate thereof, exhibit a reduced propensity to blood-brain barrier penetration as measured by the Madin Darby canine kidney ("MDCK") cell-line transport assay disclosed in, e.g., Wang et al. ("Evaluation of the MDR-MDCK cell line as a permeability screen for the blood-brain barrier," *Int. J. Pharm.* 288(2):349-359 (2005)).

In one embodiment, a compound of formula (1), (1A), (1B), or (1C) or a pharmaceutically acceptable salt or solvate thereof, or a compound of formula (1D), (1E), or (1F) or a solvate thereof, demonstrates suitable rat protein binding. In other embodiments, the rat protein binding of a compound of formula (1), (1A), (1B), or (1C) or a pharmaceutically acceptable salt or solvate thereof, or a compound of formula (1D), (1E), or (1F) or a solvate thereof, is at least about 10%, at least about 15%, at least about 20%, at least about 25%, at least about 30%, at least about 35%, at least about 40%, at least about 42%, at least about 44%, at least about 46%, at least about 47%, at least about 48%, at least about 49%, at least about 50%, at least about 51%, at least about 52%, or at least about 55%. In other embodiments, the rat protein binding of a compound of formula (1), (1A), (1B), or (1C) or a pharmaceutically acceptable salt or solvate thereof, or a compound of formula (1D), (1E), or (1F) or a solvate thereof, is from about 15% to about 75%, from about 20% to about 75%, from about 30% to about 75%, from about 35% to about 70%, from about 35% to about 65%, from about 35% to about 60%, from about 40% to about 60%, from about 42% to about 59%, from about 44% to about 57%, from about 46% to about 55%, from about 48% to about 53%, or from about 49% to about 52%. The rat protein binding values in this paragraph can be determined by the in vitro procedure provided in Example 12 herein.

5.1 Stages of Sleep

Mammalian sleep can be divided into two distinct types: non-rapid eye movement ("NREM") sleep and rapid eye movement ("REM") sleep. NREM sleep is further divided into a series of distinct stages generally referred to as Stages N1 through N3. Stage N1 or light sleep is generally viewed as the transition between being awake and being asleep. Stage N1 is characterized by a slowing in breathing and heart rate during the transition from being awake to being asleep. Stage N2 or true sleep typically follows Stage N1, is considered as baseline sleep, and occupies roughly half of the time asleep. Stage N2 is characterized by muscle relaxation, reduced or limited eye movement, and reduced or limited body movement. Stage N3 is referred to as "delta" or "slow wave" sleep and is generally recognized to be the deepest and most restorative stage of sleep. Stage N3 is characterized by additional slowing of breathing and heart rate. Arousal from Stage N3 can be difficult. For the purposes of FIGS. 5C-18C, for the 24 hour period encompassed in a particular figure the percentage of NREM sleep is calculated as 100×(the number of hours of NREM sleep in that 24 hour period)/24.

REM sleep, sometimes referred to as dream sleep, consists of an active stage of sleep with characteristic rapid eye movements as the sleeper has vivid dreams. REM sleep is recognized as a separate sleep type because of its more distinct reduction of muscle tone and no body movement; however, breathing and heart rate may increase and become irregular during REM sleep. For the purposes of FIGS. 5B-18B, for the 24 hour period encompassed in a particular figure the percentage of REM sleep is calculated as 100×(the number of hours of REM sleep in that 24 hour period)/24.

Each of these sleep types and stages has a telltale EEG pattern and, over a single night of sleep a sleeper will generally cycle through these types and stages a number of times. Each 30 second unit of time over the course of sleep can be referred to as an "epoch" and, based on the EEG pattern obtained during sleep, a sleep technologist is able to assign a sleep type and/or stage (or an awake designation) to each such epoch.

5.2 Sleep Disorders

As noted above, under one classification scheme six broad categories of sleep disorders have been identified: (i) insomnia, (ii) hypersomnia, (iii) parasomnia, (iv) circadian rhythm sleep-wake disorders, (v) sleep-related breathing disorders, and (vi) sleep movement disorders. Multiple subcategories are recognized within each of these broad categories. Each category and subcategory is defined as a "Condition". For example, the Condition insomnia involves the inability to fall asleep or to stay asleep. The Condition insomnia includes insomnia ("adult" insomnia), also sometimes known as sleep-onset insomnia, insomnia disorder, or "primary insomnia" to distinguish it from the Condition insomnia, i.e., the inability of an adult to fall asleep at the desired beginning of sleep; child insomnia, i.e., the inability of a child to stay asleep or to fall asleep, e.g., because of a refusal to go to bed or reluctance to allow a parent to leave the bedside; middle-of-the-night insomnia (or "MOTN insomnia"), also known as sleep maintenance insomnia, middle insomnia, middle-of-the-night awakening (or "MOTN awakening"), and/or nocturnal awakening, i.e., waking up in the middle of the night followed by difficulty in resuming sleep; and short sleeper disorder i.e., adults who feel refreshed and alert after sleeping less than six hours per night. Adult insomnia is also known as early insomnia and can be assessed through the prolongation of LPS. Adult insomnia/early insomnia/insomnia disorder/primary insomnia is not brought about by a disease or the use/abuse of a substance. MOTN insomnia can be assessed through the prolongation of WASO and/or increased number of awakenings ("NAW").

As also noted above, under another classification scheme ten broad primary categories of sleep disorders have been identified: (1) insomnia disorder, (2) hypersomnolence disorder, (3) narcolepsy, (4) breathing-related sleep disorders, (5) circadian rhythm sleep-wake disorders, (6) non-REM sleep arousal disorders, (7) nightmare disorder, (8) REM sleep behavior disorder, (9) restless leg syndrome, and (10) substance/medication-induced sleep disorder. Multiple subcategories are recognized within each of these broad categories. Each category and subcategory is also defined as a "Condition". For example, the Condition substance/medication-induced sleep disorder involves a prominent sleep disturbance that is sufficiently severe to warrant independent clinical attention and that is judged to be primarily associated with the pharmacological effects of a substance, e.g., alcohol (i.e., ethyl alcohol). The Condition substance/medication-induced sleep disorder includes insomnia-type substance/medication-induced sleep disorder, daytime sleepiness type substance/medication-induced sleep disorder, parasomnia type substance/medication-induced sleep disorder, and mixed type substance/medication-induced sleep disorder. The mixed type relates to more than one type of these sleep disturbance-related symptoms being present but none predominating Thus, a Condition that can be treated and/or prevented includes alcohol-induced sleep disorder and any/all of its subcategories: insomnia-type alcohol-induced sleep disorder, daytime sleepiness type alcohol-induced sleep disorder, parasomnia type alcohol-induced sleep disorder, and mixed type alcohol-induced sleep disorder. In alcohol-induced sleep disorder, there is evidence of intoxication or withdrawal from the alcohol and the sleep disorder is associated with intoxication, discontinuation, or withdrawal therefrom. Other allied Conditions that can be treated and/or prevented include insomnia in alcohol use disorder, sleep disturbances associated with alcohol cessation, and/or insomnia associated with alcohol cessation.

The Condition hypersomnia, also sometimes known as hypersomnolence disorder, causes excessive sleepiness. People with hypersomnia may lack energy, have difficulty thinking clearly, and/or fall asleep at inconvenient or even dangerous times, such as while working or driving. The Condition hypersomnia includes narcolepsy, i.e., the feeling of overwhelming tiredness with a potential for sudden uncontrollable sleep attacks, which is classified as a primary condition under some schemes; idiopathic hypersomnia, i.e., lifelong daily periods of an irrepressible urge to sleep, e.g., for 12 to 14 hours over a 24 hour period; Kleine-Levin syndrome, i.e., recurrent (more than once a year) two day to five week periods involving excessive sleepiness; insufficient sleep syndrome, i.e., the regular failure to get enough sleep at night resulting in sleep deprivation; and long sleeper disorder i.e., regular sleep of normal and good quality, but much greater in length than others similarly situated (e.g., of similar age).

The Condition parasomnia involves unwanted experiences or events that occur during sleep or while falling asleep, or while waking up. The behaviors may be complex and appear purposeful to others, but the sleeper remains asleep during the event and often has no memory that it has occurred. The Condition parasomnia includes confusional arousal, i.e., acting in a strange confused way upon or just after awakening; sleepwalking, also sometimes known as a non-REM sleep arousal disorder, i.e., arising from bed and walking while still asleep and, if awakening, not knowing how he or she arrived at the site of awakening, which is classified as a primary condition under some schemes; sleep terror, also sometimes known as a non-REM sleep arousal disorder, i.e., waking with intense fear but with little or no memory of a terrifying dream, which is classified as a primary condition under some schemes; sleep eating disorder, i.e., binge eating while only partially awake with little or no memory of the binge; REM sleep behavior disorder, i.e., acting out vivid dreams, e.g., by punching or flailing, while asleep, which is classified as a primary condition under some schemes; sleep paralysis, i.e., being unable to move the body upon falling asleep or awakening; nightmare, also sometimes known as nightmare disorder, i.e., dreams arousing intense feelings of fear, horror and/or distress that may cause fear of going to sleep or difficulty in falling back asleep, which is classified as a primary condition under some schemes; bedwetting, i.e., failure to awaken to eliminate when the bladder is full; sleep hallucination, i.e., imagined events that seem very real, often visual but may also involve other senses; exploding head syndrome, i.e., hearing a loud imaginary noise just before falling asleep or awakening; and sleep talking, i.e., often loud, sometimes nonsensical speaking while asleep.

The Condition circadian rhythm sleep-wake disorder involves sleep times that are out of alignment with the normal day/night cycle and/or the 24 hour clock. The Condition circadian rhythm sleep-wake disorder includes delayed sleep-wake phase, i.e., where a sleep pattern is delayed by two or more hours so sleep occurs later at night and awakening later in the morning; advanced sleep-wake phase, i.e., falling asleep several hours before normal bedtime and, correspondingly, waking up earlier; irregular sleep-wake rhythm, i.e., sleep patterns being so disorganized that there is no clear sleeping-waking schedule; non-24-hour sleep-wake rhythm, i.e., the sleeper's sleep time shifts later each day so that it may become, over time, misaligned with the desired sleep pattern; shift work syndrome, i.e., having a work schedule with periodically variable starting and ending times such that sleep quality is poor and the development of consistent feelings of fatigue or exhaustion; and jet lag, i.e., difficulty in adjusting the sleep schedule after traveling across multiple time zones.

The Condition sleep-related breathing disorder, also sometimes known as breathing-related sleep disorder, involves difficulty in breathing during sleep. The Condition sleep-related breathing disorder includes obstructive sleep apnea, i.e., the stoppage of breathing during sleep because of a blockage in the airways; snoring, i.e., making loud noises during sleep caused by vibration of tissues in the back of the throat; central sleep apnea, i.e., the decrease or stoppage of breathing during sleep caused by a brain or heart problem and not by an obstruction in the airways; child sleep apnea, i.e., the stoppage of breathing during sleep in children because of the large size of the tonsils and adenoids when compared to the throat; infant sleep apnea, i.e., the stoppage of breathing during sleep in infants because of a developmental problem resulting from an immature brainstem or other medical condition; and sleep-related groaning, i.e., making a prolonged noise resembling groaning caused by exhaling during sleep.

The Condition sleep movement disorder involves movement during sleep or prior to sleep. These disorders can cause difficulty in falling asleep, remaining asleep, and/or obtaining restful sleep. The Condition sleep movement disorder includes restless leg syndrome, i.e., burning or itching inside of the legs when lying down that makes getting comfortable and falling asleep difficult, which is classified as a primary condition under some schemes; periodic limb movement syndrome, i.e., a series of uncontrollable, repetitive muscle movements, typically of the lower legs, that disrupt sleep; sleep leg cramp, i.e., sudden and intense feelings of pain in the foot or leg caused by muscle contraction and tightening during sleep; and sleep rhythmic movement syndrome, i.e., repeated body movements such as rocking, head banging or head rolling while asleep or falling asleep.

5.3 ORL-1 Expression

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," TIPS 24(2):87-90 (2003); and Lazareno, "Measurement of Agonist-stimulated [$^{35}$S]GTPγS Binding to Cell Membranes," *Methods in Molecular Biology* 106:231-245 (1999).

It is known that mammalian species display differences in ORL-1 receptor expression. For example, in the nucleus accumbens and caudate putamen, rodents have relatively low levels of ORL-1 receptor expression (Florin et al., "Autoradiographic localization of [$^3$]nociceptin binding sites in the rat brain," *Brain Res.* 880:11-16 (2000); Neal et al., "Opioid receptor-like (ORL1) receptor distribution in the rat central nervous system: Comparison of ORL1 receptor mRNA expression with $^{125}$I-[14Tyr]-orphanin FQ binding," *J. Compar. Neurol.* 412(4):563-605 (1999)). In contrast, monkeys and humans have moderate to high levels of expression in these regions (Bridge et al., "Autoradiographic localization of $^{125}$I[$^{14}$Tyr] nociceptin/orphanin FQ binding sites in Macaque primate CNS," *Neurosci.* 118:513-523 (2003); Berthele et al., "[$^3$H]-Nociceptin ligand-binding and nociception opioid receptor mRNA expression in the human brain," *Neurosci.* 121:629-640 (2003)). In another example, rodents have relatively low levels of ORL-1 receptor expression in the cerebellar cortex, while monkeys and humans have moderate to high levels of expression in these regions. Moreover, rodents have relatively low levels of expression of ORL-1 in lamina I and II of the prefrontal cortex ("PFC"), while humans have moderate to high levels of expression in lamina I and II of the PFC. Thus, references such as those above disclose notable supra-spinal species differences in ORL-1 expression and protein localization, which may be of physiological consequence.

It is well known that one of the nuclei of the brain's hypothalamus, the SCN, is the master controller of the sleep cycle in humans (Richardson, "The Human Circadian System in Normal and Disordered Sleep," *J. Clin. Psychiatry* 66(Suppl. 9):3-9 (2005)). The SCN is made up of a network of nerve cells that fire together with the circadian rhythm. When injected unilaterally into the SCN of Syrian hamsters, nociceptin, the endogenous ligand of the ORL-1 receptor, modulated the activity of SCN neurons and the response of the circadian clock to light (Allen et al., *J. Neurosci.* 19(6):2152-2160 (1999)). An ORL-1 agonist (W-212393) induced a phase advance in the circadian body temperature rhythm of rats by suppression of rhythmic firing of SCN neurons (Teshima et al., *Br. J. Pharmacol.* 146(1):33-40 (2005)). These references demonstrate that modulating the ORL-1 receptor in the brain can influence circadian-related processes such as, e.g., sleep.

It is also recognized that portions of the hypothalamus are only partially protected by the blood-brain-barrier (De la Torre, *J. Neurol. Sci.* 12(1):77-93 (1971)). While not wishing to be bound by theory, it is possible that a compound of formula (1), (1A), (1B), or (1C) or a pharmaceutically acceptable salt or solvate thereof, or a compound of formula (1D), (1E), or (1F) or a solvate thereof is able to gain access to the SCN or other related nuclei in humans, stimulate ORL-1 receptors therein, and produce fatigue and/or somnolence via modulation of the rhythmic firing pattern of the SCN neurons or other related nuclei.

According to the present disclosure, some compounds of formula (1), (1A), (1B), or (1C) or a pharmaceutically acceptable salt or solvate thereof, or of formula (1D), (1E), or (1F) or a solvate thereof are partial agonists at the human ORL-1 receptor. In another embodiment, a compound of formula (1), (1A), (1B), or (1C) or a pharmaceutically acceptable salt or solvate thereof, or a compound of formula (1D), (1E), or (1F) or a solvate thereof is a partial agonist at the human ORL-1 receptor and an antagonist at a human mu, kappa, and/or delta opioid receptor. In another embodiment, a compound of formula (1), (1A), (1B), or (1C) or a pharmaceutically acceptable salt or solvate thereof, or a compound of formula (1D), (1E), or (1F) or a solvate thereof is a partial agonist at the human ORL-1 receptor and an antagonist at the human μ opioid receptor.

5.4 Definitions

As used in connection with the compounds of formula (1), (1A), (1B), (1C) and their pharmaceutically acceptable salts and/or solvates, and the compounds of formula (1D), (1E), (1F) and their solvates, and their methods of use, the terms used herein have the following meanings.

The term "Time in Bed" ("TIB") refers to the duration of time, e.g., in minutes, of an entire intended sleep episode from its beginning to its end. TIB is often of a fixed duration, e.g., 480 minutes.

The term "Total Sleep Time" ("TST") refers to the sum of all time epochs, e.g., in minutes, spent in either NREM (including all of Stages N1 through N3) or REM sleep.

The term "Sleep Efficiency" ("SE") is measured by polysomnography in insomnia subjects and refers to the fraction of the TIB that is spent asleep in REM and NREM sleep and is calculated as the following ratio: TST/TIB. Alternately, SE can be expressed as a percentage by multiplying this ratio by 100. SE is a measure of sleep maintenance throughout the night, thus, assessment of SE also includes, inter alia, assessment of prolonged LPS and/or assessment of prolonged WASO.

The term "Latency to Persistent Sleep" ("LPS") refers to the time, e.g., in minutes, from the beginning of the TIB until the start of a period of least 10 uninterrupted minutes of sleep epochs—in any sleep stage. LPS is a measure of the "speed" of going to sleep.

The term "Total Wake Time" ("TWT") refers, for the TIB, to the total time, e.g., in minutes, of epochs spent awake, i.e., not in any sleep stage.

The term "Wake During Sleep" ("WDS") refers to the total time, e.g., in minutes, of epochs spent awake occurring after the onset of persistent sleep (defined as at least 10 consecutive minutes of sleep epochs of any sleep stage) and before the onset of the final epoch of sleep (of any sleep stage) during the TIB.

The term "Wake After Sleep" ("WAS") refers to the duration, e.g., in minutes, of time spent awake after the conclusion of final sleep epoch (of any sleep stage) until the end of the TIB.

The term "Wake After Sleep Onset" ("WASO") refers to the sum of WDS and WAS. WASO is another measure of sleep maintenance throughout the night.

The term "Number of Awakenings" ("NAW") refers to the number of times after onset of persistent sleep in which an awakening for a period of greater than 30 seconds occurs.

The term "REM latency" refers to the time, e.g., in minutes, from the beginning of the TIB until the beginning of the first epoch of REM sleep.

For the purposes of FIGS. 5A-18A, for the 24 hour period encompassed in a particular figure the percentage of "wakefulness" is calculated as 100×(the number of hours spent awake (i.e., not in either REM sleep or in NREM sleep) in that 24 hour period)/24.

The term "animal" includes, but is not limited to, a human or a non-human mammal, such as a companion animal or livestock, e.g., a cow, monkey, baboon, chimpanzee, horse, sheep, pig, chicken, turkey, quail, cat, dog, mouse, rat, rabbit or guinea pig. In one embodiment, an animal is a human.

The term "pharmaceutically acceptable salt", as used herein, is any pharmaceutically acceptable salt that can be prepared from a compound of formula (1), (1A), (1B), or (1C) or is the pharmaceutically acceptable salt shown herein as formula (1D), (1E), or (1F) including a salt formed from an acid and a basic functional group, such as a nitrogen group, of a compound of formula (1), (1A), (1B), or (1C). Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound of formula (1), (1A), (1B), or (1C) having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines, such as N-methyl-N-ethylamine, diethylamine, triethylamine, tributyl amine, (tert-butylamino)methanol, and tris-(hydroxymethyl)amine; dicyclohexylamine; pyridine; picoline; mono-, bis-, or tris-(2-hydroxy-($C_1$-$C_3$)alkyl amines), such as mono-, bis-, or tris-(2-hydroxyethyl)amine, and N,N-di-[($C_1$-$C_3$)alkyl]-N-(hydroxy-($C_1$-$C_3$)alkyl)-amines, such as N,N-dimethyl-N-(2-hydroxyethyl)amine; N-methyl-D-glucamine; an amino acid, such as arginine and lysine; an amino acid derivative, such as choline (i.e., 2-hydroxy-N,N,N-trimethylethan-1-aminium), a derivative of the amino acid serine; and the like. In one embodiment, the pharmaceutically acceptable salt is a hydrochloride salt, a sulfate salt, a sodium salt, a potassium salt, a benzene sulfonic acid salt, a para-toluenesulfonic acid salt, or a fumaric acid salt. In another embodiment, the pharmaceutically acceptable salt is a hydrochloride salt or a sulfate salt. In another embodiment, the pharmaceutically acceptable salt is a hydrochloride salt. In another embodiment, the pharmaceutically acceptable salt is a sulfate salt. In another embodiment, the pharmaceutically acceptable salt is a sodium salt. In another embodiment, the pharmaceutically acceptable salt is a potassium salt. In another embodiment, the pharmaceutically acceptable salt is a fumaric acid salt. In another embodiment, the pharmaceutically acceptable salt is a para-toluenesulfonic acid salt. In another embodiment, the pharmaceutically acceptable salt is a choline salt.

In another embodiment, the pharmaceutically acceptable para-toluenesulfonic acid salt contains one equivalent of a compound of formula (1), (1A), (1B), or (1C) and about 1.0 equivalent of para-toluenesulfonic acid, e.g., from about 0.8 to about 1.2 equivalents of para-toluenesulfonic acid in one embodiment, from about 0.9 to about 1.1 equivalents of para-toluenesulfonic acid in another embodiment, from about 0.93 to about 1.07 equivalents of para-toluenesulfonic acid in another embodiment, from about 0.95 to about 1.05 equivalents of para-toluenesulfonic acid in another embodiment, from about 0.98 to about 1.02 equivalents of para-toluenesulfonic acid in another embodiment, or from about 0.99 to about 1.01 equivalents of para-toluenesulfonic acid in another embodiment. In another embodiment, the pharmaceutically acceptable para-toluenesulfonic acid salt contains about one equivalent of a compound of formula (1), (1A), (1B), or (1C) and about one equivalent of para-toluenesulfonic acid, i.e., is a mono-tosylate salt. In another embodiment, the pharmaceutically acceptable para-toluenesulfonic acid salt contains one equivalent of a compound of formula (1), (1A), (1B), or (1C) and about one equivalent of para-toluenesulfonic acid. In another embodiment, the pharmaceutically acceptable para-toluenesulfonic acid salt contains one equivalent of a compound of formula (1), (1A), (1B), or (1C) and one equivalent of para-toluenesulfonic acid. The mono-tosylate salt of the compound of formula (1C), i.e., the compound of formula (1D), is as follows:

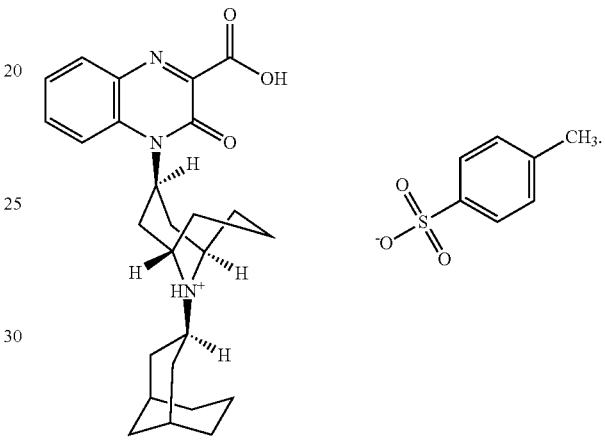

(1D)

In another embodiment, the pharmaceutically acceptable hydrochloride salt contains one equivalent of a compound of formula (1), (1A), (1B), or (1C) and about 1.0 equivalent of hydrochloric acid, e.g., from about 0.8 to about 1.2 equivalents of hydrochloric acid in one embodiment, from about 0.9 to about 1.1 equivalents of hydrochloric acid in another embodiment, from about 0.93 to about 1.07 equivalents of hydrochloric acid in another embodiment, from about 0.95 to about 1.05 equivalents of hydrochloric acid in another embodiment, from about 0.98 to about 1.02 equivalents of hydrochloric acid in another embodiment, or from about 0.99 to about 1.01 equivalents of hydrochloric acid in another embodiment. In another embodiment, the pharmaceutically acceptable hydrochloride salt contains about one equivalent of a compound of formula (1), (1A), (1B), or (1C) and about one equivalent of hydrochloric acid, i.e., is a mono-hydrochloride salt. In another embodiment, the pharmaceutically acceptable hydrochloride salt contains one equivalent of a compound of formula (1), (1A), (1B), or (1C) and about one equivalent of hydrochloric acid. In another embodiment, the pharmaceutically acceptable hydrochloride salt contains one equivalent of a compound of formula (1), (1A), (1B), or (1C) and one equivalent of hydrochloric acid. The mono-hydrochloride salt of the compound of formula (1C) is the compound of formula (1E). One skilled in the art will recognize that acid addition salts of a compound of formula (1), (1A), (1B), or (1C) for use in the methods of the disclosure can be prepared by reaction of each compound with the appropriate acid by a variety of known methods.

In another embodiment, the pharmaceutically acceptable choline salt contains one equivalent of a compound of formula (1), (1A), (1B), or (1C) and about 1.0 equivalent of choline, e.g., from about 0.8 to about 1.2 equivalents of choline in one embodiment, from about 0.9 to about 1.1 equivalents of choline in another embodiment, from about 0.93 to about 1.07 equivalents of choline in another embodiment, from about 0.95 to about 1.05 equivalents of choline in another embodiment, from about 0.98 to about 1.02 equivalents of choline in another embodiment, or from about 0.99 to about 1.01 equivalents of choline in another embodiment. In another embodiment, the pharmaceutically acceptable choline salt contains about one equivalent of a compound of formula (1), (1A), (1B), or (1C) and about one equivalent of choline, i.e., is a mono-choline salt. In another embodiment, the pharmaceutically acceptable choline salt contains one equivalent of a compound of formula (1), (1A), (1B), or (1C) and about one equivalent of choline. In another embodiment, the pharmaceutically acceptable choline salt contains one equivalent of a compound of formula (1), (1A), (1B), or (1C) and one equivalent of choline. The mono-choline salt of the compound of formula (1C) is the compound of formula (1F). One skilled in the art will recognize that base addition salts of a compound of formula (1), (1A), (1B), or (1C) for use in the methods of the disclosure can be prepared by reaction of each compound with the appropriate base by a variety of known methods.

The methods of the disclosure provided herein also encompass the use of any solvate of the compounds of formula (1), (1A), (1B), (1C), (1D), (1E), and (1F). "Solvates" are generally known in the art, and are considered herein to be a combination, physical association and/or solvation of a compound of formula (1), (1A), (1B), or (1C) or a pharmaceutically acceptable salt thereof, or a compound of formula (1D), (1E), or (1F) with a solvent molecule. This physical association can involve varying degrees of ionic and covalent bonding, including hydrogen bonding. When the solvate is of the stoichiometric type, there is a fixed ratio of the solvent molecule to the compound of formula (1), (1A), (1B), or (1C) or a pharmaceutically acceptable salt thereof, or a compound of formula (1D), (1E), or (1F), e.g., a di-solvate, mono-solvate or hemi-solvate when the [solvent molecule]:[compound of formula (1), (1A), (1B), or (1C) or a pharmaceutically acceptable salt thereof, or a compound of formula (1D), (1E), or (1F) molecule] molar ratio is 2:1, 1:1 or 1:2, respectively. In other embodiments, the solvate is of the non-stoichiometric type. For example, the compound of formula (1), (1A), (1B), or (1C) or a pharmaceutically acceptable salt thereof, or the compound of formula (1D), (1E), or (1F) crystal can contain solvent molecules in the structural voids, e.g., channels, of the crystal lattice. In certain instances, the solvate can be isolated, for example, when one or more solvent molecules are incorporated into the crystal lattice of a crystalline solid. Thus, "solvate", as used herein, encompasses both solution-phase and isolatable solvates.

A compound of formula (1), (1A), (1B), or (1C) or a pharmaceutically acceptable salt thereof, or a compound of formula (1D), (1E), or (1F) of the disclosure can be present as a solvated form with a pharmaceutically acceptable solvent, such as water, methanol, ethanol, and the like, and it is intended that the disclosure include both solvated and unsolvated forms of a compound of formula (1), (1A), (1B), and (1C) or a pharmaceutically acceptable salt thereof, and a compound of formula (1D), (1E), and (1F). As "hydrate" relates to a particular subgroup of solvates, i.e., where the solvent molecule is water, hydrates are included within the solvates of the disclosure. In one embodiment, the compound of formula (1), (1A), (1B), or (1C) is present as a monohydrate, e.g., as a free base where the water:[compound of formula (1), (1A), (1B), or (1C) or a pharmaceutically acceptable salt thereof, or compound of formula (1D), (1E), or (1F)] molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Solvates can be made according to known techniques in view of the present disclosure. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3):601-611 (2004), describes the preparation of solvates of fluconazole with ethyl acetate and with water. Similar preparations of solvates, hemi-solvate, hydrates, and the like are described by Van Tonder et al., "Preparation and Physicochemical Characterization of 5 Niclosamide Solvates and 1 Hemisolvate," *AAPS Pharm. Sci. Tech.*, 5(1):Article 12 (2004), and Bingham et al., "Over one hundred solvates of sulfathiazole," *Chem. Comm.*, pp. 603-604 (2001). In one embodiment, a non-limiting, process involves dissolving the compound of formula (1), (1A), (1B), or (1C) or a pharmaceutically acceptable salt thereof, or the compound of formula (1D), (1E), or (1F) in a desired amount of the solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The methods of the disclosure provided herein also encompass the use of a compound of formula (1), (1A), (1B), or (1C) or a pharmaceutically acceptable salt or solvate thereof, or a compound of formula (1D), (1E), or (1F) or a solvate thereof where one or more hydrogen, carbon or other atoms is replaced by a radioactive isotope of the hydrogen, carbon or other atoms. Such a "radiolabeled" compound of formula (1), (1A), (1B), or (1C) or a pharmaceutically acceptable salt or solvate thereof, or a compound of formula (1D), (1E), or (1F) or a solvate thereof, each of which is encompassed by the disclosure, is useful as a research and/or diagnostic tool in metabolism pharmacokinetic studies and in binding assays. "Radioactive", as used herein means a compound that comprises at least one radioactive atom such that the specific radioactivity thereof is above the background level of radioactivity. Examples of radioactive isotopes that can be incorporated into a compound of formula (1), (1A), (1B), or (1C) or a pharmaceutically acceptable salt or solvate thereof, or a compound of formula (1D), (1E), or (1F) or a solvate thereof of the disclosure include isotopes of hydrogen, carbon, nitrogen, and oxygen, such as, for example, $^{2}H$, $^{3}H$, $^{11}C$, $^{13}C$, $^{14}C$, $^{15}N$, $^{17}O$, and $^{18}O$. In one embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1, 2, 3, 4, or more radioactive isotopes, each of which is independently selected from hydrogen, carbon, nitrogen, and oxygen. In another embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1 or 2 radioactive isotopes, each of which is independently selected from $^{3}H$, $^{14}C$, and $^{15}N$. In another embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1 radioactive isotope which is selected from $^3$H, $^{14}$C, and $^{15}$N. In another embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1 radioactive isotope which is $^3$H. In another embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1 radioactive isotope which is $^{14}$C. In another embodiment, a radiolabeled compound of formula (1), (1A), (1B), or (1C) or a pharmaceutically acceptable salt or solvate thereof, or a radiolabeled compound of formula (1D), (1E), or (1F) or a solvate thereof contains 1 radioactive isotope which is $^{15}$N.

Radiolabeled compounds for use in the methods of the disclosure can be prepared by methods known in the art. For example, a tritiated compound of formula (1), (1A), (1B), or (1C) or a pharmaceutically acceptable salt or solvate thereof, or a tritiated compound of formula (1D), (1E), or (1F) or a solvate thereof can be prepared by introducing tritium into the particular compound of formula (1), (1A), (1B), or (1C) or a pharmaceutically acceptable salt or solvate thereof, or the compound of formula (1D), (1E), or (1F) or a solvate thereof, for example, by catalytic dehalogenation with tritium. This method can include reacting a suitably halogen-substituted precursor of a compound of formula (1), (1A), (1B), or (1C) or a pharmaceutically acceptable salt or solvate thereof, or a compound of formula (1D), (1E), or (1F) or a solvate thereof with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences, Vol. 1, Labeled Compounds (Part A)*, Buncel et al., eds., Chapter 6, pp. 155-192 (1987). $^{14}$C-labeled compounds can be prepared by employing starting materials having a $^{14}$C carbon. Compounds containing, e.g., piperazine, isotopically enriched with $^{13}$C and/or $^{15}$N can be prepared as described in, e.g., FIG. 5A and the associated description, of U.S. Pat. No. 7,355,045 B2.

A compound of formula (1), (1A), or (1B) or a pharmaceutically acceptable salt or solvate thereof can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms, and all mixtures thereof. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and related terms as used herein are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a compound of formula (1), (1A), or (1B) can be obtained by known techniques such as chiral chromatography or formation of diastereomeric salts from an optically active acid or base.

Optical purity can be stated in terms of enantiomeric excess ("% ee") and/or diastereomeric excess (% de), each which is determined by the appropriate formula below:

$$\% \ ee = \left[\frac{\text{major enantiomer (mol)} - \text{minor enantiomer (mol)}}{\text{major enantiomer (mol)} + \text{minor enantiomer (mol)}}\right] \times 100\%$$

$$\% \ de = \left[\frac{\text{major diastereomer (mol)} - \text{minor diastereomers (mol)}}{\text{major diastereomer (mol)} + \text{minor diastereomers (mol)}}\right] \times 100\%.$$

The term "effective amount", when used in connection with methods for treating or preventing a sleep disorder by administering a compound of formula (1), (1A), (1B), or (1C) or a pharmaceutically acceptable salt or solvate thereof, or a compound of formula (1D), (1E), or (1F) or a solvate thereof, refers to an amount of the compound administered to an animal that provides a therapeutic effect.

The term "effective amount", when used in connection with a second therapeutic agent means an amount for providing the therapeutic effect of the second therapeutic agent.

The terms "modulate", "modulating", and related terms as used herein with respect to the ORL-1 receptor mean the mediation of a pharmacodynamic response (e.g., insomnia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman and Gilman's The Pharmacological Basis of Therapeutics* pp. 31-43 (Goodman et al., eds., 10$^{th}$ Ed., McGraw-Hill, New York 2001)).

The terms "treatment of", "treating", and related terms as used herein include the amelioration, reduction, slowing, or cessation of a Condition or a symptom thereof by administration of an effective amount of a compound of formula (1), (1A), (1B), or (1C) or a pharmaceutically acceptable salt or solvate thereof, or a compound of formula (1D), (1E), or (1F) or a solvate thereof. In some embodiments, treating includes inhibiting, for example, decreasing the overall frequency of episodes of a Condition or a symptom thereof or reducing the severity of a Condition or a symptom thereof.

The terms "prevention of", "preventing", and related terms as used herein include the avoidance of the onset of a Condition or a symptom thereof by administration of an effective amount of a compound of formula (1), (1A), (1B), or (1C) or a pharmaceutically acceptable salt or solvate thereof, or a compound of formula (1D), (1E), or (1F) or a solvate thereof.

A "disorder" includes, but is not limited to, the Conditions defined herein. In one embodiment, a disorder relates to a Condition or symptom of insufficient sleep, or resulting from insufficient sleep, or difficulty falling asleep or staying asleep.

The amount by weight of the administered "dose", "dosage", and related terms as used herein refers to the free acid and free base form of a compound of formula (1), (1A), (1B), or (1C), i.e., the no-salt form. For example, a 10.0 mg dose of the no-salt form of the compound of formula (1) means that 10.0 mg is actually administered. However, by way of example, a 10.0 mg dose of, e.g., the monohydrochloride or the 1:1 by moles hydrochloric acid salt of the compound of formula (1) (i.e., the compound of formula (1E)) means that 10.84 mg of said compound is actually administered, which 10.84 mg provides 10.00 mg of the no-salt form of the compound of formula (1) (0.0229 mmoles) and 0.84 mg of hydrochloric acid (0.0229 mmoles). Also by way of example, a 10.0 mg dose of, e.g., the monosodium salt of the compound of formula (1) means that 10.57 mg of said compound is actually administered, which 10.57 mg provides 10.00 mg of the no-salt form of the compound of formula (1) (0.0229 mmoles) and 0.57 mg of sodium (0.0229 mmoles). Likewise, a 10.00 mg dose of, e.g., the mono-tosylate salt (1:1 by moles para-toluenesulfonic acid salt) of the compound of formula (1C), i.e., the compound of formula (1D), means that 13.93 mg of said compound is actually administered, which 13.93 mg provides 10.00 mg of the no-salt form of the compound of formula (1C) (0.0229 mmoles) and 3.93 mg of para-toluenesulfonic acid (0.0229 mmoles).

The term "UI" means urinary incontinence. The term "IBD" means inflammatory-bowel disease. The term "IBS" means irritable-bowel syndrome. The term "ALS" means amyotrophic lateral sclerosis.

The term "N/A" as used herein means not applicable.

The term "SD" as used herein means standard deviation.

The term "LSM" as used herein means least-squares mean.

The term "STDE" as used herein means standard error.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

5.5 Therapeutic Uses of the Compound of Formula (1), (1A), (1B), (1C), (1D), (1E), and (1F)

In accordance with the disclosure, the compounds of formula (1), (1A), (1B), and (1C) or a pharmaceutically acceptable salt or solvate thereof, and the compounds of formula (1D), (1E), and (1F) or a solvate thereof are administered to an animal in need of treatment or prevention of a Condition.

In one embodiment, an effective amount of a compound of formula (1), (1A), (1B), or (1C) or a pharmaceutically acceptable salt or solvate thereof, or a compound of formula (1D), (1E), or (1F) or a solvate thereof can be used to treat or prevent a sleep disorder treatable or preventable by modulating the activity of the ORL-1 receptor.

An effective amount of a compound of formula (1), (1A), (1B), or (1C) or a pharmaceutically acceptable salt or solvate thereof, or a compound of formula (1D), (1E), or (1F) or a solvate thereof can be used to treat or prevent a sleep disorder including, but not limited to insomnia, such as "adult" insomnia, child insomnia, middle-of-the-night insomnia, and short sleeper disorder; hypersomnia, such as insufficient sleep syndrome; circadian rhythm sleep-wake disorder, such as delayed sleep-wake phase, advanced sleep-wake phase, irregular sleep-wake rhythm, non-24-hour sleep-wake rhythm, shift work syndrome, and jet lag; or any combination thereof. Other sleep disorders that can be treated or prevented by a compound of formula (1), (1A), (1B), or (1C) or a pharmaceutically acceptable salt or solvate thereof, or a compound of formula (1D), (1E), or (1F) or a solvate thereof include types of dyssomnia not already referenced in this paragraph, food allergy insomnia, alcohol-dependent sleep disorder, and/or alcohol-induced sleep disorder.

In connection with alcohol-related sleep disorders, DSM-5 also sets out alcohol-induced sleep disorder as a principal diagnosis and subdivides the sleep disorder into four types: insomnia, daytime sleepiness, parasomnia, and mixed type. It discloses that alcohol-induced sleep disorder typically occurs as "insomnia type", that is, sleep disorder characterized by "difficulty falling asleep or maintaining sleep, frequent nocturnal awakenings, or nonrestorative sleep." Specifically, Conroy discloses alcohol consumption has a "biphasic" effect on sleep within a night. That is, in the earlier portion of the night an alcohol dose can provide an immediate sedative effect with shorter LPS and an increased duration of Stage N3 sleep. However, in the later portion of the night sleep quality deteriorates and there is a greater NAW. Yet another reference concludes that virtually every type of sleep problem occurs in alcohol-dependent patients, typically, a long LPS, low SE, short TST, reduced duration of Stage N3 sleep, fragmented sleep patterns, and severely disrupted sleep architecture (Landolt et al., "Sleep Abnormalities During Abstinence in Alcohol-Dependent Patients: Aetiology and Management," *CNS Drugs* 15(5):413-425 (2001)).

Even alcoholics who have been abstinent, either for short periods of time (several weeks) or extended periods of time (several years), can experience persistent sleep abnormalities such as increased LPS, frequent MOTN awakening, and poor sleep quality. In summarizing the results of multiple studies, Brower concludes that alcoholics who had been abstinent for 2-8 weeks exhibited worse sleep than did non-alcoholics, that is, TST, SE, and the amount of time spent in Stage N3 sleep generally decreased significantly whereas Stage N1 sleep time usually increased and LPS increased significantly. Moreover, sleep abnormalities can persist for 1-3 years after alcohol consumption ends. For example, Brower concludes that sleep fragmentation, expressed as increases in sleep-stage changes, brief arousals, and REM sleep disruptions, can persist for 1-3 years after establishing sobriety. Diminished REM sleep time is understood to be associated with negative cognitive consequences, e.g., poor procedural learning.

Moreover, it is recognized that the consumption of alcohol can damage the human liver, a vital organ that filters harmful substances from the blood and manufactures various substances, such as hormones, proteins, and enzymes, that the body requires. Alcohol-related liver disease ("ALD") is caused by excessive consumption of alcohol. Its mildest form, steatosis or fatty liver, is characterized by an excessive accumulation of fat inside liver cells, making liver functioning more difficult. A more severe form of ALD that can develop from is steatosis is alcoholic hepatitis, either chronic or acute. It manifests as the inflammation or swelling of the liver accompanied by the destruction of liver cells and makes liver functioning even more difficult. The most severe form of ALD that can develop from excess alcohol consumption is alcoholic cirrhosis. It is characterized by the replacement of normal liver tissue with nonliving scar tissue. Alcoholic cirrhosis can be a life-threatening disease because of the associated severe impairment of liver functioning.

Thus, there remains an unmet need for a safe and effective medication to treat sleep disorders or disturbances, e.g., insomnia, that are associated with alcohol use disorder, alcohol dependence, alcohol-induced sleep disorder, and/or alcohol cessation. In one desirable embodiment, such medication would still function effectively even when the liver suffers from alcohol-induced damage in the form of steatosis, alcoholic hepatitis, and/or alcoholic cirrhosis.

The disclosure also relates to methods for activating ORL-1 receptor function in a cell, comprising contacting a cell capable of expressing the ORL-1 receptor with an amount of a compound of formula (1), (1A), (1B), or (1C) or a pharmaceutically acceptable salt or solvate thereof, or a compound of formula (1D), (1E), or (1F) or a solvate thereof effective to activate ORL-1 receptor function in the cell. This method can be adapted for use in vitro as part of an assay to select compounds useful for treating or preventing a sleep disorder. Alternatively, the method can be adapted for use in vivo (i.e., in an animal such as a human), by contacting a cell in the animal with an effective amount of a compound of formula (1), (1A), (1B), or (1C) or a pharmaceutically acceptable salt or solvate thereof, or a compound of formula (1D), (1E), or (1F) or solvate thereof. In one embodiment, the method is useful for treating or preventing a sleep disorder in an animal in need of such treatment or prevention.

5.6 Therapeutic/Prophylactic Administration and Compositions of the Disclosure

Due to their activity, the compounds of formula (1), (1A), (1B), and (1C) or a pharmaceutically acceptable salt or solvate thereof, and the compounds of formula (1D), (1E), and (1F) or a solvate thereof are advantageously useful in human and veterinary medicine. As described above, the compounds of formula (1), (1A), (1B), and (1C) or a pharmaceutically acceptable salt or solvate thereof, and the compounds of formula (1D), (1E), and (1F) or a solvate thereof are useful for treating or preventing a Condition in an animal in need thereof. In another embodiment, the compounds of formula (1), (1A), (1B), and (1C) or a pharmaceutically acceptable salt or solvate thereof, and the compounds of formula (1D), (1E), and (1F) or a solvate thereof are useful for treating a Condition in an animal in need thereof. In another embodiment, the compounds of formula (1), (1A), (1B), and (1C) or a pharmaceutically acceptable salt or solvate thereof, and the compounds of formula (1D), (1E), and (1F) or a solvate thereof are useful for preventing a Condition in an animal in need thereof. In another embodiment, the compounds of formula (1), (1A), (1B), and (1C) or a pharmaceutically acceptable salt or solvate thereof, and the compounds of formula (1D), (1E), and (1F) or a solvate thereof of the disclosure can be administered to any animal requiring modulation of the opioid and/or ORL-1 receptors.

When administered to an animal, a compound of formula (1), (1A), (1B), or (1C) or a pharmaceutically acceptable salt or solvate thereof, or a compound of formula (1D), (1E), or (1F) or a solvate thereof can be administered as a component of a composition that comprises a pharmaceutically acceptable carrier or excipient.

Methods of administration include, but are not limited to, intradermal, intramuscular, intraperitoneal, parenteral, intravenous, subcutaneous, intranasal, epidural, oral, transmucosal, buccal, gingival, sublingual, intraocular, intracerebral, intravaginal, transdermal (e.g., via a patch), rectal, by inhalation, or topical, particularly to the ears, nose, eyes, or skin. In another embodiment, methods of administration include, but are not limited to, intravenous, oral, or by inhalation. In another embodiment, the method of administration is oral. In another embodiment, the method of administration is intravenous. In another embodiment, the method of administration is by inhalation. The method of administration is left to the discretion of the practitioner. In some instances, administration will result in the release of a compound of formula (1), (1A), (1B), or (1C) or a pharmaceutically acceptable salt or solvate thereof, or a compound of formula (1D), (1E), or (1F) or a solvate thereof into the bloodstream. In other instances, administration will result in only local release of a compound of formula (1), (1A), (1B), or (1C) or a pharmaceutically acceptable salt or solvate thereof, or a compound of formula (1D), (1E), or (1F) or a solvate thereof.

In certain embodiments, it can be desirable to introduce a compound of formula (1), (1A), (1B), or (1C) or a pharmaceutically acceptable salt or solvate thereof, or a compound of formula (1D), (1E), or (1F) or a solvate thereof into the central nervous system or gastrointestinal tract by any suitable route, including intraventricular, intrathecal, or epidural injection, or enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound of formula (1), (1A), (1B), or (1C) or a pharmaceutically acceptable salt or solvate thereof, or a compound of formula (1D), (1E), or (1F) or a solvate thereof can be formulated as a suppository, with traditional binders and excipients such as triglycerides.

When a compound of formula (1), (1A), (1B), or (1C) or a pharmaceutically acceptable salt or solvate thereof, or a compound of formula (1D), (1E), or (1F) or a solvate thereof of the disclosure is incorporated for parenteral administration by injection (e.g., continuous infusion or bolus injection), the formulation for parenteral administration can be in the form of a suspension, solution, emulsion in an oily or aqueous vehicle. Such formulations can further comprise pharmaceutically necessary additives such as one or more stabilizing agents, suspending agents, dispersing agents, buffers, and the like. A compound of formula (1), (1A), (1B), or (1C) or a pharmaceutically acceptable salt or solvate thereof, or a compound of formula (1D), (1E), or (1F) or a solvate thereof of the disclosure can also be in the form of a powder for reconstitution as an injectable formulation.

In another embodiment, a compound of formula (1), (1A), (1B), or (1C) or a pharmaceutically acceptable salt or solvate thereof, or a compound of formula (1D), (1E), or (1F) or a solvate thereof can be delivered in a vesicle, in particular a liposome (see Langer, "New Methods of Drug Delivery," *Science* 249:1527-1533 (1990); and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, a compound of formula (1), (1A), (1B), or (1C) or a pharmaceutically acceptable salt or solvate thereof, or a compound of formula (1D), (1E), or (1F) or a solvate thereof can be delivered in a controlled-release system or sustained-release system. Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a compound of formula (1), (1A), (1B), or (1C) or a pharmaceutically acceptable salt or solvate thereof, or a compound of formula (1D), (1E), or (1F) or a solvate thereof to treat or prevent the Condition or a symptom thereof in an extended amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the compound of formula (1), (1A), (1B), or (1C) or a pharmaceutically acceptable salt or solvate thereof, or a compound of formula (1D), (1E), or (1F) or a solvate thereof, and can thus reduce the occurrence of adverse side effects.

Controlled- or sustained-release compositions can initially release an amount of a compound of formula (1), (1A), (1B), or (1C) or a pharmaceutically acceptable salt or solvate thereof, or a compound of formula (1D), (1E), or (1F) or a solvate thereof that promptly produces the desired therapeutic or prophylactic effect, and gradually and continually release other amounts of the compound of formula (1), (1A), (1B), or (1C) or a pharmaceutically acceptable salt or solvate thereof, or the compound of formula (1D), (1E), or (1F) or a solvate thereof to maintain this level of therapeutic or prophylactic effect over an extended period of time. To maintain a constant level of the compound of formula (1), (1A), (1B), or (1C) or a pharmaceutically acceptable salt or solvate thereof, or the compound of formula (1D), (1E), or (1F) or a solvate thereof in the body, the compound of formula (1), (1A), (1B), or (1C) or a pharmaceutically acceptable salt or solvate thereof, or the compound of formula (1D), (1E), or (1F) or a solvate thereof can be released from the dosage form at a rate that will replace the amount of the compound of formula (1), (1A), (1B), or (1C) or a pharmaceutically acceptable salt or solvate thereof, or the compound of formula (1D), (1E), or (1F) or a solvate thereof being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds. In yet another embodiment, a controlled- or sustained-release system can be placed in proximity of a target of a compound of formula (1), (1A), (1B), or (1C) or a pharmaceutically acceptable salt or solvate thereof, or a compound of formula (1D), (1E), or (1F) or a solvate thereof, e.g., the spinal column or brain, thus requiring only a fraction of the systemic dose.

Administration of a compound of formula (1), (1A), (1B), or (1C) or a pharmaceutically acceptable salt or solvate thereof, or a compound of formula (1D), (1E), or (1F) or a solvate thereof can be by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Numerous other controlled-release or sustained-release delivery devices that are known to those in the art (see, e.g., Goodson, "Dental Applications," in *Medical Applications of Controlled Release, Vol. 2, Applications and Evaluation*, Langer and Wise, eds., CRC Press, Chapter 6, pp. 115-138 (1984), hereafter "Goodson"). Other controlled- or sustained-release systems discussed in the review by Langer, *Science* 249: 1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J Med.* 321:574-579 (1989)). In another embodiment, polymeric materials can be used (see Goodson; Smolen et al., "Drug Product Design and Performance," *Controlled Drug Bioavailability* Vol. 1, John Wiley and Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105-112 (1989)).

Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

The compositions can optionally, but preferably, further comprise a suitable amount of a pharmaceutically acceptable excipient so as to provide the form for proper administration to the animal Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal Water is a particularly useful excipient when a compound of formula (1), (1A), (1B), or (1C) or a pharmaceutically acceptable salt or solvate thereof, or a compound of formula (1D), (1E), or (1F) or a solvate thereof is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, D C, 1986), incorporated herein by reference. Other examples of suitable pharmaceutical excipients are described by Radebough et al., "Preformulation," pp. 1447-1676 in *Remington's Pharmaceutical Sciences* Vol. 2 (Gennaro, ed., 19$^{th}$ Ed., Mack Publishing, Easton, Pa., 1995), incorporated herein by reference.

The compositions can take the form of solutions, suspensions, emulsions, tablets such as an orally disintegrating tablet (ODT) or a sublingual tablet, pills, pellets, capsules, capsules containing liquids, powders, sustained-release formulations, suppositories, emulsions, aerosols, sprays, suspensions, microparticles, multiparticulates, rapidly dissolving films or other forms for oral or mucosal administration, or any other form suitable for use. In one embodiment, the composition is in the form of an ODT (see, e.g., U.S. Pat. Nos. 7,749,533 and 9,241,910). In another embodiment, the composition is in the form of a sublingual tablet (see, e.g., U.S. Pat. Nos. 6,572,891 and 9,308,175). In another embodiment, the composition is in the form of a capsule (see, e.g., U.S. Pat. No. 5,698,155). In another embodiment, the composition is in a form suitable for buccal administration, e.g., as a tablet, lozenge, gel, patch, or film, formulated in a conventional manner (see, e.g., Pather et al., "Current status and the future of buccal drug delivery systems," *Expert Opin. Drug Deliv.* 5(5):531-542 (2008)). In another embodiment, the composition is in a form suitable for gingival administration, e.g., as a polymeric film comprising polyvinyl alcohol, chitosan, polycarbophil, hydroxypropylcellulose, or Eudragit S-100, as disclosed by Padula et al., "In Vitro Evaluation of Mucoadhesive Films for Gingival Administration of Lidocaine," *AAPS PharmSciTech* 14(4): 1279-1283 (2013). In another embodiment, the composition is in a form suitable for intraocular administration.

In one embodiment, the compounds of formula (1), (1A), (1B), or (1C) or a pharmaceutically acceptable salt or solvate thereof, or the compounds of formula (1D), (1E), or (1F) or a solvate thereof are formulated in accordance with routine procedures as a composition adapted for oral administration to human beings. A compound of formula (1), (1A), (1B), or (1C) or a pharmaceutically acceptable salt or solvate thereof, or a compound of formula (1D), (1E), or (1F) or a solvate thereof to be orally delivered can be in the form of tablets, capsules, gelcaps, caplets, lozenges, aqueous or oily solutions, suspensions, granules, microparticles, multiparticulates, powders, emulsions, syrups, or elixirs, for example. When a compound of formula (1), (1A), (1B), or (1C) or a pharmaceutically acceptable salt or solvate thereof, or a compound of formula (1D), (1E), or (1F) or a solvate thereof is incorporated into oral tablets, such tablets can be compressed, tablet triturates, enteric-coated, sugar-coated, film-coated, multiply compressed, or multiply layered. Techniques and compositions for making solid oral dosage forms are described in *Pharmaceutical Dosage Forms: Tablets* (Lieberman et al., eds., 2$^{nd}$ Ed., Marcel Dekker, Inc., 1989 and 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16$^{th}$ Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2$^{nd}$ Ed., Marcel Dekker, Inc., 1996 and 1998).

An orally administered compound of formula (1), (1A), (1B), or (1C) or a pharmaceutically acceptable salt or solvate thereof, or a compound of formula (1D), (1E), or (1F) or a solvate thereof can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

When a compound of formula (1), (1A), (1B), or (1C) or a pharmaceutically acceptable salt or solvate thereof, or a compound of formula (1D), (1E), or (1F) or a solvate thereof is to be injected parenterally, it can be, e.g., in the form of an isotonic sterile solution. Alternatively, when a compound of formula (1), (1A), (1B), or (1C) or a pharmaceutically acceptable salt or solvate thereof, or a compound of formula (1D), (1E), or (1F) or a solvate thereof is to be inhaled, it can be formulated into a dry aerosol or can be formulated into an aqueous or partially aqueous solution.

In another embodiment, the compounds of formula (1), (1A), (1B), or (1C) or a pharmaceutically acceptable salt or solvate thereof, or the compounds of formula (1D), (1E), or (1F) or a solvate thereof can be formulated for intravenous administration. In certain embodiments, compositions for intravenous administration comprise sterile isotonic aqueous buffer. Where necessary, the compositions can also include a solubilizing agent. A compound of formula (1), (1A), (1B), or (1C) or a pharmaceutically acceptable salt or solvate thereof, or a compound of formula (1D), (1E), or (1F) or a solvate thereof for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a compound of formula (1), (1A), (1B), or (1C) or a pharmaceutically acceptable salt or solvate thereof, or a compound of formula (1D), (1E), or (1F) or a solvate thereof is to be administered by infusion, it can be dispensed, for example, with an infusion bottle containing sterile pharmaceutical grade water or saline. Where a compound of formula (1), (1A), (1B), or (1C) or a pharmaceutically acceptable salt or solvate thereof, or a compound of formula (1D), (1E), or (1F) or a solvate thereof is administered by injection, an ampule of sterile water for injection or saline can be provided so that the ingredients can be mixed prior to administration.

The amount of the compound of formula (1), (1A), (1B), or (1C) or a pharmaceutically acceptable salt or solvate thereof, or the compound of formula (1D), (1E), or (1F) or a solvate thereof that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the disorder to be treated, the severity of the symptoms, the frequency of the dosage interval, the presence of any deleterious side-effects, and the particular compound utilized, among other things.

Suitable effective dosage amounts of the compound of formula (1), (1A), (1B), or (1C) or a pharmaceutically acceptable salt or solvate thereof, or the compound of formula (1D), (1E), or (1F) or a solvate thereof are from about 0.0002 mg/kg to about 25 mg/kg of body weight of the animal per day in one embodiment, from about 0.00025 mg/kg/day to about 20 mg/kg/day in another embodiment, from about 15 mg/kg/day to about 600 mg/kg/day in another embodiment, from about 20 mg/kg/day to about 600 mg/kg/day in another embodiment, from about 25 mg/kg/day to about 600 mg/kg/day in another embodiment, and from about 30 mg/kg/day to about 600 mg/kg/day in another embodiment. In another embodiment, the effective dosage amount is about 10.0 mg/kg/day or less. In certain embodiments, suitable effective dosage amounts of the compound of formula (1), (1A), (1B), or (1C) or a pharmaceutically acceptable salt or solvate thereof, or the compound of formula (1D), (1E), or (1F) or a solvate thereof are from about 0.0002 mg/kg/day to about 10 mg/kg/day, from about 0.001 mg/kg/day to about 10 mg/kg/day, from about 0.002 mg/kg/day to about 10 mg/kg/day, from about 0.003 mg/kg/day to about 10 mg/kg/day, from about 0.0005 mg/kg/day to about 5.0 mg/kg/day, from about 0.001 mg/kg/day to about 2.5 mg/kg/day, from about 0.002 mg/kg/day to about 2.0 mg/kg/day, or from about 0.002 mg/kg/day to about 1.0 mg/kg/day. In another embodiment, the effective dosage amount is about 1.0 mg/kg/day or less. In certain other embodiments, suitable effective dosage amounts of the compound of formula (1), (1A), (1B), or (1C) or a pharmaceutically acceptable salt or solvate thereof, or the compound of formula (1D), (1E), or (1F) or a solvate thereof are from about 0.001 mg/kg/day to about 1.0 mg/kg/day, from about 0.002 mg/kg/day to about 0.8 mg/kg/day, from about 0.0025 mg/kg/day to about 0.5 mg/kg/day, from about 0.003 mg/kg/day to about 0.15 mg/kg/day, from about 0.006 mg/kg/day to about 0.12 mg/kg/day, or from about 0.010 mg/kg/day to about 0.10 mg/kg/day. It is to be understood that for these dosage amounts, the term "day" means a 24 hour cycle beginning at the time of administration of a compound of formula (1), (1A), (1B), or (1C) or a pharmaceutically acceptable salt or solvate thereof, or a compound of formula (1D), (1E), or (1F) or a solvate thereof. For example, for an ordinary overnight sleep cycle, if a compound of formula (1), (1A), (1B), or (1C) or a pharmaceutically acceptable salt or solvate thereof, or a compound of formula (1D), (1E), or (1F) or a solvate thereof is administered at 9:30 PM, then that "day" ends at 9:29 PM on the following calendar day. In another example, for a shift-worker's sleep cycle, if a compound of formula (1), (1A), (1B), or (1C) or a pharmaceutically acceptable salt or solvate thereof, or a compound of formula (1D), (1E), or (1F) or a solvate thereof is administered at 8:15 AM, then that "day" ends at 8:14 AM on the following calendar day.

A suitable effective dosage amount of the compound of formula (1), (1A), (1B), or (1C) or a pharmaceutically acceptable salt or solvate thereof, or the compound of formula (1D), (1E), or (1F) or a solvate thereof administered as a single dose is from about 0.06 mg to about 600 mg, from about 0.05 mg to about 50 mg, from about 0.12 mg to about 600 mg, from about 0.10 mg to about 30 mg, from about 0.10 mg to about 20 mg, from about 0.10 mg to about 15 mg, from about 0.10 mg to about 10 mg, from about 0.10 mg to about 8 mg, from about 0.10 mg to about 7 mg, from about 0.15 mg to about 30 mg, from about 0.15 mg to about 20 mg, from about 0.15 mg to about 15 mg, from about 0.15 mg to about 10 mg, from about 0.15 mg to about 8 mg, from about 0.15 mg to about 7 mg, from about 0.18 mg to about 9 mg, from about 0.18 mg to about 6 mg, from about 0.18 mg to about 4.0 mg, from about 0.2 mg to about 30 mg, from about 0.2 mg to about 20 mg, from about 0.2 mg to about 15 mg, from about 0.2 mg to about 10 mg, from about 0.2 mg to about 8 mg, from about 0.2 mg to about 7 mg, from about 0.2 mg to about 6.0 mg, from about 0.2 mg to about 4.0 mg, from about 0.2 mg to about 3.0 mg, from about 0.2 mg to about 2.0 mg, from about 0.2 mg to about 1.0 mg, from about 0.5 mg to about 6.0 mg, from about 0.5 mg to about 4.0 mg, from about 0.5 mg to about 3.0 mg, from about 0.5 mg to about 2.0 mg, from about 0.5 mg to about 1.0 mg, from about 0.6 mg to about 6.0 mg, or from about 0.6 mg to about 4.0 mg, although it is, in certain embodiments, about 0.05 mg, about 0.06 mg, about 0.07 mg, about 0.08 mg, about 0.09 mg, about 0.100 mg, about 0.120 mg, about 0.125 mg, about 0.150 mg, about 0.175 mg, about 0.200 mg, about 0.225 mg, about 0.250 mg, about 0.275 mg, about 0.30 mg, about 0.35 mg, about 0.40 mg, about 0.45 mg, about 0.50 mg, about 0.55 mg, about 0.60 mg, about 0.65 mg, about 0.70 mg, about 0.75 mg, about 0.80 mg, about 0.85 mg, about 0.90 mg, about 0.95 mg, about 1.00 mg, about 1.25 mg, about 1.50 mg, about 1.75 mg, about 2.00 mg, about 2.25 mg, about 2.50 mg, about 2.75 mg, about 3.00 mg, about 3.25 mg, about 3.50 mg, about 3.75 mg, about 4.0 mg, about 4.5 mg, about 5.0 mg, about 5.5 mg, about 6.0 mg, about 6.5 mg, about 7.0 mg, about 7.5 mg, about 8.0 mg, about 9.0 mg, about 10 mg, about 12 mg, about 12.5 mg, about 15 mg, about 20 mg, about 25 mg, about 30 mg, about 40 mg, about 50 mg, about 70 mg, about 100 mg, about 120 mg, about 150 mg, about 175 mg, or about 200 mg. As known to those in the art, for a human animal, a single daily dose (in mg) can be converted to a mg/kg/day dosage amount by dividing the mg dose by 60 kg, the art-recognized average mass of a human animal. For example, a single daily human dose of 1.25 mg is so-converted to a dosage amount of about 0.021 mg/kg/day.

The effective dosage amounts described herein refer to total amounts administered; that is, if more than one compound of formula (1), (1A), (1B), or (1C) or a pharmaceutically acceptable salt or solvate thereof, or more than one compound of formula (1D), (1E), or (1F) or a solvate thereof is administered, the effective dosage amounts correspond to the total amount administered.

Administration can be as a single dose or as a divided dose. In one embodiment, an effective dose or dosage amount is administered only as needed (pro re nata) such as, for example, in the event that sleep cannot readily be achieved, or upon middle-of-the night awakening followed by failure to readily return to sleep. In another embodiment, an effective dose or dosage amount is administered about every 24 hours, for example, in preparation for sleep, until the Condition is abated. In another embodiment, a single effective dose or dosage amount is administered in preparation for sleep to abate the Condition. In another embodiment, a single effective dose or dosage amount is administered in preparation for sleep on two consecutive days to abate the Condition. In another embodiment, a single effective dose or dosage amount is administered in preparation for sleep on three consecutive days to abate the Condition. In another embodiment, a single effective dose or dosage amount is administered in preparation for sleep on four consecutive days to abate the Condition. In another embodiment, a single effective dose or dosage amount is administered in preparation for sleep on five consecutive days to abate the Condition. In another embodiment, a single effective dose or dosage amount is administered in preparation for sleep on six consecutive days to abate the Condition. In another embodiment, a single effective dose or dosage amount is administered in preparation for sleep on seven consecutive days to abate the Condition. In another embodiment, a single effective dose or dosage amount is administered in preparation for sleep on eight consecutive days to abate the Condition. In another embodiment, a single effective dose or dosage amount is administered in preparation for sleep on nine consecutive days to abate the Condition. In another embodiment, a single effective dose or dosage amount is administered in preparation for sleep on 10 consecutive days to abate the Condition. In another embodiment, a single effective dose or dosage amount is administered in preparation for sleep on up to 12 consecutive days to abate the Condition. In another embodiment, a single effective dose or dosage amount is administered in preparation for sleep on 12 consecutive days to abate the Condition. In another embodiment, a single effective dose or dosage amount is administered in preparation for sleep on up to 14 consecutive days to abate the Condition. In another embodiment, a single effective dose or dosage amount is administered in preparation for sleep on 14 consecutive days to abate the Condition. In another embodiment, a single effective dose or dosage amount is administered in preparation for sleep on up to 21 consecutive days to abate the Condition. In another embodiment, a single effective dose or dosage amount is administered in preparation for sleep on 21 consecutive days to abate the Condition. In another embodiment, a single effective dose or dosage amount is administered in preparation for sleep on up to 28 consecutive days to abate the Condition. In another embodiment, a single effective dose or dosage amount is administered in preparation for sleep on 28 consecutive days to abate the Condition. In another embodiment, a single effective dose or dosage amount is administered in preparation for sleep on at least 28 consecutive days to abate the Condition.

In one embodiment, an effective dose or dosage amount is administered about 60 minutes before an animal's median habitual bedtime. In another embodiment, an effective dose or dosage amount is administered about 45 minutes before an animal's median habitual bedtime. In another embodiment, an effective dose or dosage amount is administered about 30 minutes before an animal's median habitual bedtime. In another embodiment, an effective dose or dosage amount is administered about 20 minutes before an animal's median habitual bedtime. In another embodiment, an effective dose or dosage amount is administered about 20 minutes or less before an animal's median habitual bedtime. In another embodiment, an effective dose or dosage amount is administered about 15 minutes before an animal's median habitual bedtime. In another embodiment, an effective dose or dosage amount is administered about 15 minutes or less before an animal's median habitual bedtime. In another embodiment, an effective dose or dosage amount is administered about 10 minutes before an animal's median habitual bedtime. In another embodiment, an effective dose or dosage amount is administered about 10 minutes or less before an animal's median habitual bedtime. In another embodiment, an effective dose or dosage amount is administered about 5 minutes before an animal's median habitual bedtime. In another embodiment, an effective dose or dosage amount is administered about 5 minutes or less before an animal's median habitual bedtime. In another embodiment, an effective dose or dosage amount is administered about 2 minutes before an animal's median habitual bedtime. In another embodiment, an effective dose or dosage amount is administered about 2 minutes or less before an animal's median habitual bedtime. In another embodiment, an effective dose or dosage amount is administered about 1 minute before an animal's median habitual bedtime.

In one embodiment, a composition comprising a compound of formula (1), (1A), (1B), or (1C) or a pharmaceutically acceptable salt or solvate thereof, or a compound of formula (1D), (1E), or (1F) or a solvate thereof, in accordance with the disclosure is used as a medicament. In another embodiment, compositions comprising a compound of formula (1), (1A), (1B), or (1C) or a pharmaceutically acceptable salt or solvate thereof, or a compound of formula (1D), (1E), or (1F) or a solvate thereof, are disclosed which can be used for preparing a medicament containing said compositions.

In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment or prevention of a sleep disorder. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment or prevention of a sleep disorder where the sleep disorder is an insomnia condition, a hypersomnia condition, a circadian rhythm sleep-wake disorder, an alcohol-induced sleep disorder, or any combination thereof.

In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment of a sleep disorder. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment of a sleep disorder where the sleep disorder is an insomnia condition, a hypersomnia condition, a circadian rhythm sleep-wake disorder, an alcohol-induced sleep disorder, or any combination thereof.

In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the prevention of a sleep disorder. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the prevention of a sleep disorder where the sleep disorder is an insomnia condition, a hypersomnia condition, a circadian rhythm sleep-wake disorder, an alcohol-induced sleep disorder, or any combination thereof.

In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment or prevention of an insomnia condition. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment of an insomnia condition. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the prevention of an insomnia condition.

In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment or prevention of an alcohol-induced sleep disorder. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the treatment of an alcohol-induced sleep disorder. In another embodiment, a composition comprising a compound of formula (1), (1A), (1B), or (1C) or a pharmaceutically acceptable salt or solvate thereof, or a compound of formula (1D), (1E), or (1F) or a solvate thereof, is useful as a medicament in the prevention of an alcohol-induced sleep disorder.

For any of these uses, the composition comprising a compound of formula (1), (1A), (1B), or (1C) or a pharmaceutically acceptable salt or solvate thereof, or a compound of formula (1D), (1E), or (1F) or a solvate thereof, can further comprise a second therapeutic agent in the medicament.

The methods for treating or preventing a Condition in an animal in need thereof can further comprise co-administering to the animal being administered a compound of formula (1), (1A), (1B), or (1C) or a pharmaceutically acceptable salt or solvate thereof, or a compound of formula (1D), (1E), or (1F) or a solvate thereof (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range in view of the present disclosure. A compound of formula (1), (1A), (1B), or (1C) or a pharmaceutically acceptable salt or solvate thereof, or a compound of formula (1D), (1E), or (1F) or a solvate thereof and the second therapeutic agent combined can act either additively or synergistically to treat the same Condition, or they may act independently of each other such that the compound of formula (1), (1A), (1B), or (1C) or a pharmaceutically acceptable salt or solvate thereof, or the compound of formula (1D), (1E), or (1F) or a solvate thereof treats or prevents a Condition and the second therapeutic agent treats or prevents another disorder, which can be the same as or different from the Condition. In one embodiment of the disclosure, where a second therapeutic agent is co-administered to an animal for treatment of a Condition (e.g., a sleep disorder), the minimal effective amount of the compound of formula (1), (1A), (1B), or (1C) or a pharmaceutically acceptable salt or solvate thereof, or the compound of formula (1D), (1E), or (1F) or a solvate thereof can be less than its minimal effective amount would be where the second therapeutic agent is not administered. In this embodiment, the compound of formula (1), (1A), (1B), or (1C) or a pharmaceutically acceptable salt or solvate thereof, or the compound of formula (1D), (1E), or (1F) or a solvate thereof and the second therapeutic agent can act synergistically to treat or prevent a Condition.

In one embodiment, a compound of formula (1), (1A), (1B), or (1C) or a pharmaceutically acceptable salt or solvate thereof, or a compound of formula (1D), (1E), or (1F) or a solvate thereof is administered concurrently with a second therapeutic agent as a single composition comprising an effective amount of a compound of formula (1), (1A), (1B), or (1C) or a pharmaceutically acceptable salt or solvate thereof, or a compound of formula (1D), (1E), or (1F) or a solvate thereof and an effective amount of the second therapeutic agent. Alternatively, a composition comprising an effective amount of a compound of formula (1), (1A), (1B), or (1C) or a pharmaceutically acceptable salt or solvate thereof, or a compound of formula (1D), (1E), or (1F) or a solvate thereof and a second composition comprising an effective amount of the second therapeutic agent are concurrently administered. In another embodiment, an effective amount of a compound of formula (1), (1A), (1B), or (1C) or a pharmaceutically acceptable salt or solvate thereof, or a compound of formula (1D), (1E), or (1F) or a solvate thereof is administered prior or subsequent to administration of an effective amount of the second therapeutic agent. In this embodiment, the compound of formula (1), (1A), (1B), or (1C) or a pharmaceutically acceptable salt or solvate thereof, or the compound of formula (1D), (1E), or (1F) or a solvate thereof is administered while the second therapeutic agent exerts its therapeutic effect, or the second therapeutic agent is administered while the compound of formula (1), (1A), (1B), or (1C) or a pharmaceutically acceptable salt or solvate thereof, or the compound of formula (1D), (1E), or (1F) or a solvate thereof exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a second sedative or hypnotic, a Cox-II inhibitor, a 5-lipoxygenase inhibitor, an anti-emetic, a β-adrenergic blocker, an anticonvulsant, an antidepressant, a $Ca^{2+}$-channel blocker, an anticancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts or solvates thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable salts or solvates thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable salt thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable salt thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman and Gilman's The Pharmacological Basis of Therapeutics* (Goodman et al., eds., $9^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., $19^{th}$ Ed., Mack Publishing, Easton, Pa., 1995), which are hereby incorporated by reference in their entireties.

Examples of useful second sedatives or hypnotics include, but are not limited to, benzodiazepines, including lorazepam, temazepam, and triazolam; barbiturates, including phenobarbital, pentobarbital, and secobarbital; so-called "z-drugs," including zaleplon, zolpidem, and zopiclone; ramelteon; suvorexant; a pharmaceutically acceptable salt thereof, or any mixture thereof.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable salt thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable salt thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable salt thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable salt thereof, or any mixture thereof.

Examples of useful therapeutic agents for treating or preventing UI include, but are not limited to, propantheline, imipramine, hyoscyamine, oxybutynin, dicyclomine, a pharmaceutically acceptable salt thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable salt thereof; or any mixture thereof.

Examples of useful therapeutic agents for treating or preventing diarrhea include, but are not limited to, diphenoxylate, loperamide, a pharmaceutically acceptable salt thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable salt thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable salt thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the disclosure is prepared by a method comprising admixing a compound of formula (1), (1A), (1B), or (1C) or a pharmaceutically acceptable salt or solvate thereof, or a compound of formula (1D), (1E), or (1F) or a solvate thereof, with a pharmaceutically acceptable carrier or excipient. Admixing can be accomplished using methods known for admixing a compound (or derivative) and a pharmaceutically acceptable carrier or excipient. In one embodiment, the compound of formula (1), (1A), (1B), or (1C) or a pharmaceutically acceptable salt or solvate thereof, or the compound of formula (1D), (1E), or (1F) or a solvate thereof is present in the composition in an effective amount.

5.7 Kits

The disclosure further provides kits that can simplify the handling and administration of a compound of formula (1), (1A), (1B), or (1C) or a pharmaceutically acceptable salt or solvate thereof, or a compound of formula (1D), (1E), or (1F) or a solvate thereof to an animal.

A typical kit of the disclosure comprises a unit dosage form of a compound of formula (1), (1A), (1B), or (1C) or a pharmaceutically acceptable salt or solvate thereof, or a compound of formula (1D), (1E), or (1F) or a solvate thereof. In one embodiment, the unit dosage form comprises a first container, which can be sterile, containing an effective amount of a compound of formula (1), (1A), (1B), or (1C) or a pharmaceutically acceptable salt or solvate thereof, or a compound of formula (1D), (1E), or (1F) or a solvate thereof and a pharmaceutically acceptable carrier or excipient. The kit can further comprise a label or printed instructions instructing the use of the compound of formula (1), (1A), (1B), or (1C) or a pharmaceutically acceptable salt or solvate thereof, or the compound of formula (1D), (1E), or (1F) or a solvate thereof to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a compound of formula (1), (1A), (1B), or (1C) or a pharmaceutically acceptable salt or solvate thereof, or a compound of formula (1D), (1E), or (1F) or a solvate thereof, an effective amount of a second therapeutic agent and a pharmaceutically acceptable carrier or excipient. Examples of second therapeutic agents include, but are not limited to, those listed above.

Kits of the disclosure can further comprise a device useful for administering the unit dosage form. Examples of such a device include, but are not limited to, a syringe, a drip bag, a patch, an inhaler, and an enema bag.

5.8 Other Compounds

Other compounds referred to herein include:

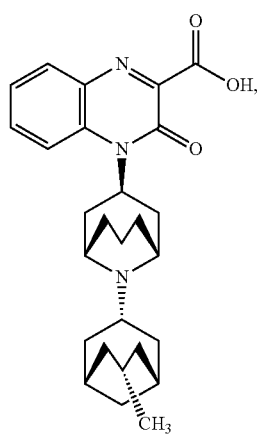

405

-continued

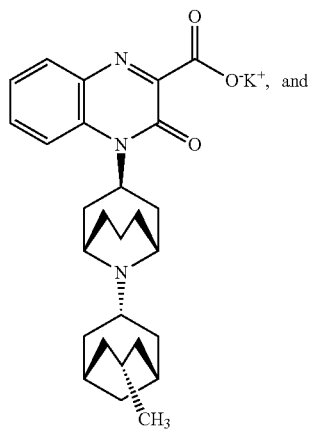

405K

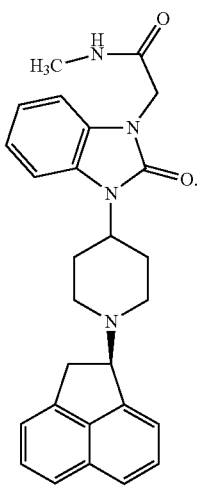

W-212393

The synthesis (Example 9, columns 103-108) and certain pertinent properties (Example 18, columns 116-117) of Compound 405 are disclosed in, inter alia, U.S. Pat. No. 8,476,271, which is hereby incorporated by reference in its entirety. Compound 405K is the mono-potassium salt of Compound 405; it was prepared by a method known to those in the art. The synthesis (Example 18, column 20) and certain properties (Experimental Examples 1-3 and 5, columns 22-22) of Compound W-212393 are disclosed in, inter alia, U.S. Pat. No. 7,566,728, which is hereby incorporated by reference in its entirety. Throughout the examples in this application, the free base, i.e., the non-salt form, of Compound W-212393 was used.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

6. EXAMPLES

Certain Examples below relate to methods for treating or preventing a sleep disorder by administering a compound of formula (1), (1A), (1B), or (1C) or a pharmaceutically acceptable salt or solvate thereof, or a compound of formula (1D), (1E), or (1F) or a solvate thereof to an animal in need of such treatment.

6.1 Example 1: Human Trial Protocol

A phase 1, randomized, double-blind, single-center, crossover, in- and out-patient study assessing the effects of Compound (1D) on sleep efficiency ("SE"), Latency to Persistent Sleep ("LPS"), Wake After Sleep Onset ("WASO"), and Total Sleep Time ("TST") in subjects with insomnia disorder was performed. The study randomized up to about 40 subjects in order to achieve about 24 completers (i.e., subjects who completed both Dosing Periods 1 and 2). The subjects included males and females aged 18 to 60 years, inclusive, with insomnia disorder (as defined by the Diagnostic and Statistical Manual of Mental Disorders, Fifth Edition, American Psychiatric Association Publishing, Arlington, Va. (2013) ("DSM-5")) and who otherwise had no significant medical or psychiatric history.

This study used two consecutive dosing nights of orally administered Compound (1D) or placebo in each of two separate dosing periods (Dosing Periods 1 and 2) that were approximately five days apart during a 10-day-long treatment period. Compound (1D) was administered orally in an aqueous suspension comprising 0.5% w/w methylcellulose (METHOCEL A4C Premium, Dow Chemical Co., Midland, Mich.). A 10 mg dose was achieved by administering from a dosing vial the suspension of Compound (1D) followed by four or more sterile-water irrigation rinses (20 mL per rinse) of the dosing vial and sufficient water to total 240 mL, with each subject dosed 30 minutes before their median habitual bedtime. Placebo to match the Compound (1D) aqueous suspension was orally administered in the same way. The placebo consisted of an aqueous suspension of corn starch (UNI-PURE FL, Ingredion Germany GmbH, Hamburg, Germany) also comprising 0.5% w/w methylcellulose (METHOCEL A4C Premium).

The study consisted of three periods: (1) pre-randomization (up to 28 days), (2) treatment (10 days), and (3) follow-up.

(1) The pre-randomization period protocol consisted of a screening visit followed, for successful subjects, by a baseline visit, each described in more detail as follows.

During a screening visit (Days −28 to −8), vital signs, medical, sleep and psychiatric histories, laboratory test results, pregnancy test results, drug screen results, Colombia-suicide severity rating scale ("C-SSRS") assessment, and an ECG were obtained. If a washout of prohibited medications was required, this washout was completed during the screening. Subjects who successfully completed the screening visit received a sleep-habits diary that was completed for a minimum of seven consecutive days before the baseline visit so that median habitual bedtime could be assessed.

During a baseline visit (Days −7 to −5), subjects arrived at a clinical unit in the afternoon or evening of Day −7. At that time, they began a stay of two consecutive nights during which each subject underwent continuous PSG recording for eight hours on the first night (Night 1) to assess eligibility criteria and to screen out subjects with sleep apnea or periodic limb movements with arousal. Successful subjects underwent another eight hours of continuous PSG recording on the second night (Night 2), which determined if a subject met the sleep-eligibility criteria based on the average of data obtained on Nights 1 and 2 of the baseline period. During the baseline visits, subjects also practiced the psychometric tests used in this study (e.g., digital symbol substitution test ("DSST"), psychomotor vigilance task ("PVT"), and Karolinksa Sleepiness Scale ("KS S")) and familiarized themselves with the profile of mood states-standard ("POMS-standard") and post-sleep questionnaire. To assess a subject's perception of the quality and quantity of sleep, the post-sleep questionnaire asked questions such as "how many minutes did it take you to fall asleep last night after you got into bed and the lights were turned off?", "how many times did you awaken during the night?", and "on a scale from 1 to 10, with 1 being poor and 10 being excellent, how would you rate the quality of your sleep last night?". Subjects who met all eligibility criteria after the baseline visit returned approximately seven days later to enter the treatment period (Dosing Periods 1 and 2).

A summary of the PSG recording procedure that was used is as follows. Standard placements for EEG electrodes were derived according to the international 10-20 system (see, e.g., Jasper, "The ten-twenty electrode system of the international federation," *Electroencephalography Clin. Neurophys.* 10:371-375 (1958)) with the exception of the change of the A1-A2 labels to M1-M2, pursuant to the AASM Manual for Scoring of Sleep (Berry et al., "The AASM Manual for the Scoring of Sleep and Associated Events: Rules, Terminology and Technical Specifications," *Version 2.0.3*, American Academy of Sleep Medicine, Darien, Ill., (2014)). This system requires that electrodes be positioned in measured relationships to landmark anatomical points. Standard placements for EOG, submental EMG electrodes, anterior tibialis EMG electrodes, and airflow sensors were consistent with the AASM Manual for Scoring of Sleep.

Electrodes used for EEG recording were standard gold- or silver-cup electrodes intended for use in EEG recording. These electrodes were approximately 4 to 10 mm. in diameter and were connected to a thin wire having an appropriate connector. Electrodes used for EOG and EMG recordings were self-adhesive electrodes of approximately 12 mm diameter with snap-on connectors that enabled the electrode to be connected to a thin wire having an appropriate connector. Electrodes used for ECG recordings were self-adhesive electrodes of approximately 12 mm. diameter with snap-on connectors that enabled the electrode to be connected to a thin wire having an appropriate connector (e.g., 3M RED DOT electrodes or MEDITRACE electrodes).

Scalp and skin surfaces at points of contact with an electrode were thoroughly cleansed prior to electrode placement by applying a mild abrasive cleanser on both scalp and skin surfaces according to manufacturers' recommendations using a cotton swab. Isopropyl alcohol was used to wipe the abraded surface. A small dab of conductive EEG paste was then applied to the scalp or skin surface and to the cup electrodes. When facial or body hair was present at a desired site, if an insignificant deviation from the required electrode placement was possible an electrode was relocated to an adjacent area, otherwise, the facial or body hair was removed.

The electrical impedance of all EEG, EOG, submental EMG, limb EMG, and ECG electrodes was less than 5 kOhms; electrical impedance was checked prior to the start of recording using a commercially-available impedance meter. Digital PSG systems were calibrated prior to each PSG recording performed 45 minutes prior to "lights-off." Calibration involved the use of internally generated input signals of known voltage, which served as benchmarks against which physiological data were measured and quantified. The digital PSG calibration settings were as follows:

| Channel | Low Frequency Filter (Hz) | High Frequency Filter (Hz) |
|---|---|---|
| EOG | 0.3 | 35 |
| EMG | 10 | 70 to 120 |
| EEG | 0.3 | 35 |
| ECG | 0.3 | 70 |
| Airflow | 0.1 | 15 |

Acquisition of EEG signals occurred at a minimum sampling rate that was approximately three times the high-frequency filter setting. Specifically, the minimum sampling rate for EEGs collected using the high-frequency filter setting specified was at least 100 samples per second, or 100 Hz. No sampling rate greater than 256 Hz was used. The minimum storage rate for all PSG data was 200 Hz.

Biological calibration or "biocalibration" is a procedure in which the subject, in bed and supine, lies awake quietly and performs specific actions or movements in a specified sequence so that the quality of PSG signals may be assessed. Biocalibration was performed 15 minutes before lights-off. However, immediately following the completion of biocalibration procedures, the subject was awake and instructed to sit up to leave a reasonable time for "settling" before lights-off. Subjects were instructed not to move their heads or bodies unnecessarily while biocalibration procedures were performed so that head or body movement did not result in an artifact that obscured a biocalibration signal. Biocalibration procedures were performed on PSG nights according to the following schedule:

| Instruction to Subject | Biocalibration Duration | Nights |
|---|---|---|
| "Rest with your eyes closed" | 30 sec. of artifact-free tracing | All |
| "Rest with your eyes open" | 30 sec. of artifact-free tracing | All |
| "Open your eyes," "close your eyes" | 1 min. (30 sec. each) | All |
| "Open your eyes" | 5 sec. | All |
| "Look up," "look down" | Several times during a 30 sec. period | All |
| "Open your eyes" | 5 sec. | All |
| "Glance to the left," "glance to the right" | Several times during a 30 second period | All |
| "Grit your teeth," "stick out your tongue," "stick out your jaw" | 5 to 10 sec. | All |
| "Breathe in and out through your mouth" | 15 sec. | Screening Nights |
| "Breathe in and out through your nose" | 15 sec. | Screening Nights |
| "Hold your breath" | 5 sec. | Screening Nights |
| "Flex your left toe/leg" | 5 to 10 sec. | Screening Nights |
| "Flex your right toe/leg" | 5 to 10 sec. | Screening Nights |

A PSG "screening montage" of 18 channels of recording displayed in a specific sequence was used for Night 1. A "treatment montage" of 12 channels of recording displayed in a specific sequence was used for Night 2 and treatment nights. The following electrode derivations or positions were eliminated from the screening montage to yield the treatment montage: left anterior tibialis, right anterior tibialis, nasal/oral airflow (thermistor), nasal airflow (nasal pressure transducer), respiratory inductance plethysomography, and respiratory inductance plethysomography.

(2) The 10-day treatment period included two dosing periods (Dosing Periods 1 and 2) that were approximately 5 days apart. Once continued eligibility was confirmed, subjects were randomized as to treatment upon check-in on Day 1. Each of Dosing Period 1 (Days 1 to 3) and Dosing Period 2 (Days 8 to 10) consisted of a stay of two consecutive nights, during which subjects received the same study drug (either Compound (1D) or placebo) on both evenings of that dosing period. The study drug was administered 30 minutes before each subject's median habitual bedtime (to the nearest quarter hour as determined from the sleep diary) in each dosing period according to the study randomization schedule. For all subjects in the study in each study period, urinalysis with microscopy was performed after the first dose and the results assessed before the second dose of study drug was administered. The C-SSRS was also administered upon check-in on Days 1 and 8 and before discharge on Days 3 and 10.

Following the evening-time dosing with study drug, subjects underwent eight hours of continuous PSG recording. Next-day residual effects were assessed by the DSST, KSS, POMS-standard, and the PVT, all of which were collected in the order specified, starting at approximately 30 minutes after "lights-on." All tests (except the POMS-standard, which was administered once at lights-on) were administered in the clinical unit, beginning 30 minutes after lights-on and every 90 minutes thereafter for approximately 16 hours post-lights-off, following PSG recording. Each subject also completed a sleep questionnaire once after lights-on so that subjective impressions could be assessed about the quality and quantity of their sleep. Before the second night dosing in each dosing period, subjects were evaluated for any residual sleepiness. For subjects who exhibited continued sedation, the second night dosing was withheld. Subjects remained in the clinic until residual symptoms were minimized.

Prior to discharge from Dosing Period 1 (Day 3), subjects had a urinalysis with microscopy, chemistry and hematology collected.

A 24-hour urine collection was initiated immediately post-first dose in each dosing period. Blood was collected after the second dose in each period to determine the concentration of drug and, possibly, its metabolites.

(3) A follow-up period (Days 16 to 19) included a telephone call completed 7 to 10 days after the last dose of the study drug to monitor adverse effects and use of concomitant medication/therapy since the previous visit.

6.2 Example 2: Statistical Methods

In general, categorical variables were summarized by the count ("n") and percentage of subjects. Continuous variables were summarized by the number of non-missing observations ("n"), mean, standard deviation ("SD"), standard error of the mean, median, and minimum and maximum values.

The full-analysis population ("FAP") was the group of subjects who were randomized and received one dose of the study drug. Exposure to study drug was presented for each treatment group. The analysis population for efficacy was the FAP.

Efficacy endpoints—The primary efficacy variable was the effects of Compound (1D) on SE as measured by PSG. For the purposes of summary and analysis, the mean SE obtained from PSG was used per subject per treatment. It was derived by taking the mean of SE for Days 1 and 2 per treatment period or baseline. The two PSG nights in each treatment period were averaged before comparison. When data from only one of these days were available, the available data were taken as the measurement for that period. The baseline, post-baseline, and change of baseline of SE were summarized by treatment group by using descriptive statistics. The statistical analysis to compare Compound (1D) versus placebo was performed by using a mixed model approach that included period, sequence, and treatment as fixed effects, subject within the sequence as random effect, and the baseline measurement of SE as a covariate. The 2-sided significance level of 0.05 was used for comparison.

Subjects underwent eight hours of PSG recording, and PSGs were collected and scored by a central reader. Sleep stages were scored following AASM standard criteria based on 30-second epochs. Polysomnography parameters, including LPS, REM latency, NAW, TST, WASO, and total minutes of Stages of N1, N2, N3, and REM were compared between the two treatment periods (Compound (1D) versus placebo). Sleep quality and depth of sleep as measured by the post-sleep questionnaire were also compared between the two treatment periods (Compound (1D) versus placebo).

The baseline, post-baseline, and change from baseline of WASO were summarized by treatment group by using descriptive statistics. The analysis was performed by using a mixed model approach that included period, sequence, and treatment as fixed effects, subject within sequence as random effect, and the baseline measurement of WASO as covariate.

Other secondary variables (LPS; TST; total minutes of Stages of N1, N2, N3, and REM; REM latency; NAW as measured by PSG; and sleep quality and depth of sleep as measured by the post-sleep questionnaire) were summarized and analyzed as detailed above for the WASO parameter. The next-day residual effects parameters, measured by DSST, KSS, POMS-standard, and PVT, were summarized using descriptive statistics.

Missing data handling—For analyses of change from baseline, baseline was generally defined as the pre-dose assessment on Day −6 or earlier as scheduled. If this value was unavailable, the last non-missing value before dosing was used. Otherwise, missing observations were treated as missing at random, and no data imputation was performed.

Sample size determination—Rationale to support the sample size estimation was derived from results of a PSG study published by Scharf et al. ("A multicenter, placebo-controlled study evaluating zolpidem in the treatment of chronic insomnia," *J. Clin. Psychiatry* 55(5):192-199 (1994)). Mean percent SE for the low dose of 10 mg zolpidem group, as measured by PSG in chronic insomniacs, was typically 7% higher than for the placebo group, representing an increase of 25 to 40 minutes. Moreover, in the publication of Roth et al. ("A 2-night, 3-period, crossover study of ramelteon's efficacy and safety in older adults with chronic insomnia," *Curr. Med. Res. Opin.* 23(5):1005-1014 (2007)), the SD of the differences between active and placebo was approximately 9. In the absence of pre-existing information on the ORL-1 active dose for SE, in this study a SD of 10 was used as a conservative estimate of dispersion.

Safety—Subjects' adverse effects ("AEs") were categorized into preferred terms and associated system organ class ("SOC") using the *Medical Dictionary for Regulatory Activities* ("MedDRA", version 16.1). Treatment-emergent AEs ("TEAEs") were defined as AEs that start after or increase in severity after the first dose of study drug. An AE occurring after the first dose of study drug was considered to be a TEAE and was assigned to the most recent treatment administered. Treatment-emergent AEs were summarized by presenting the incidence of AEs for each treatment group by the MedDRA preferred term, nested within SOC for the safety population.

6.3 Example 3: Sleep Efficiency Results

The full SE data set obtained for each of the periods described in Examples 1 and 2 above is provided above the double line in Table 1 below; a compilation and analysis for screening and treatment appears below the double line in Table 1.

TABLE 1

Summary of Sleep Efficiency ("SE") During 8 Hours Post-Dose per Night (Full Analysis Population)

| | Placebo (N = 21) | Compound (1D) (N = 19) | Overall (N = 22) |
|---|---|---|---|
| *Screening Period (Baseline) Night 1* | | | |
| n | | | 22 |
| Mean (SD) | | | 71.67 (13.899) |
| Median | | | 77.60 |
| Minimum, Maximum | | | 32.5, 87.7 |
| *Screening Period (Baseline) Night 2* | | | |
| n | | | 22 |
| Mean (SD) | | | 78.84 (7.316) |
| Median | | | 79.12 |
| Minimum, Maximum | | | 63.0, 90.2 |
| *Treatment Period 1 Night 1* | | | |
| n | 11 | 11 | 22 |
| Mean (SD) | 80.12 (10.828) | 88.33 (6.777) | 84.23 (9.786) |
| Median | 81.25 | 87.40 | 86.30 |
| Minimum, Maximum | 60.2, 92.2 | 74.7, 97.7 | 60.2, 97.7 |
| *Treatment Period 1 Night 2* | | | |
| n | 10 | 11 | 21 |
| Mean (SD) | 84.45 (7.020) | 91.63 (4.078) | 88.21 (6.633) |
| Median | 86.41 | 92.29 | 91.25 |
| Minimum, Maximum | 70.2, 93.4 | 80.7, 95.6 | 70.2, 95.6 |
| *Treatment Period 2 Night 1* | | | |
| n | 10 | 8 | 18 |
| Mean (SD) | 75.58 (14.615) | 93.56 (2.488) | 83.57 (14.147) |
| Median | 77.08 | 94.38 | 88.37 |
| Minimum, Maximum | 39.7, 90.0 | 88.3, 95.5 | 39.7, 95.5 |
| *Treatment Period 2 Night 2* | | | |
| n | 10 | 8 | 18 |
| Mean (SD) | 80.73 (5.727) | 93.23 (1.790) | 86.28 (7.716) |
| Median | 81.25 | 93.80 | 87.24 |
| Minimum, Maximum | 67.1, 88.9 | 90.8, 95.7 | 87.1, 95.7 |
| *Screening Period Mean (Baseline)* | | | |
| n | | | 22 |
| Mean (SD) | | | 75.258 (8.5767) |
| Median | | | 76.745 |
| Minimum, Maximum | | | 47.76, 87.24 |
| *Treatment Period Mean* | | | |
| n | 21 | 19 | 22 |
| Mean (SD) | 79.751 (9.5037) | 91.419 (3.8701) | 85.294 (9.3835) |
| LSM (STDE) | 79.74 (1.492) | 91.53 (1.588) | N/A |
| Median | 83.178 | 92.396 | 86.432 |
| Minimum, Maximum | 53.39, 91.72 | 81.72, 96.67 | 53.39, 96.67 |
| *Change from Baseline* | | | |
| n | 21 | 19 | 22 |
| Mean (SD) | 4.488 (9.0922) | 15.986 (7.9225) | 9.950 (10.2554) |
| LSM (STDE) | 4.40 (1.492) | 16.18 (1.588) | N/A |
| Median | 5.469 | 15.365 | 9.427 |
| Minimum, Maximum | −11.46, 26.93 | 2.60, 41.25 | 11.46, 41.25 |
| *Statistical Testing* | | | |
| Drug Effect Difference (LSM (STDE)) | | 11.79 (2.180) | |
| 95% Confidence Interval | | (7.17, 16.41) | |
| P-value | | 0.0000581 | |

Table 2 below summarizes the results of the SE determinations; the bar chart in FIG. 1 provides a graphical representation of SE wherein the "average" bar represents the average of assessment on Night 1 and Night 2 of each study period.

TABLE 2

Results of SE Determinations

| Sleep Efficiency (SE, %) | Placebo (N = 21) | Compound (1D) (N = 19) |
|---|---|---|
| Mean Baseline (SD) | 75.3 (8.8) | 75.4 (8.7) |
| Treatment Period Mean (SD) | 79.8 (9.5) | 91.4 (3.9) |
| LSM Change from Baseline (STDE) | 4.4 (1.5) | 16.2 (1.6) |
| LSM Effect Difference (STDE) | — | 11.8 (2.2) |
| P-value | — | <0.001 |

As is evident from the data in FIG. 1 and Table 2, Sleep Efficiency, the primary efficacy variable, was significantly increased in the treatment group, exhibiting a LSM increase effect of 11.8 minutes.

6.4 Example 4: Latency to Persistent Sleep Results

The full LPS data set obtained for each of the periods described in Examples 1 and 2 above is provided above the double line in Table 3 below; a compilation and analysis for screening and treatment appears below the double line in Table 3.

TABLE 3

Summary of Latency to Persistent Sleep ("LPS") in Minutes per Night (Full Analysis Population)

| | Placebo (N = 21) | Compound (1D) (N = 19) | Overall (N = 22) |
|---|---|---|---|
| Screening Period (Baseline) Night 1 | | | |
| n | | | 22 |
| Mean (SD) | | | 52.43 (42.691) |
| Median | | | 41.00 |
| Minimum, Maximum | | | 15.0, 218.5 |
| Screening Period (Baseline) Night 2 | | | |
| n | | | 22 |
| Mean (SD) | | | 49.18 (32.649) |
| Median | | | 38.75 |
| Minimum, Maximum | | | 18.0, 142.5 |
| Treatment Period 1 Night 1 | | | |
| n | 11 | 11 | 22 |
| Mean (SD) | 36.00 (31.470) | 25.68 (15.691) | 30.84 (24.834) |
| Median | 26.50 | 24.50 | 25.00 |
| Minimum, Maximum | 8.0, 113.0 | 6.0, 58.0 | 6.0, 113.0 |
| Treatment Period 1 Night 2 | | | |
| n | 10 | 11 | 21 |
| Mean (SD) | 23.75 (15.203) | 20.73 (29.755) | 22.17 (23.433) |
| Median | 18.50 | 15.00 | 15.00 |
| Minimum, Maximum | 0.0, 47.0 | 0.0, 105.0 | 0.0, 105.0 |
| Treatment Period 2 Night 1 | | | |
| n | 10 | 8 | 18 |
| Mean (SD) | 44.95 (37.753) | 12.75 (14.425) | 30.64 (33.336) |
| Median | 28.00 | 9.00 | 16.75 |
| Minimum, Maximum | 11.0, 119.5 | 0.0, 46.0 | 0.0, 119.5 |
| Treatment Period 2 Night 2 | | | |
| n | 10 | 8 | 18 |
| Mean (SD) | 38.50 (23.287) | 12.50 (9.350) | 26.94 (22.357) |
| Median | 33.00 | 11.50 | 20.00 |
| Minimum, Maximum | 5.5, 70.0 | 0.5, 29.5 | 0.5, 70.0 |
| Screening Period Mean (Baseline) | | | |
| n | | | 22 |
| Mean (SD) | | | 50.807 (27.4393) |
| Median | | | 41.875 |
| Minimum, Maximum | | | 20.75, 125.25 |
| Treatment Period Mean | | | |
| n | 21 | 19 | 22 |
| Mean (SD) | 35.488 (22.6018) | 18.750 (15.6310) | 27.538 (21.4775) |
| LSM (STDE) | 35.58 (4.305) | 18.14 (4.579) | N/A |
| Median | 28.500 | 15.000 | 21.125 |
| Minimum, Maximum | 8.25, 78.25 | 2.00, 70.25 | 2.00, 78.25 |

TABLE 3-continued

Summary of Latency to Persistent Sleep ("LPS") in Minutes per Night (Full Analysis Population)

|  | Placebo (N = 21) | Compound (1D) (N = 19) | Overall (N = 22) |
| --- | --- | --- | --- |
| Change from Baseline | | | |
| n | 21 | 19 | 22 |
| Mean (SD) | −16.610 (34.7399) | −29.918 (23.3435) | −22.931 (30.2606) |
| LSM (STDE) | −14.89 (4.306) | −32.33 (4.580) | N/A |
| Median | −17.500 | −27.250 | −23.025 |
| Minimum, Maximum | −102.75, 49.25 | −87.75, 8.75 | −102.75, 49.25 |
| Statistical Testing | | | |
| Drug Effect Difference (LSM (STDE)) | | −17.44 (6.292) | |
| 95% Confidence Interval | | (−30.77, −4.10) | |
| P-value | | 0.0136 | |

Figure 2:
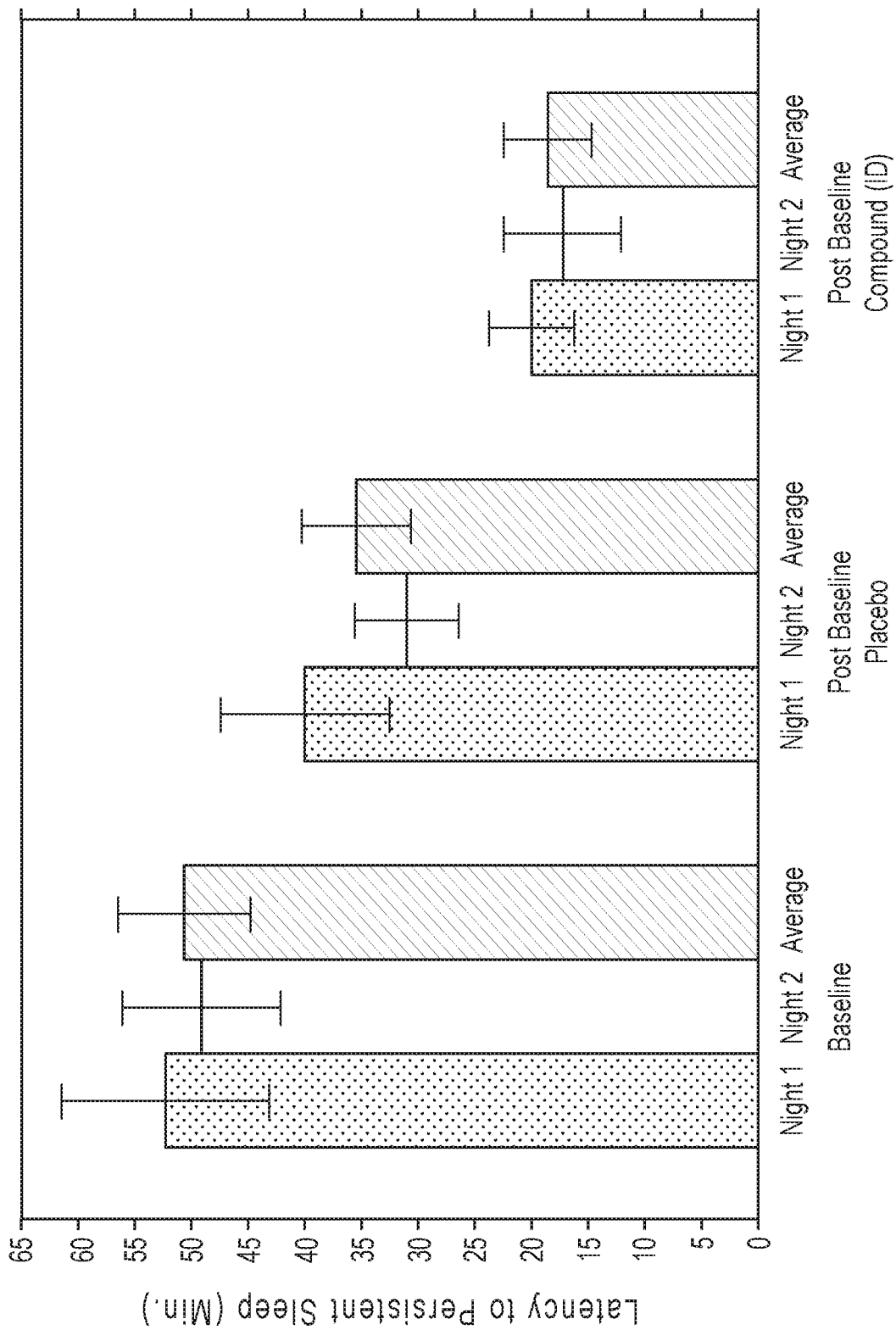
FIG. 2 shows a bar chart summarizing the human Latency to Persistent Sleep ("LPS") results in Example 4 for the full analysis population with the standard error bars as indicated.

Table 4 below summarizes the results of the LPS determinations; the bar chart in FIG. 2 provides a graphical representation of LPS wherein the "average" bar represents the average of assessment on Night 1 and Night 2 of each study period.

TABLE 4

Results of LPS Determinations

| Latency to Persistent Sleep (LPS, min.) | Placebo (N = 21) | Compound (1D) (N = 19) |
| --- | --- | --- |
| Mean Baseline (SD) | 52.1 (27.4) | 48.7 (23.0) |
| Treatment Period Mean (SD) | 35.5 (22.6) | 18.8 (15.6)) |
| LSM Change from Baseline (STDE) | −14.9 (4.3) | −32.3 (4.6) |
| LSM Effect Difference ( STDE) | — | −17.4 (6.3) |
| P-value | — | 0.0136 |

As is evident from the data in FIG. 2 and Table 4, Latency to Persistent Sleep, a secondary efficacy variable, was significantly reduced in the treatment group, exhibiting a LSM decrease effect of 17.4 minutes.

6.5 Example 5: Wake After Sleep Onset Results

The full WASO data set obtained for each of the periods described in Examples 1 and 2 above is provided above the double line in Table 5 below; a compilation and analysis for screening and treatment appears below the double line in Table 5.

TABLE 5

Summary of Wake After Sleep Onset ("WASO") in Minutes per Night (Full Analysis Population)

|  | Placebo (N = 21) | Compound (1D) (N = 19) | Overall (N = 22) |
| --- | --- | --- | --- |
| Screening Period (Baseline) Night 1 | | | |
| n | | | 22 |
| Mean (SD) | | | 91.59 (65.222) |
| Median | | | 67.25 |
| Minimum, Maximum | | | 28.5, 306.0 |
| Screening Period (Baseline) Night 2 | | | |
| n | | | 22 |
| Mean (SD) | | | 59.50 (32.539) |
| Median | | | 52.00 |
| Minimum, Maximum | | | 19.0, 161.0 |
| Treatment Period 1 Night 1 | | | |
| n | 11 | 11 | 22 |
| Mean (SD) | 59.27 (27.021) | 35.95 (29.815) | 47.61 (30.222) |
| Median | 59.00 | 29.50 | 41.50 |
| Minimum, Maximum | 18.0, 104.5 | 7.5, 111.5 | 7.5, 111.5 |
| Treatment Period 1 Night 2 | | | |
| n | 10 | 11 | 21 |
| Mean (SD) | 55.75 (28.412) | 25.68 (12.515) | 40.00 (26.045) |
| Median | 50.75 | 25.50 | 30.00 |
| Minimum, Maximum | 23.5, 106.5 | 4.0, 52.0 | 4.0, 106.5 |

TABLE 5-continued

Summary of Wake After Sleep Onset ("WASO") in Minutes per Night (Full Analysis Population)

|  | Placebo (N = 21) | Compound (1D) (N = 19) | Overall (N = 22) |
|---|---|---|---|
| Treatment Period 2 Night 1 | | | |
| n | 10 | 8 | 18 |
| Mean (SD) | 79.70 (58.140) | 15.63 (4.299) | 51.22 (53.577) |
| Median | 55.75 | 15.75 | 31.00 |
| Minimum, Maximum | 30.0, 206.5 | 9.5, 22.5 | 9.5, 206.5 |
| Treatment Period 2 Night 2 | | | |
| n | 10 | 8 | 18 |
| Mean (SD) | 58.20 (39.398) | 23.44 (8.946) | 42.75 (34.215) |
| Median | 48.25 | 22.75 | 29.75 |
| Minimum, Maximum | 16.0, 140.5 | 12.5, 38.5 | 12.5, 140.5 |
| Screening Period Mean (Baseline) | | | |
| n | | | 22 |
| Mean (SD) | | | 75.545 (44.3455) |
| Median | | | 67.750 |
| Minimum, Maximum | | | 26.75, 233.50 |
| Treatment Period Mean | | | |
| n | 21 | 19 | 22 |
| Mean (SD) | 63.262 (36.0320) | 26.066 (16.2181) | 45.594 (33.7796) |
| LSM (STDE) | 53.74 (5.633) | 25.28 (5.990) | N/A |
| Median | 56.750 | 22.250 | 32.000 |
| Minimum, Maximum | 22.75, 173.50 | 11.00, 51.75 | 11.00, 173.50 |
| Change from Baseline | | | |
| n | 21 | 19 | 22 |
| Mean (SD) | −10.898 (36.4550) | −50.545 (42.1544) | −29.730 (43.6316) |
| LSM (STDE) | −11.58 (5.633) | −50.04 (5.990) | N/A |
| Median | −14.000 | −47.250 | −24.375 |
| Minimum, Maximum | −89.50, 54.50 | −185.50, 29.50 | −185.50, 54.50 |
| Statistical Testing | | | |
| Drug Effect Difference (LSM (STDE)) | | −38.46 (8.222) | |
| 95% Confidence Interval | | (−55.89, −21.03) | |
| P-value | | 0.0003 | |

Figure 3:
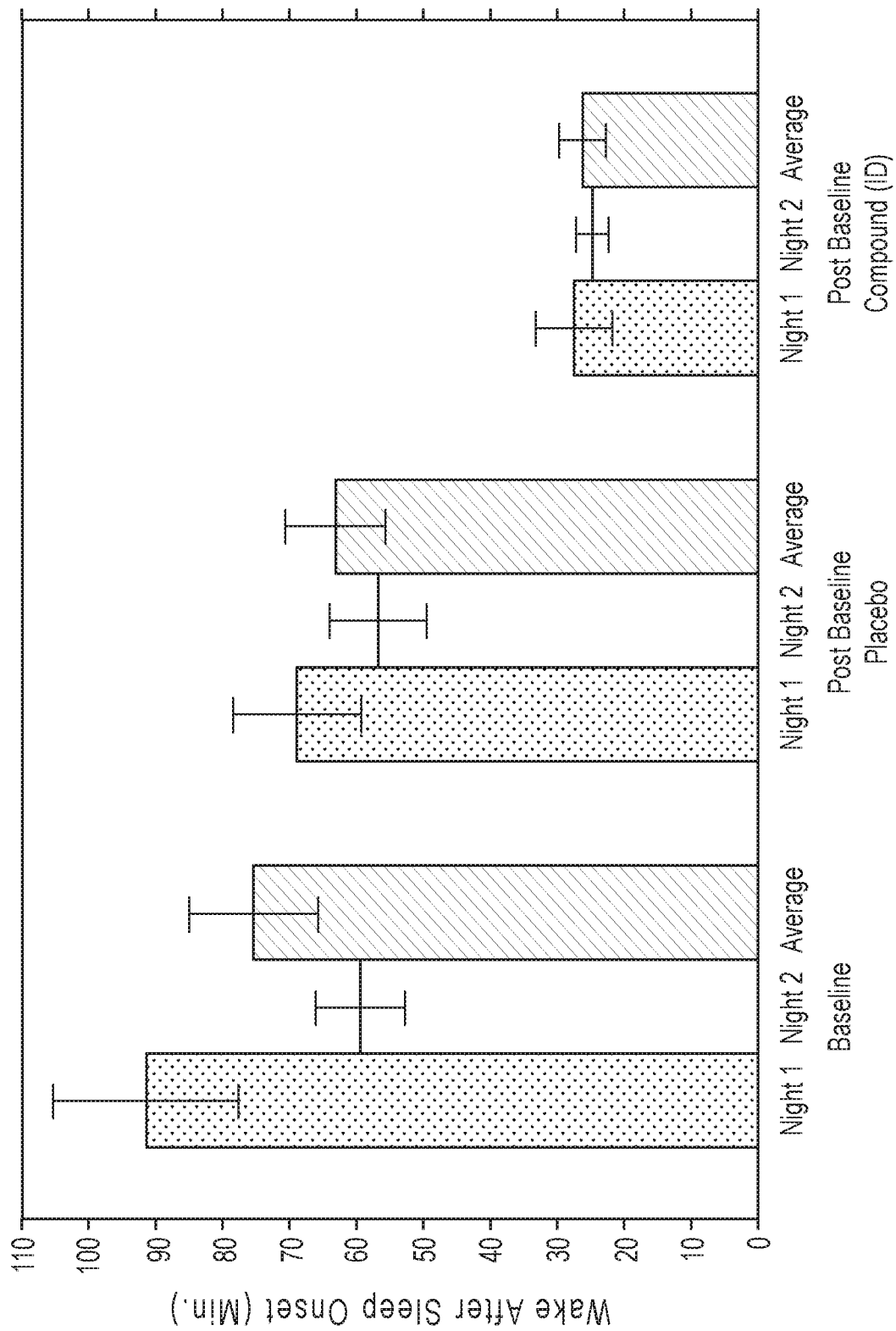
FIG. 3 shows a bar chart summarizing the human Wake After Sleep Onset ("WASO") results in Example 5 for the full analysis population with the standard error bars as indicated.

Table 6 below summarizes the results of the WASO determinations; the bar chart in FIG. 3 provides a graphical representation of WASO wherein the "average" bar represents the average of assessment on Night 1 and Night 2 of each study period.

TABLE 6

Results of WASO Determinations

| Wake After Sleep Onset (WASO, min.) | Placebo (N = 21) | Compound (1D) (N = 19) |
|---|---|---|
| Mean Baseline (SD) | 74.2 (44.9) | 76.6. (43.2) |
| Treatment Period Mean (SD) | 63.3 (36.0) | 26.1 (16.2) |
| LSM Change from Baseline (STDE) | −11.6 (5.6) | −50.0 (6.0) |
| LSM Effect Difference (STDE) | — | −38.5 (8.2) |
| P-value | — | 0.0003 |

As is evident from the data in FIG. 3 and Table 6, Wake After Sleep Onset, a secondary efficacy variable, was significantly reduced in the treatment group, exhibiting a LSM decrease effect of 38.5 minutes.

6.6 Example 6: Total Sleep Time Results

The full TST data set obtained for each of the periods described in Examples 1 and 2 above is provided above the double line in Table 7 below; a compilation and analysis for screening and treatment appears below the double line in Table 7.

TABLE 7

| Summary of Total Sleep Time ("TST") in Minutes per Night (Full Analysis Population) | | | |
|---|---|---|---|
| | Placebo (N = 21) | Compound (1D) (N = 19) | Overall (N = 22) |
| Screening Period (Baseline) Night 1 | | | |
| n | | | 22 |
| Mean (SD) | | | 344.02 (66.717) |
| Median | | | 372.50 |
| Minimum, Maximum | | | 156.0, 421.0 |
| Screening Period (Baseline) Night 2 | | | |
| n | | | 22 |
| Mean (SD) | | | 378.45 (35.119) |
| Median | | | 379.75 |
| Minimum, Maximum | | | 302.5, 433.0 |
| Treatment Period 1 Night 1 | | | |
| n | 11 | 11 | 22 |
| Mean (SD) | 369.73 (90.385) | 424.00 (32.530) | 396.86 (71.872) |
| Median | 390.00 | 419.50 | 414.25 |
| Minimum, Maximum | 128.0, 442.5 | 358.5, 469.0 | 128.0, 469.00 |
| Treatment Period 1 Night 2 | | | |
| n | 10 | 11 | 21 |
| Mean (SD) | 405.35 (33.696) | 439.82 (19.572) | 423.40 (31.838) |
| Median | 414.75 | 443.00 | 438.00 |
| Minimum, Maximum | 337.0, 448.5 | 387.5, 459.0 | 337.0, 459.0 |
| Treatment Period 2 Night 1 | | | |
| n | 10 | 8 | 18 |
| Mean (SD) | 362.80 (70.150) | 416.88 (101.558) | 386.83 (87.274) |
| Median | 370.00 | 453.00 | 418.75 |
| Minimum, Maximum | 190.5, 432.0 | 166.0, 458.5 | 166.0, 458.5 |
| Treatment Period 2 Night 2 | | | |
| n | 10 | 8 | 18 |
| Mean (SD) | 387.50 (27.488) | 447.50 (8.594) | 414.17 (37.035) |
| Median | 390.00 | 450.25 | 418.75 |
| Minimum, Maximum | 322.0, 426.5 | 436.0, 459.5 | 322.0, 459.5 |
| Screening Period Mean (Baseline) | | | |
| n | | | 22 |
| Mean (SD) | | | 361.239 (41.1681) |
| Median | | | 368.375 |
| Minimum, Maximum | | | 229.25, 418.75 |
| Treatment Period Mean | | | |
| n | 21 | 19 | 22 |
| Mean (SD) | 375.036 (69.6000) | 432.026 (35.1088) | 402.106 (62.3202) |
| LSM (STDE) | 375.40 (12.094) | 431.09 (12.869) | N/A |
| Median | 399.250 | 443.500 | 414.125 |
| Minimum, Maximum | 128.00, 440.25 | 309.00, 464.00 | 128.00, 464.00 |
| Change from Baseline | | | |
| n | 21 | 19 | 22 |
| Mean (SD) | 13.776 (66.2278) | 69.955 (49.2950) | 40.461 (64.6379) |
| LSM (STDE) | 13.75 (12.095) | 69.44 (12.870) | N/A |
| Median | 26.250 | 73.750 | 44.125 |
| Minimum, Maximum | −216.00, 129.25 | −59.80, 198.00 | −216.00, 198.00 |
| Statistical Testing | | | |
| Drug Effect Difference (LSM (STDE)) | | 56.69 (17.665) | |
| 95% Confidence Interval | | (18.04, 93.34) | |
| P-value | | 0.0066 | |

Figure 4:
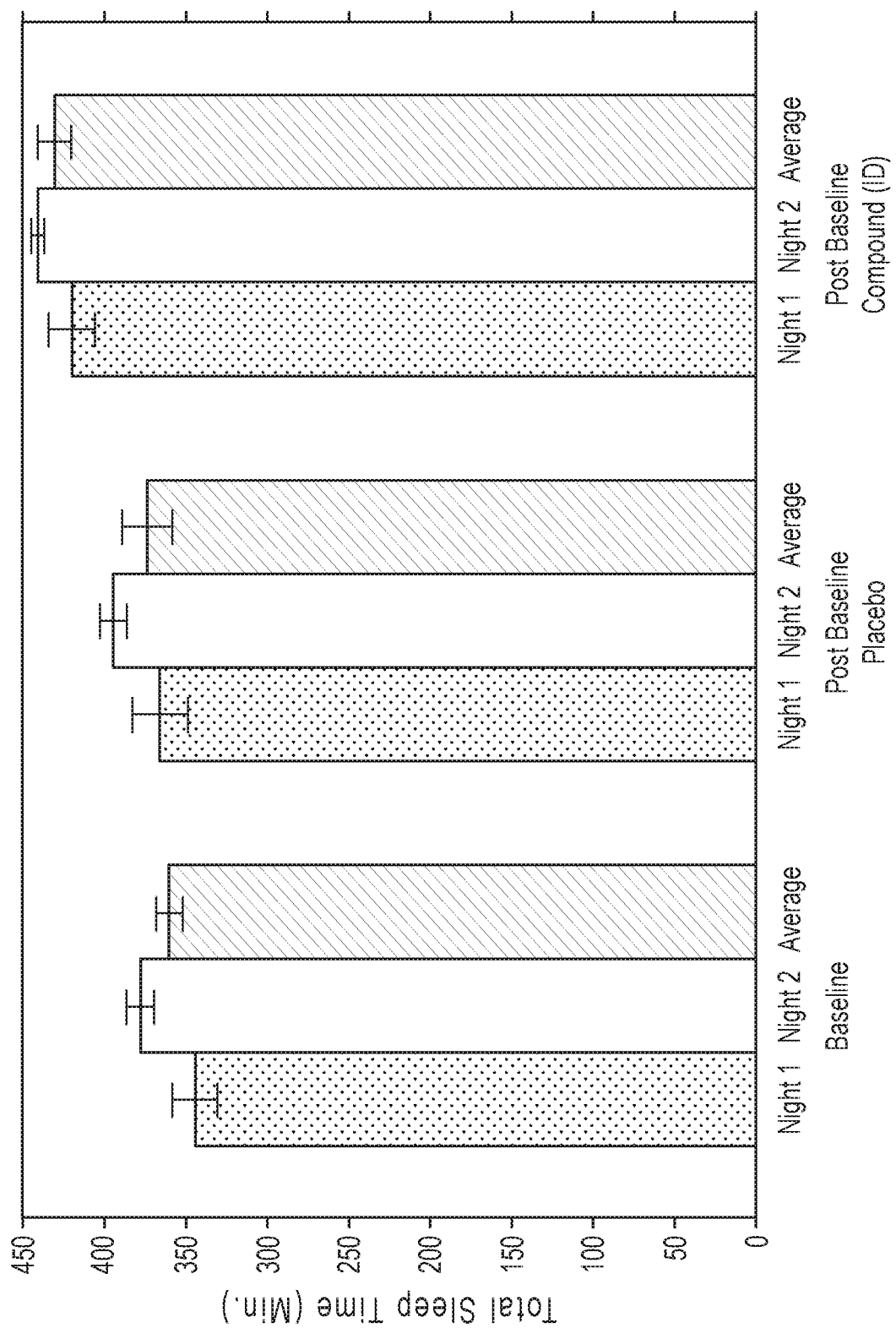
FIG. 4 shows a bar chart summarizing the human Total Sleep Time ("TST") results in Example 6 for the full analysis population with the standard error bars as indicated.

Table 8 below summarizes the results of the TST determinations; the bar chart in FIG. 4 provides a graphical representation of TST wherein the "average" bar represents the average of assessment on Night 1 and Night 2 of each study period.

TABLE 8

Results of TST Determinations

| Total Sleep Time (TST, min.) | Placebo (N = 21) | Compound (1D) (N = 19) |
|---|---|---|
| Mean Baseline (SD) | 361.3 (42.2) | 362.1 (41.7) |
| Treatment Period Mean (SD) | 375.0 (69.6) | 432.0 (35.1) |
| LSM Change from Baseline (STDE) | 13.8 (12.1) | 69.4 (12.9) |
| LSM Effect Difference (STDE) | — | 56.7 (17.7) |
| P-value | — | 0.0066 |

As is evident from the data in FIG. 4 and Table 8, Total Sleep Time, a secondary efficacy variable, was significantly increased in the treatment group, exhibiting a TST increase effect of nearly an hour: 56.7 minutes.

6.7 Example 7: In Vitro Assay of the Solubility of Compounds (1F), 405K, and W-212393

Aqueous solubility of compounds is often a desirable feature. For example, aqueous solubility of a compound permits that compound to be more easily formulated into a variety of dosage forms that may be administered to an animal. When a compound is not fully soluble in the blood, it may precipitate from the blood, and the animal's exposure to the drug will accordingly not correspond to the administered dose. Aqueous solubility increases the likelihood that a compound will not precipitate in an animal's blood, and increases the ability to predict exposure at the target sight of the compound.

A first procedure by which the solubility was determined was as follows. The compound was dissolved in dimethyl sulfoxide to provide a 10 mM test compound in DMSO stock solution. To each of 32 wells, containing a miniature magnetic stirrer, of a 96-well v-bottom plate (0.5 mL/well) was added 400 µL of Japanese Pharmacopoeia Disintegration Test solution number 2 ("JP2") having a pH of about 6.8. 4 µL of test compound stock solution was added to each well, the plate placed on a plate stirrer, and the solutions were allowed to mix for about 16 hours at a temperature of about 25° C. The solutions from all wells were then transferred to the corresponding wells of a new plate having no stirrers. The new plate was centrifuged at a temperature of about 25° C. for 10 minutes at 1,200 relative centrifugal force.

A sample plate was prepared as follows. A 50 µL portion of the compound/JP2 supernatant from each new plate well was transferred to a corresponding well of a shallow-96-well, v-bottom LC-MS sample plate. Another 150 µL portion of the compound/JP2 supernatant from each new plate well was transferred to a corresponding well of a polycarbonate filter plate (Millipore MSSLBPC10), filtered using a Millipore vacuum manifold, and the filtrate collected in a shallow-well receiver plate. 50 µL of filtrate from each receiver plate well was transferred to a corresponding well of the LC-MS sample plate. To each sample plate well was added 50 µL of HPLC grade methanol, the solutions were mixed, and the wells were sealed with septa.

A LC-MS reference plate was also prepared with multiple wells containing 1 µL of a solution of 10 mM of each compound in DMSO serially diluted with 500 µL of methanol then 500 µL of water.

10 µL of a compound solution from each sample plate well was injected into the LC-MS apparatus having a uv-detector and the peak area of peaks at 282 nm (30 nm width), 244 nm (20 nm width), and 223 nm (6 nm width) was obtained. 5 µL of the reference standard for that test compound was also injected and the areas of the same peaks obtained. The MS portion of the apparatus was used to ensure that the correct peak was analyzed. From multiple sample and reference determinations, the average compound's solution concentration was calculated for each peak wavelength and then the results at all wavelengths were averaged to provide the tabulated final solubility result.

A second procedure by which the solubility of each compound was determined was as described above except 50 mM of phosphate buffer with a pH of 6.8 replaced JP2, the centrifugation was omitted and, after the completion of stirring, the entire contents of each well was filtered then diluted with twice the volume of methanol. Analysis was by HPLC with uv detection at the three peaks described above. From the peak areas determined, the average compound's solution concentration was calculated for each peak wavelength and the results at all wavelengths were averaged. 10 µM test compound reference standards were made in triplicate and the areas determined for each wavelength were averaged. The tested compound solubility was calculated as follows:

$$\text{Solubility}\,(\mu M) = 2 \times (\text{Avg. area of test compound}) \times \frac{10\,\mu M}{\text{Avg. area of standard}}. \qquad \text{(Eq. 1)}$$

Table 9 below summarizes the results of the solubility determinations for Compound (1F), Compound 405K, and the free base of Compound W-212393. The results from two separate determinations, by each of the above-described methods respectively, are presented for Compounds (1F) and 405K.

TABLE 9

Results of Solubility Determinations

| | Compound (1F) | Compound 405K | Compound W-212393 |
|---|---|---|---|
| Solubility (µM) at pH 6.8 | >50, 35 | 8, 5 | 42 |

Compound (1F) was highly soluble in aqueous solution. For example, at a pH of about 6.8 Compound (1F) had an aqueous solubility of at least 35 µM. In contrast, Compound 405K had a relatively low aqueous solubility at a pH of about 6.8, averaging about 6.5 µM. Its aqueous solubility at this pH was, at most, about 0.19 of the solubility of Compound (1F) [6.5/35=0.19, 6.5/50=0.13].

6.8 Example 8: In Vitro Assay of Metabolic Stability of Compounds (1F), 405K, and W-212393

The comparative in vitro metabolic stabilities of Compounds (1F), 405K, and W-212393 were determined upon exposure to human liver microsomes or rat liver microsomes according to a procedure disclosed in, e.g., Example 14 of U.S. Pat. No. 9,290,488, which is hereby incorporated by reference in its entirety. Liver microsomes from Crj;CD rats or humans were incubated with 2 µM of each tested compound; thereafter, the supernatant was analyzed by HPLC-MS for the concentration of the tested compound present.

Human liver microsomes, pooled, 20 mg/mL, were obtained from XenoTech LLC (Lexena, Kans., cat #H0610). Rat liver microsomes were obtained from 8-week-old Crj:CD (SD) male rats. Alternatively and if desired, rat liver microsomes can be obtained commercially from, e.g., Xeno-Tech (Sprague-Dawley rat liver microsomes, pooled, 20 mg/mL, cat #R1000). β-NADPH (β-nicotinamide adenine dinucleotide 2'-phosphate reduced tetrasodium salt hydrate) was obtained from Oriental Yeast Co., Ltd. (Tokyo, Japan).

Each tested compound, present at an initial concentration of 2 µM, was incubated at 37° C. in the presence of 0.5 mg/mL of either human microsomes or rat microsomes in suspension in 50 mM Tris-HCl buffer (7.4 pH), 150 mM KCl, 10 mM $MgCl_2$, and 1 mM 13-NADPH. Incubation was initiated upon the addition of a 100-fold concentrated solution of the tested compound to one of the microsome preparations. Incubation was terminated by addition of a two-fold volume of a 1/1 mixture of acetonitrile/methanol after either 0 minutes or 30 minutes of incubation at 37° C. Thereafter, proteins and other macromolecules from the microsome preparation were removed by centrifugation. All incubations were conducted in duplicate.

The mean tested compound concentration was determined after 0 minutes or 30 minutes of incubation using an HPLC-MS apparatus. The HPLC system consisted of a Waters 2795 separations module (Waters Corp., Milford, Mass.) equipped with an inline degasser, temperature controlled auto-sampler, and column oven. The analytical column was a Waters ATLANTIS C18 3.5 µm, 2.1 mm×20 mm column. The mass analyzer was a Waters ZQ, single quadrupole mass spectrometer equipped with an electrospray ionization source operating in the positive ionization mode and utilizing a stainless steel spray capillary.

A 5 µL volume of the supernatant obtained after each incubation was injected into the above-described reverse-phase column maintained at a temperature of about 25° C. and eluted using a solvent gradient (solvent A is 0.1% aqueous formic acid, solvent B is acetonitrile). The HPLC elution conditions were as follows: 5% of solvent B (with the balance solvent A); followed by a linear gradient to 90% of solvent B in 0.1 minutes; followed by 90% of solvent B for 2.9 minutes; followed by a gradient to 5% of solvent B in 0.1 minutes. The column was then equilibrated with 5%/95% of solvent B/solvent A for 1.5 minutes before the next injection. The flow rate was kept constant at 0.4 mL/min. The MS was operated in the selected ion recording mode. The capillary energy and cone energy were 1.5-2.5 kV and 20-40 V, respectively.

The percentage of tested compound remaining after 30 minutes of incubation in the presence of either human liver microsomes or rat liver microsomes was calculated from the determinations of the mean tested compound concentrations after 0 minutes and 30 minutes of incubation.

Table 10 below summarizes the results of the metabolic stability determinations for Compounds (1F), 405K, and W-212393.

TABLE 10

Results of Metabolic Stability Determinations

| | Compound (1F) | Compound 405K | Compound W-212393 |
|---|---|---|---|
| Human Metabolic Stability (%) | 98.7 | 95.1 | 27.3 |
| Rat Metabolic Stability (%) | 95.3 | 96.9 | 58.4 |

As can be noted from the results in Table 10, the metabolic stability of Compound W-212393 upon exposure to either one of the sources of liver microsomes was significantly below 100% (i.e., the value for unmetabolized compound). For example, the metabolic stability of Compound W-212393 upon exposure to human liver microsomes, i.e., the amount of the compound remaining after 30 minutes of incubation relative to the initial amount present after 0 minutes of incubation (expressed as a percentage of the initial amount) was only 27.3%. In contrast, the metabolic stability of Compound (1F) upon exposure to human liver microsomes was much greater, 98.7%, or about 3.6 times greater (98.7%/27.3%). In another example, the metabolic stability of Compound W-212393 upon exposure to rat liver microsomes was only 58.4%. In contrast, the metabolic stability of Compound (1F) upon exposure to rat liver microsomes, 95.3%, was about 1.6 times greater (95.3%/58.4%). Based on these in vitro results, it is believed that Compound (1F) is effective in resisting metabolism by the liver in vivo and, thus, being more available will be more effective in ORL-1 receptor modulation than Compound W-212393.

6.9 Example 9: In Vivo Assay of the Bioavailability of Compounds (1C)/(1E), 405K, and W-212393

Male Sprague-Dawley [Crl:CD(SD)] rats obtained from Charles River Laboratories Japan, Inc. were used in each determination. The rats were 8 weeks old on the day of test compound administration. Under isoflurane anesthesia, the rats were first subjected to surgery to insert a cannula tube into the jugular vein at least three days before test compound administration. Rats were selected for further study based on the condition of the blood sampling apparatus and their body weight change after surgery.

Each compound tested was administered in a methylcellulose aqueous solution once orally to 2 rats. Methylcellulose 400 cP (Wako Pure Chemical Industries, Ltd., Japan) was the methylcellulose used for all administrations. To make each formulation for oral administration, an appropriate amount of the test compound was weighed into an agate mortar and suspended with 0.5 w/v % methylcellulose aqueous solution vehicle to provide a suspension with a concentration of 0.2 mg/mL of the compound undergoing testing.

The rats were dosed orally at 1 mg/kg under non-anesthesia in a non-fasted condition. Blood (0.2 mL/sample) was collected through the jugular cannula using a 1 mL syringe containing anticoagulants (0.89 M EDTA-2K plus 20% heparin) at various time points (0.25, 0.5, 1, 2, 4, 6, 8, and 24 hours) after dosing. Replacement fluid—0.2 mL of saline solution—was administered through the jugular cannula after each sampling. The blood samples obtained were centrifuged at a temperature of about 4° C. for 10 minutes at 3,500 rpm to obtain plasma. Thereafter, each plasma sample was transferred into a tube and stored in a freezer for later workup and analysis.

The supernatants obtained following protein precipitation of the plasma samples were analyzed by liquid chromatography with tandem mass spectrometry detection ("LC-MS-MS") to determine the concentration of test compound at each time point. The samples thus analyzed were prepared without an internal standard. Therefore, the analytical method made use of a calibration curve constructed from the analysis of blank (i.e., undosed) plasma spiked with various known quantities of analyte under identical conditions. From this information, pharmacokinetic parameters, in particular bioavailability, were calculated using WINNONLIN software (Certara, L.P., Princeton, N.J.) based on a non-compartment model.

In connection with Compound (1), multiple determinations were conducted in this example—some with the free base Compound (1C) and some with the mono-hydrochloride salt Compound (1E). To indicate this, the designation Compound (1C)/(1E) is used. Table 11 below summarizes the results of the bioavailability determinations for Compounds (1C)/(1E), 405K, and W-212393. The mean bioavailability from multiple determinations is provided in Table 11. The number in parenthesis following the mean indicates the number of determinations from which the mean was obtained. For Compound (1C)/(1E), bioavailability determination results from which the mean was obtained ranged from a low of 25.7% to a high of 58.5%.

TABLE 11

Results of Bioavailability Determinations

| | Compound (1C)/(1E) | Compound 405K | Compound W-212393 |
|---|---|---|---|
| Average Bioavailability (%) | 41.4 (14) | 63.7 (2) | 2.1 (2) |

As can be noted from the results in Table 11, the average bioavailability was strikingly lower for Compound W-212393 relative to Compound (1C)/(1E). Specifically, the bioavailability of Compound (1C)/(1E) was, on average, 41.4%. In contrast, the average bioavailability of Compound W-212393 was 2.1%. Thus, the amount of Compound (1C)/(1E) bioavailable for, inter alia, receptor modulation, was at least about 20 times greater (41.4%/2.1%=19.7). Even for the lowest bioavailability value determined for Compound (1C)/(1E) from all 14 experiments, 25.7%, the amount of Compound (1C)/(1E) bioavailable was still at least about 12 times greater than for Compound W-212393 (25.7%/2.1%=12.2).

6.10 Example 10: In Vitro Assay of Free Unbound Compounds (1F) and W-212393

The extent of in vitro binding of Compound (1F) or W-212393 to rat serum was determined as an assessment of the availability of free unbound compound for modulating receptor activity according to a procedure disclosed in, e.g., Example 15 of U.S. Pat. No. 9,290,488, which is hereby incorporated by reference in its entirety. Serum from rats containing a tested compound in one chamber of a dialysis cell was dialyzed with phosphate buffered saline ("PBS") in the other chamber; thereafter, the supernatant from each chamber was analyzed for the concentration of the tested compound present.

0.5 mg/kg of each tested compound was solubilized in 1/1 N,N-dimethylacetamide/1,2-propane diol. Control rat serum was obtained as the supernatant product after coagulation and centrifugation (3000 rpm for 10 min. at 4° C.) of whole blood taken via cannula inserted into the jugular vein of rats (Crl:CD (SD), male, fed). 50 µL of each tested compound solution was added to 1.2 mL of control rat serum. The final concentration of each tested compound in the serum sample was adjusted to 2 µg/mL by adding an appropriate volume of PBS. A cell suitable for equilibrium dialysis was used in the determinations. A SPECTRA/POR dialysis membrane (with molecular mass cutoff of 12,000-14,000 Da, Spectrum Laboratories, Inc., Rancho Dominguez, Calif.) separated the dialysis cell into two chambers. A 500 µL aliquot of the serum sample containing a tested compound was applied to one chamber (serum chamber) of the dialysis cell. A 500 µL aliquot of PBS was applied to the other chamber (PBS chamber) of the dialysis cell. The dialysis study was conducted in duplicate for each tested compound.

After 24 hours of equilibrium dialysis at 37° C., 30 µL of liquid from the serum chamber of the dialysis cell was collected and to this was added 270 µL of fresh PBS (this combination was designated Sample "A"). Then, 270 µL of liquid from the PBS chamber of the dialysis cell was collected and to this was added 30 µL of control rat serum (i.e., rat serum never exposed to any test compound, this combination was designated Sample "B"). A 5-10 fold volume of methanol was added to each of Samples A and B. Thereafter, each was mixed vigorously with the methanol and then centrifuged (3000 rpm for 10 min at 4° C.). Each supernatant was analyzed by LC-MS-MS.

For each tested compound, the mean amount of tested compound present in each of Samples A and B was determined from the peak areas obtained by LC-MS-MS analysis. Thereafter, the percentage of free unbound tested compound was calculated from the ratio of the tested compound amount determined from Sample B divided by the sum of the tested compound amounts determined from Sample A and Sample B.

Table 12 below summarizes the results of the free unbound compound fraction determinations for Compounds (1F) and W-212393 where the "fraction unbound (%)" is the percentage of free compound that is not bound to plasma proteins. The results from multiple determinations are provided for Compound (1F).

TABLE 12

Results of Free Unbound Compound Fraction Determinations

| | Compound (1F) | Compound W-212393 |
|---|---|---|
| Fraction Unbound (%) | 65-70 | <0.1 |

As can be noted from the results in Table 12, the free unbound compound fraction was strikingly lower for Compound W-212393 relative to Compound (1F). Specifically, the free unbound compound fraction of Compound (1F) was, on average, 67.5%. In contrast, the free unbound compound fraction of Compound W-212393 was less than 0.1%. Thus, the amount of Compound (1F) available for, inter alia, receptor modulation, was on average at least about 675 times greater than for Compound W-212393 (67.5%/0.1%).

6.11 Example 11: In Vivo Assay of Brain Penetration of Compounds (1C), 405K, and W-212393

The in vivo distribution of Compound (1C), 405K, or W-212393 between rat brain homogenate and rat plasma was determined. In this method, a mixture of plasma and brain homogenate comprised a matrix, which was analyzed by LC-MS-MS.

0.5 mg/kg of each tested compound was solubilized in 1/1 N,N-dimethylacetamide/1,2-propane diol to provide a blend. The blend was administered once intravenously to anesthetized rats (Crl, CD(SD), male, fed). At 30 minutes after the dosing, whole blood was taken from the abdominal aorta of each anesthetized rat and the brain was promptly removed.

After adding water (3-fold by weight), the brain was prepared as a 25% (w/w) homogenate using a POLYTRON homogenizer (Kinematica, Inc., Bohemia, N.Y.). To minimize the effects of the matrix on the measurement, to the brain homogenate sample was then added the equivalent volume of control (i.e., undosed) rat plasma obtained using the centrifugation conditions below.

A dosed-rat plasma sample was collected by centrifugation (3,500 rpm for 10 min. at 4° C.) of the whole blood. To again minimize the effects of the matrix on the measurement, to the plasma sample was added the equivalent volume of a control brain homogenate, prepared as described above but with brain extract from intact control (i.e., undosed) rats.

A 5-10 fold volume of methanol was added to the brain homogenate sample and to the plasma sample prepared above. After vigorous mixing the supernatants obtained from each by centrifugation were analyzed by LC-MS-MS. The peak areas of the test compound in each brain homogenate sample and plasma sample were measured. For each compound tested, the mean amount of compound present in each of the brain homogenate sample and the plasma sample was determined from the peak areas obtained by LC-MS-MS analysis. Thereafter, $K_p$ values were calculated from the mean peak area of the brain homogenate samples ($MPA_{brain}$) and the mean peak area of the plasma samples ($MPA_{plasma}$) as follows:

$$K_p = \frac{4 \times MPA_{brain}}{MPA_{plasma}}. \quad \text{(Eq. 2)}$$

Table 13 below summarizes the results of the brain penetration determinations for Compounds (1C), 405K, and W-212393. The results from two separate groups of determinations are provided for Compound (1C).

TABLE 13

Results of Brain Penetration Determinations

| | Compound (1C) | Compound 405K | Compound W-212393 |
|---|---|---|---|
| $K_p$ ‡ | 0.025, 0.040 | 0.00 | 0.5 |

As can be noted from the results in Table 13, the brain penetration of Compound W-212393 was strikingly higher relative to Compound (1C). Specifically, the brain penetration of Compound W-212393 was 0.5. In contrast, the brain penetration of Compound (1C) was, on average, 0.033. Thus, the amount of brain penetration of Compound W-212393 was at least about 15 times greater (0.5/0.033=15.2) than the brain penetration of Compound (1C). Even at the maximum brain penetration value determined for Compound (1C), 0.040, the amount of brain penetration of Compound W-212393 was at least about 13 times greater (0.5/0.040=12.5) than the brain penetration of Compound (1C).

6.12 Example 12: In Vitro Assay of Protein Binding of Compounds (1F), 405K, and W-212393

The extent of in vitro binding of Compound (1F), 405K, or W-212393 to rat plasma was determined as an assessment of the protein binding of each compound, i.e., compound unavailable for modulating receptor activity. Plasma from rats containing a tested compound in one chamber of a dialysis cell was dialyzed with PBS in the other chamber; thereafter, the supernatant from each chamber was analyzed for the concentration of the tested compound present.

A cell suitable for equilibrium dialysis was used in the determinations. The dialysis membrane described in Example 10 (with molecular mass cutoff of 12,000-14,000 Da) separated the dialysis cell into two chambers. The membrane was soaked with purified water and PBS before being placed into the dialysis cell.

4 µL of an iv formulation of each tested compound was added to 996 µL of rat plasma, the latter obtained using syringe containing heparin and EDTA by the procedure described in Example 10, to provide a plasma sample with a tested compound concentration of 2 µg/mL. 450 µL of the plasma sample was applied to one chamber (plasma chamber) of the dialysis cell. A 450 µL aliquot of PBS was applied to the other chamber (PBS chamber) of the dialysis cell. The dialysis study was conducted in duplicate for each tested compound.

After 24 hours of equilibrium dialysis at 37° C., 30 µL of liquid from the plasma chamber of the dialysis cell was collected and to this was added 270 µL of fresh PBS (this combination was designated Sample "1"). Then, 270 µL of liquid from the PBS chamber of the dialysis cell was collected and to this was added 30 µL of control rat plasma (i.e., rat plasma never exposed to any test compound, this combination was designated Sample "2"). Thereafter, each sample was mixed well and stored in a freezer until the next analysis step.

After the protein precipitated in the freezer, each supernatant thusly obtained was analyzed by LC-MS-MS for unbound test compound. For each tested compound, the mean amount of tested compound present in each of Samples 1 and 2 was determined from the peak areas obtained by LC-MS-MS analysis. Thereafter, the percentage of rat protein-bound ("RPB") tested compound was calculated as follows:

$$RPB = \left[ 1 - \frac{(10/9) \times Area_{Sample\ 2}}{10 \times Area_{Sample\ 1}} \right] \times 100 \quad \text{(Eq. 3)}$$

Table 14 below summarizes the results of the rat protein binding determinations for Compounds (1F), 405K, and W-212393. The results from multiple determinations are provided for Compound (1F).

TABLE 14

Results of Protein Binding Determinations

| | Compound (1F) | Compound 405K | Compound W-212393 |
|---|---|---|---|
| Rat Protein Binding (%) | 50.9, 53.0 | 85.7 | N/A |

As can be noted from the results in Table 14, the amount of rat protein bound compound was lower for Compound (1F) relative to Compound 405K. Specifically, the bound compound fraction of Compound (1F) was, on average, 52%. In contrast, the bound compound fraction of Compound 405K was about 86%. Compound W-212393 proved to be unstable in plasma; because it degraded during the course of the determination, presence of the starting molecular structure could not be determined in the supernatant.

6.13 Example 13: In Vivo Functional Observational Battery of Compounds (1D), 405, and W-212393

Compound (1D) was administered in a 0.5 w/v % methylcellulose aqueous solution once orally to 6 rats/group at dose levels of 0 (vehicle control), 60, 300, and 600 mg/kg to evaluate the effects on the CNS by using a functional observational battery ("FOB"). The FOB was conducted pre-dosing and up to 24 hours post-dosing. Control animals (6 rats) received a 0.5 w/v % methylcellulose aqueous solution vehicle (hereafter "0.5% MC") in a similar manner. Methylcellulose 400 cP (Wako Pure Chemical Industries, Ltd., Japan) was the methylcellulose used for all administrations. Analysis and verification of the concentration and homogeneity of the test substance in the vehicle was conducted by methods known to those in the art. Measured test substance concentrations were 100.7-102.0% of the nominal concentrations with a relative standard deviation of 1.0% or 2.0%.

Male Crl:CD(SD) rats, 4 weeks old upon receipt, were obtained from Charles River Laboratories Japan, Inc. They were acclimated to a 12-hour light-dark cycle at a temperature of 22.1-23.6° C. for a 2 week period—from receipt until 1 day prior to dosing. Drinking water was provided ad libitum while the rats were caged. The animals were allowed free access to food except prior to dosing, when they were fasted for at least 16 hours from the previous evening. On the day of dosing, food was provided 8 hours post-dosing.

The body temperature of the rats exhibiting no abnormalities in physical condition or body weights during the acclimation period was measured twice at an interval of 30-60 minutes. Six week old rats weighing 178-220 g and with individual mean body temperature ranging between 37° C. and 39° C. and with less variation between the two values were preferentially selected for the study. The selected rats were randomly distributed into groups of 6 using a stratified randomization procedure based on body temperature.

A single administration was made with the dosing volume for each rat calculated based upon its body weight on the day of dosing (prior to dosing). The dosing formulations were drawn into the appropriate size of sterile, disposable polypropylene syringes while being stirred thoroughly with a stirrer and then administered to the rats via oral gavage using gastric intubation tubes. Observation of the rats was conducted by 3 observers, all of whom were outside of the animal room during dosing, at a plurality of the following time points: pre-dosing and at 0.5 (optionally), 1, 2, 4, 6 (optionally), 8 (optionally), and 24 (optionally) hours post-dosing. Observer 1 recorded home cage and hand-held observations and body temperature measurements. Observer 2 recorded open-field observations. Observer 3 recorded observations for sensorimotor reflexes. Table 15 provides the specific observation parameters that were noted by the observers.

TABLE 15

| Specific Observation Parameters | |
|---|---|
| Home cage observations | Posture/position, vocalization, piloerection, tremors, convulsions, respiration, feces and urine |
| Hand-held observations | Ease of handling and removal from the cage, body temperature (rectal), muscle twitching, muscle tone, skin, pupil size, lacrimation, exophthalmos and salivation |
| Open field observations | Stereotypy, abnormal behavior, locomotor activity, palpebral closure and gait |
| Sensorimotor reflex observations | Catalepsy, knuckling, pupillary reflex, palpebral reflex, pinna reflex, visual placing response, auditory response, pain response, wheelbarrowing, hopping, aerial righting reflex, hindlimb landing foot-splay and forelimb grip strength |

The mean group values and SDs were calculated for numerical data (body temperature, pupil size, hindlimb landing foot-splay, grip strength) and the data were analyzed for homogeneity of variance using Bartlett's test (5% level of significance). When the variance was homogeneous between the groups, Dunnett's test was conducted between the control and test substance groups. When the variance was heterogeneous based on Bartlett's test, a mean rank test of the Dunnett type was conducted. Differences from the control group were evaluated at the two-tailed 5% level of significance and presented as $p<0.05$ or $p<0.01$. Differences from the pre-dosing values were calculated for the body temperature and pupil size at the scheduled time points and presented as the mean values and SDs. Statistical analysis was not conducted on these values.

No statistically significant differences were noted in the body temperature, pupil size, hindlimb landing foot-splay, or forelimb grip strength between the control and any Compound (1D) treated group. Decreased locomotor activity was observed in 1 rat each in the 300 and 600 mg/kg groups at 4 or 8 hours post-dosing; however, this finding at these time points was considered not to be treatment-related because it was also observed in 1 or 2 control rats between 4 and 8 hours post-dosing. In summary, no Compound (1D) treatment-related changes were noted in home cage, hand-held, open field, or sensorimotor reflex observation items at any of the time points after up to 600 mg/kg oral dosing with Compound (1D).

In conclusion, because Compound (1D) had no effects on the general physical condition or behavior of rats at up to 600 mg/kg, its no-observed-adverse-effect-level ("NOAEL") was 600 mg/kg in this study.

The observers noted the adverse effects in Table 16 below upon the administration of Compound 405 according to the procedures described above.

TABLE 16

Adverse Effects Observed upon Administration of Compound 405

| Test Substance | Dose (mg/kg) | Parameter Observed | Time after Administration (hours) | | | | | |
|---|---|---|---|---|---|---|---|---|
| | | | 1 | 2 | 4 | 6 | 8 | 24 |
| Vehicle | 0 | Behavior | N | N | N | N | N | N |
| Compound 405 | 10 | Increased touch response | 1 of 6 | N | N | N | N | N |
| | 30 | Jumping | N | N | N | 1 of 6 | N | N |
| | | Biting behavior | N | N | N | 3 of 6 | N | N |
| | 100 | Biting behavior | N | N | N | 1 of 6 | 1 of 6 | N |
| | 300 | Jumping | N | N | N | 1 of 6 | 2 of 6 | N |
| | | Biting behavior | N | N | N | 2 of 6 | 1 of 6 | N |

N = Normal or no abnormalities observed
Numerical value = Number of rats with each parameter per total number of rats observed At 10 mg/kg, increased touch response was observed in only 1 of the 6 rats dosed. Moreover, because it was a mild and transient effect this was likely of only minor physiological significance. However, more severe FOB parameter abnormalities were evident at higher doses: biting behavior at 30, 100, and 300 mg/kg and jumping at 30 and 300 mg/kg. In light of these observed FOB abnormalities, it was concluded that the NOAEL for Compound 405 was 10 mg/kg in this study.

The observers noted the adverse effects in Table 17 below upon the administration of Compound W-212393 also according to the procedures described above.

TABLE 17

Adverse Effects Observed upon Administration of Compound W-212393

| Test Substance | Dose (mg/kg) | Parameter Observed | Time after Administration (hours) | | | | |
|---|---|---|---|---|---|---|---|
| | | | 0.5 | 1 | 2 | 4 | 6 |
| Vehicle | 0 | Behavior | N | N | N | N | N |
| Compound W-212393 | 1 | Behavior | N | N | N | N | N |
| | 3 | Hypoactivity | N | 6 of 6 | N | N | N |
| | | Jumping | N | 3 of 6 | 2 of 6 | N | N |
| | | Biting behavior | N | 1 of 6 | N | N | N |
| | 300 | Jumping | 2 of 6 | N | N | N | N |
| | | Biting behavior | 3 of 6 | N | N | N | N |
| | | Abdominal position/side lying position | 6 of 6 | 6 of 6 | 6 of 6 | 6 of 6 | 6 of 6 |
| | | Respiratory irregularity | 6 of 6 | 6 of 6 | 6 of 6 | 6 of 6 | 6 of 6 |
| | | Decreased muscle tone | 6 of 6 | 6 of 6 | 6 of 6 | 6 of 6 | 6 of 6 |
| | | Loss of auricular reflex/ righting reflex | 6 of 6 | 6 of 6 | 6 of 6 | 6 of 6 | 6 of 6 |
| | | Loss of flexed or extension reflex | 6 of 6 | 6 of 6 | 6 of 6 | 6 of 6 | 6 of 6 |
| | | Loss of pain reaction | 6 of 6 | 6 of 6 | 6 of 6 | 6 of 6 | 6 of 6 |

N = Normal or no abnormalities observed
Numerical value = Number of rats with each parameter per total number of rats observed At the dose of 300 mg/kg of Compound W-212393, severe FOB parameter abnormalities were observed for all rats. Therefore, additional evaluations were performed at significantly lower doses (1 and 3 mg/kg). Unlike the FOB abnormalities observed at the 3 mg/kg dose, a dose of 1 mg/kg of Compound W-212393 had no effect on general behavior or neurobehavioral function. It was concluded that the NOAEL for Compound W-212393 was 1 mg/kg in this study.

6.14 Example 14: In Vivo Repeated Administration of Compound (1D) Decreased Wakefulness, Increased NREM Sleep Compound (1D) was administered in a 0.5 w/v % methylcellulose aqueous solution once daily orally to rats at a dose level of 30 mg/kg for 7 days followed by cessation of administration on the $8^{th}$ day and its effects on brain waves (via EEG) and limb movements (via EMG) evaluated. Control animals received 0.5% MC in a similar manner. The methylcellulose used and analysis and verification of the concentration and homogeneity of the Compound (1D) solutions administered was as described in Example 13.

Male Crl:CD(SD) rats, 6 weeks old upon receipt, were obtained from Charles River Laboratories Japan, Inc. At a temperature of 22-24° C., they were acclimated for at least 5 days to a 12-hour light-dark cycle with lights on from 6 AM to 6 PM. Drinking water and food were provided ad libitum. A telemetry transmitter (TL10M3-F50-EEE, Data Sciences International, Inc., Shanghai) which was designed for recording EEG and EMG data from conscious, freely moving rodents was used. In an isoflurane anesthetized rat, a telemetry transmitter was implanted into the abdominal cavity and a lead line was externalized via the dorsal neck through a subcutaneous tunnel. The rat was placed on a stereotaxic frame and implanted with EEG electrodes according to the brain atlas. The EEG electrodes were placed on the dura matter of the parietal cortex (posterior: 1.8 mm, lateral: ±3.5 mm, from the bregma [the point or area of the skull where the sagittal and coronal sutures joining the parietal and frontal bones come together]) and the occipital cortex (posterior: 5.2 mm, lateral: ±2.0 mm, from the bregma). Two stainless steel wires for EMG recording were implanted into dorsal neck muscle of the rat. Each EEG electrode and stainless wire was soldered to the lead line of the telemetry transmitter, which was fixed to the skull with quick self-curing acrylic resin (ADFA, Shofu, Inc., Kyoto, Japan). After surgery, each rat was uniquely identified by a serial number marked on its tail. An antibiotic (0.1 mL mycillin sol/rat [Meiji Seika Pharma Co., Ltd., Tokyo]) and an analgesic (0.05 mL buprenorphine hydrochloride/kg [0.2 mg lepetan/mL, Otsuka Pharmaceutical Co., Ltd., Rockville, Md.]) were administered intramuscularly to the rats for 4 days beginning on the day of surgery to prevent infection and palliate pain, respectively. During the recovery period (at least 5 days after surgery), the rats were again acclimated as described above in their recording cages until the first dosing day.

The first day of a dosing period was designated as Day 1 and dosing continued daily on Days 2-7. The rats were 8-10 weeks old on Day 1. Continuous EEG and EMG recording (using DATAQUEST A.R.T. recording software [Data Sciences International Inc., Tokyo]) was begun 1 hour before dosing on Days 1, 4, and 7 of a period and continued for at least 24 hours after dosing on Days 1 and 4 and for at least 48 hours after dosing on Day 7. The sampling frequency for EEG/EMG recording was 500 Hz. The cross-over experimental dosing design shown in Table 18 was used to assess the effects of Compound (1D) on the sleep-wake cycle by EEG/EMG analysis as compared with vehicle treated rats.

TABLE 18

Cross-over Experimental Dosing Design

| Period | Test Substance | Dose (mg/kg/day) | Group Designation/ Number of Rats |
|---|---|---|---|
| 14.1 | Vehicle | 0 | Group A/4 |
|  | Compound (1D) | 30 | Group B/3 |
| 14.2 | Compound (1D) | 30 | Group A/4 |
|  | Vehicle | 0 | Group B/3 |

As described in Example 13, test substance administration was via oral gavage with the dosing volume for each nominally 200 g rat calculated prior to dosing based upon its exact body weight on the day of dosing. Dosing occurred between 5:30 PM and 5:50 PM. A 7 day wash-out period during which there was no administration was used between Periods 14.1 and 14.2.

For the purposes of this study, the EEG/EMG data collected was structured into 20 second long epochs. Each epoch was scored by analysis software (SLEEPSIGN, Kissei Comtec Co., Ltd., Nagano, Japan) as either wakefulness, REM sleep, or NREM sleep. The data for all epochs were examined manually as a check that the automated scoring was correct. The percentage of time spent in each sleep stage was calculated for every 1 hour and every 3 hour "time block" by the analysis software. For the purposes of this study, for either time block the sum of the percentage of time spent in NREM sleep and the percentage of time spent in REM sleep was ascribed to the percentage of time spent sleeping, i.e., to the sleep portion of the sleep-wake cycle, the percentage of time spent in wakefulness was ascribed to the percentage of time spent not sleeping, i.e., to the wake portion of the sleep-wake cycle, and the sum of the percentages of time spent in NREM sleep, in REM sleep, and in wakefulness equaled 100%. Results from rats that perished during the study or were exposed to noise that may have affected the epoch analysis were excluded. The results obtained were expressed as the mean value±STDE. Statistical analyses were performed by SAS analytics software (Release 9.4, SAS Institute Japan, Ltd., Tokyo) using the unpaired student's t-test. The results obtained from the testing are illustrated in FIGS. 5-12. In FIGS. 5-12, the symbol+adjacent to a particular data point or bar indicates that, for that data point or bar, there is a significant difference from the vehicle by the unpaired student's t-test with $p<0.05$. Also in these figures, the symbol * adjacent to a particular data point or bar indicates that, for that data point or bar, there is a significant difference from the vehicle by the unpaired student's t-test with $p<0.01$.

Figure 5A:
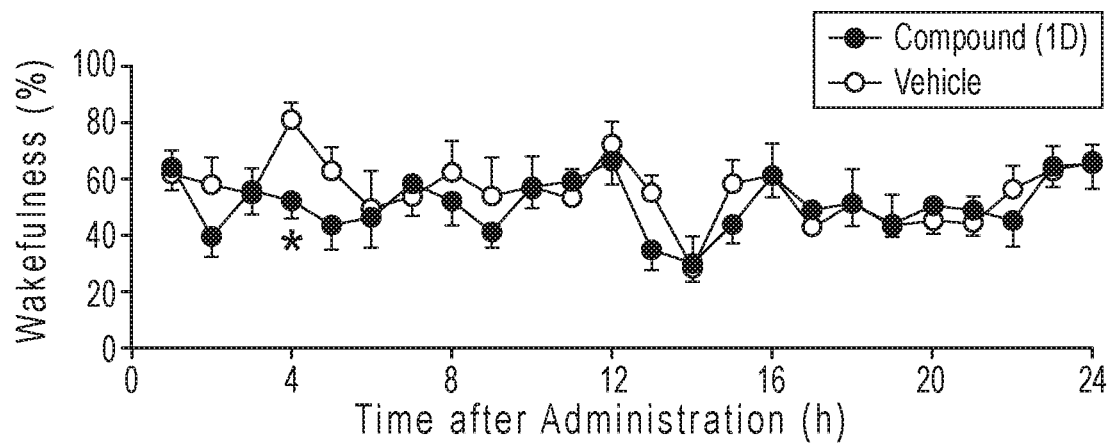
FIG. 5A shows a graph of the effects of 30 mg/kg/day of Compound (1D) on rat wakefulness during the 24 hour period after Day 1 dosing.
Figure 5B:
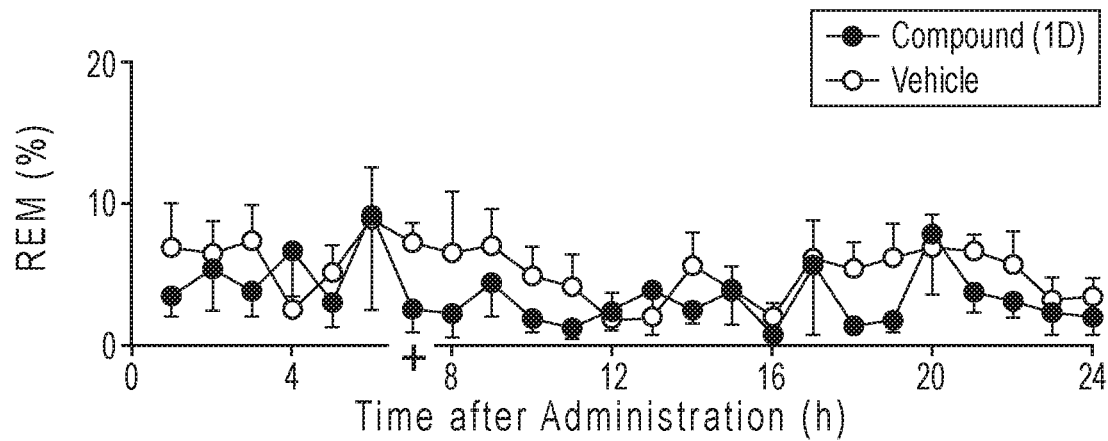
FIG. 5B shows a graph of the effects of 30 mg/kg/day of Compound (1D) on rat rapid eye movement ("REM") sleep during the 24 hour period after Day 1 dosing.
Figure 5C:
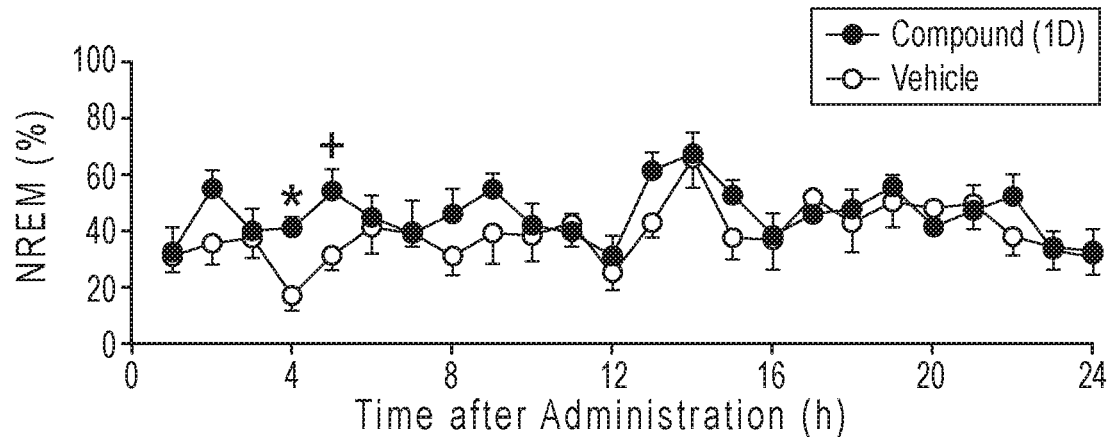
FIG. 5C shows a graph of the effects of 30 mg/kg/day of Compound (1D) on rat non-rapid eye movement ("NREM") sleep during the 24 hour period after Day 1 dosing.

On Day 1, FIG. 5A illustrates that the percentage of time spent in wakefulness, collected into 1 hour "time blocks", showed a decreasing tendency at many time points during the about 13 hours after dosing (the "lights-out period", i.e., from about 0.5 hours to about 13 hours after administration of Compound (1D)) compared to the vehicle group and was significantly decreased at 4 hours after dosing. Specifically, at 4 hours the amount of wakefulness—about 52%—was decreased significantly when compared to the about 81% for the vehicle group. Concurrently, FIG. 5C demonstrates that the percentage of time spent in desirable NREM sleep showed an increased tendency at many time points during the lights-out period compared to the vehicle group and was significantly increased at 4 and 5 hours after dosing. Specifically, at 4 and 5 hours the amount of NREM sleep—about 41% and 54%, respectfully—was increased significantly when each is compared to the vehicle group (about 17% and 31%, respectively). FIG. 5B shows that the percentage of time spent in less desirable REM sleep was often decreased and decreased significantly at 7 hours after dosing, i.e., to about 2.5% for 30 mg/kg of Compound (1D) compared to about 7.3% for vehicle. These data provide evidence that a single 30 mg/kg dose of Compound (1D) on Day 1 had a sleep-enhancing effect and induced sleep, in particular, during the lights-out period.

Figure 6A:
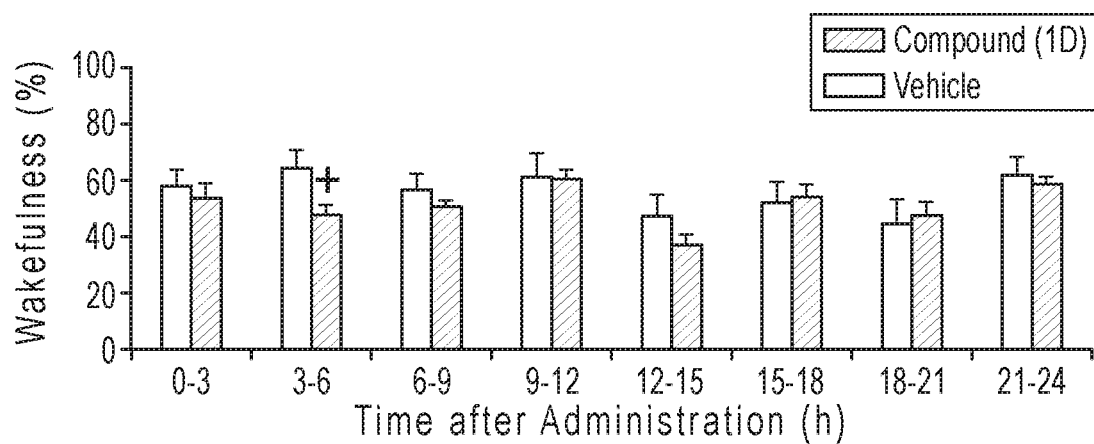
FIG. 6A shows a bar chart summarizing the effects of 30 mg/kg/day of Compound (1D) on rat wakefulness every 3 hours during the 24 hour period after Day 1 dosing.
Figure 6B:
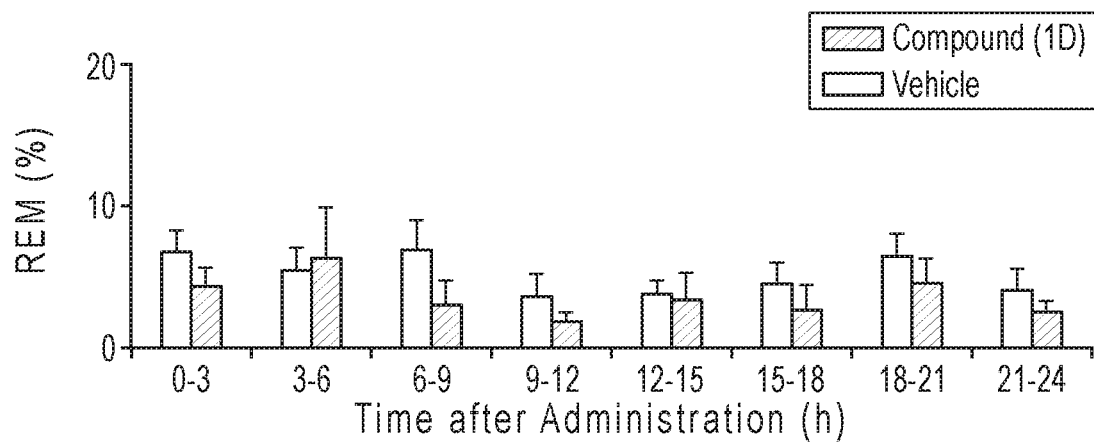
FIG. 6B shows a bar chart summarizing the effects of 30 mg/kg/day of Compound (1D) on rat REM sleep every 3 hours during the 24 hour period after Day 1 dosing.
Figure 6C:
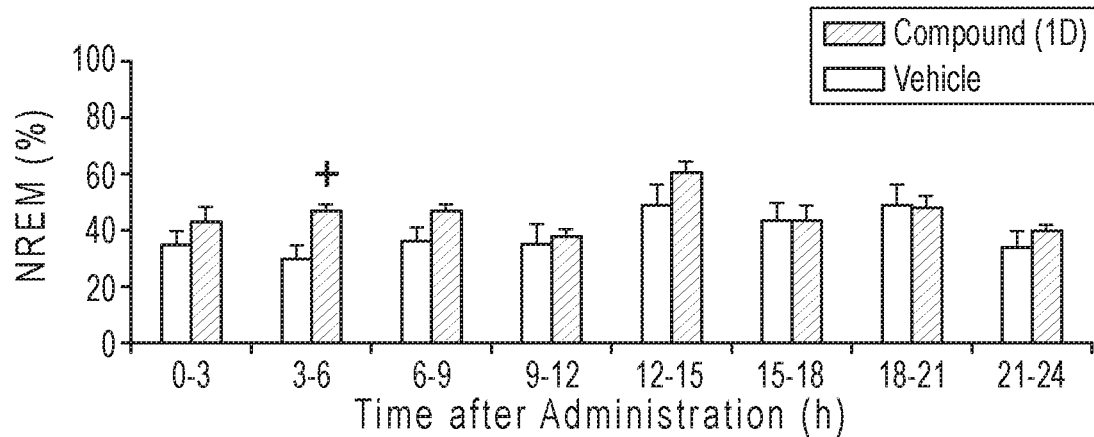
FIG. 6C shows a bar chart summarizing the effects of 30 mg/kg/day of Compound (1D) on rat NREM sleep every 3 hours during the 24 hour period after Day 1 dosing.

The percentage amounts of Day 1 wakefulness, REM sleep, and NREM sleep, collected into 3 hour "time blocks", are shown in FIG. 6. Pursuant to FIG. 6A, at 3 to 6 hours after dosing the total amount of wakefulness—about 47%—was decreased significantly for Compound (1D) administration when compared to the about 65% for the vehicle group. Pursuant to FIG. 6C, the total amount of NREM sleep—about 46%—was increased significantly when compared to the about 30% for the vehicle group. FIG. 6B illustrates that there were relatively minor effects and no significant effects on the percentage of time spent in REM sleep. These data again provide evidence that a single 30 mg/kg dose of Compound (1D) on Day 1 had a sleep-enhancing effect and induced sleep, in particular, during the lights-out period.

Figure 7A:
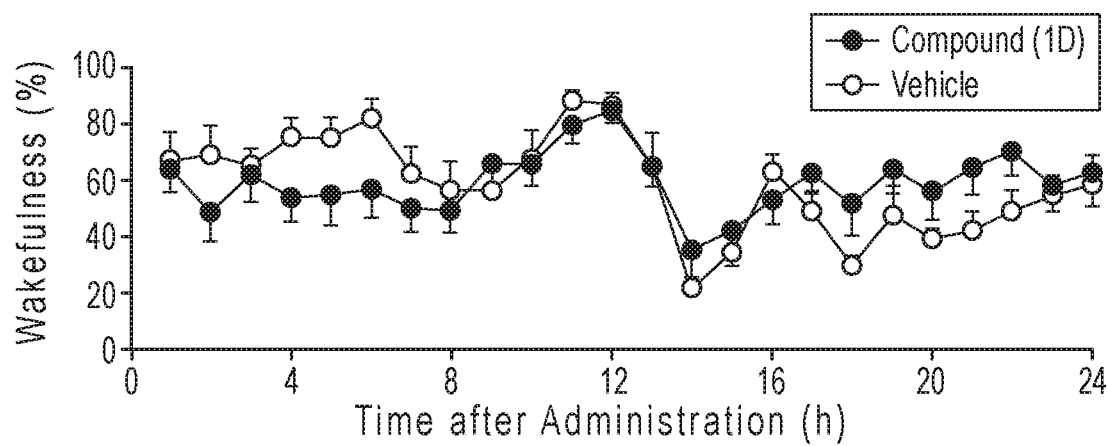
FIG. 7A shows a graph of the effects of 30 mg/kg/day of Compound (1D) on rat wakefulness during the 24 hour period after Day 4 dosing.
Figure 7B:
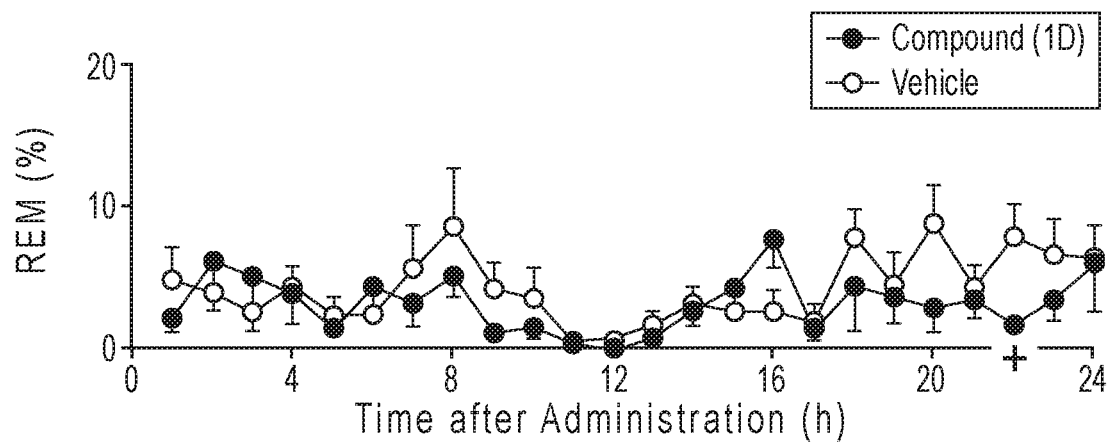
FIG. 7B shows a graph of the effects of 30 mg/kg/day of Compound (1D) on rat REM sleep during the 24 hour period after Day 4 dosing.
Figure 7C:
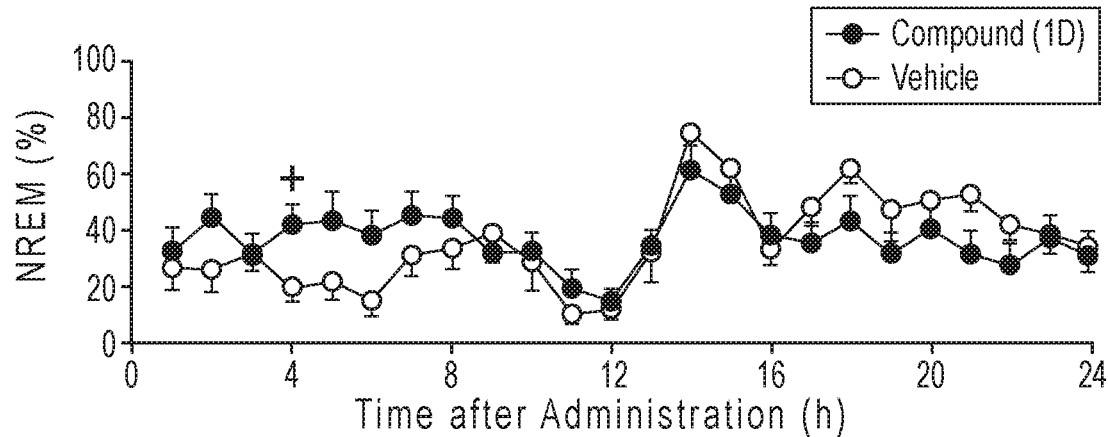
FIG. 7C shows a graph of the effects of 30 mg/kg/day of Compound (1D) on rat NREM sleep during the 24 hour period after Day 4 dosing.
Figure 8A:
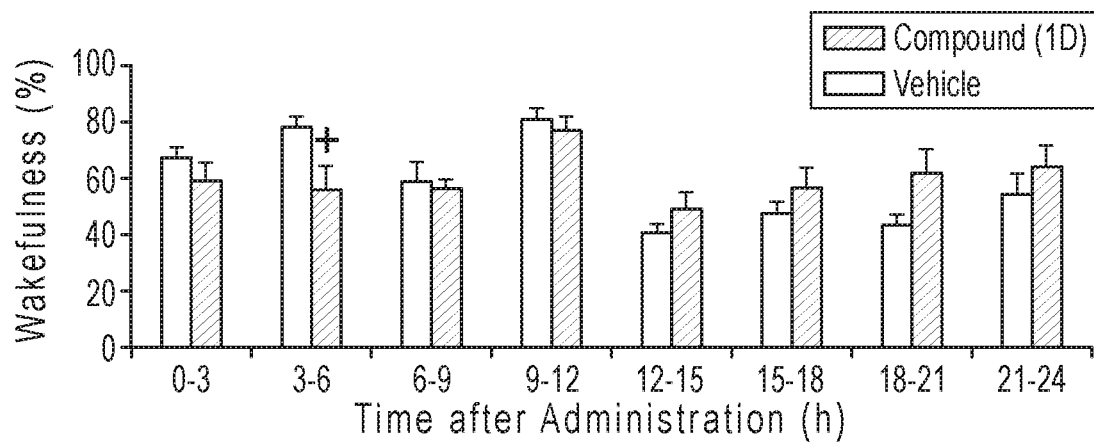
FIG. 8A shows a bar chart summarizing the effects of 30 mg/kg/day of Compound (1D) on rat wakefulness every 3 hours during the 24 hour period after Day 4 dosing.
Figure 8B:
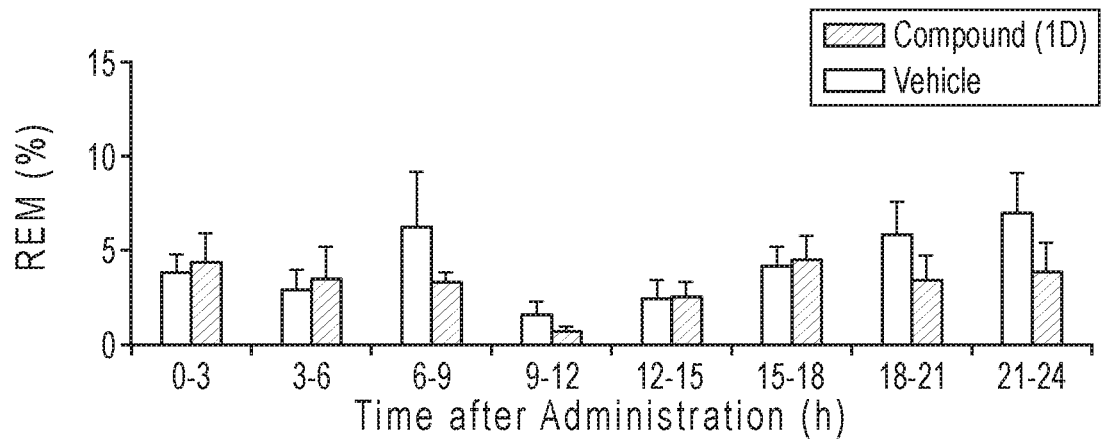
FIG. 8B shows a bar chart summarizing the effects of 30 mg/kg/day of Compound (1D) on rat REM sleep every 3 hours during the 24 hour period after Day 4 dosing.
Figure 8C:
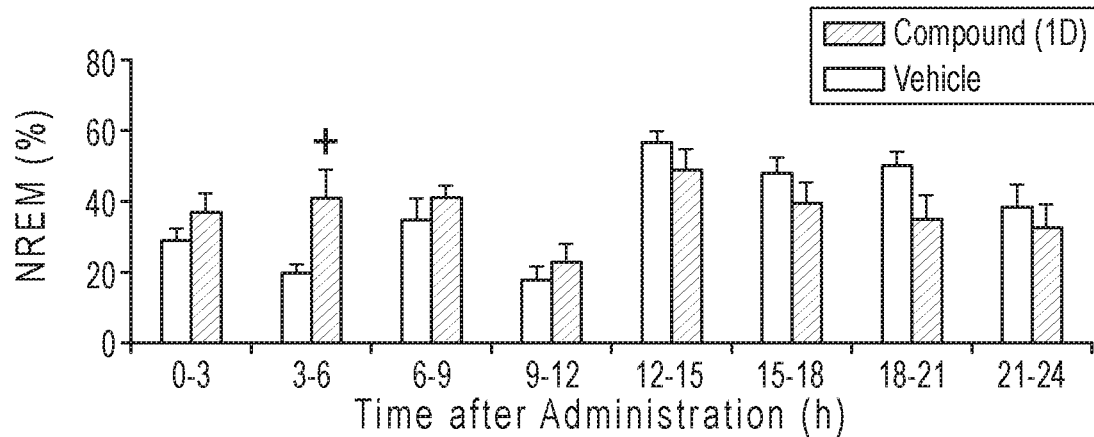
FIG. 8C shows a bar chart summarizing the effects of 30 mg/kg/day of Compound (1D) on rat NREM sleep every 3 hours during the 24 hour period after Day 4 dosing.

On Day 4, FIG. 7A illustrates that the percentage of time spent in wakefulness, like in FIG. 5A, again showed a decreasing tendency at many time points during the lights-out period. Concurrently, FIG. 7C demonstrates that the percentage of time spent in NREM sleep showed an increased tendency at many time points during the Day 4 lights-out period compared to the vehicle group and was significantly increased at 4 hours after dosing, i.e., about 42% for 30 mg/kg/day of Compound (1D) compared to about 20% for vehicle. FIG. 7B illustrates that there were relatively minor effects and no significant effects on the percentage of time spent in REM sleep. From FIG. 8A, it can be noted that at 3 to 6 hours after dosing the total amount of wakefulness—about 55%—was again significantly decreased while, pursuant to FIG. 8C, the total amount of NREM sleep was again significantly increased—about 41%—when each is compared to the vehicle group (about 78% and 19%, respectively). FIG. 8B illustrates that there were relatively minor effects and no significant effects on the percentage of time spent in REM sleep.

Figure 9A:
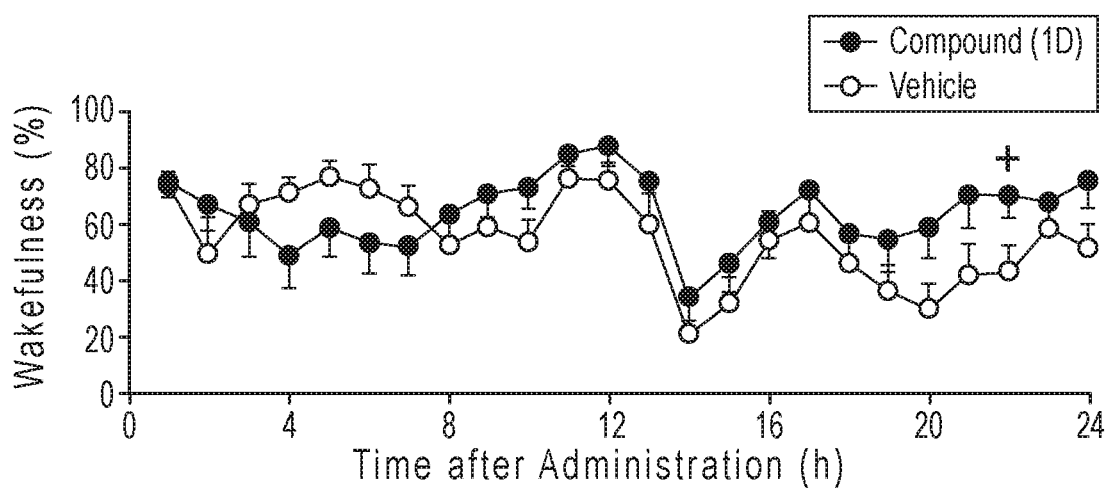
FIG. 9A shows a graph of the effects of 30 mg/kg/day of Compound (1D) on rat wakefulness during the 24 hour period after Day 7 dosing.
Figure 9B:
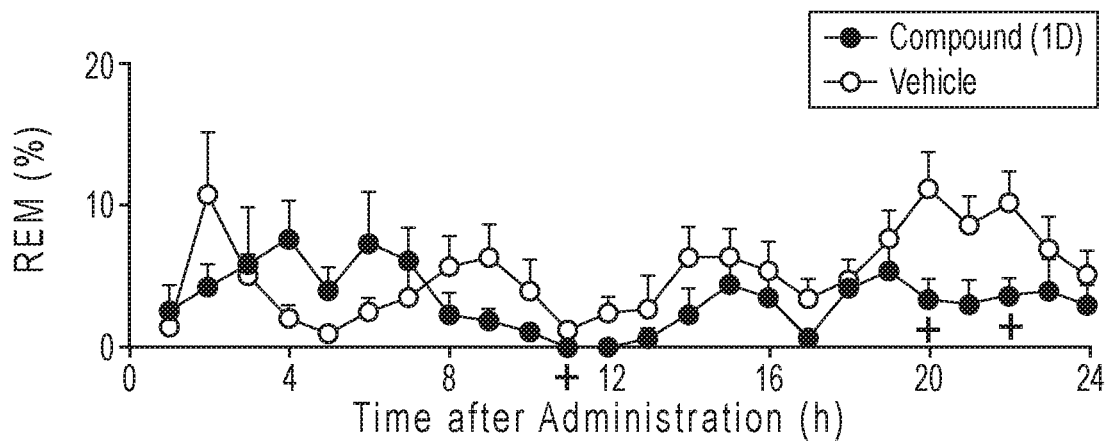
FIG. 9B shows a graph of the effects of 30 mg/kg/day of Compound (1D) on rat REM sleep during the 24 hour period after Day 7 dosing.
Figure 9C:
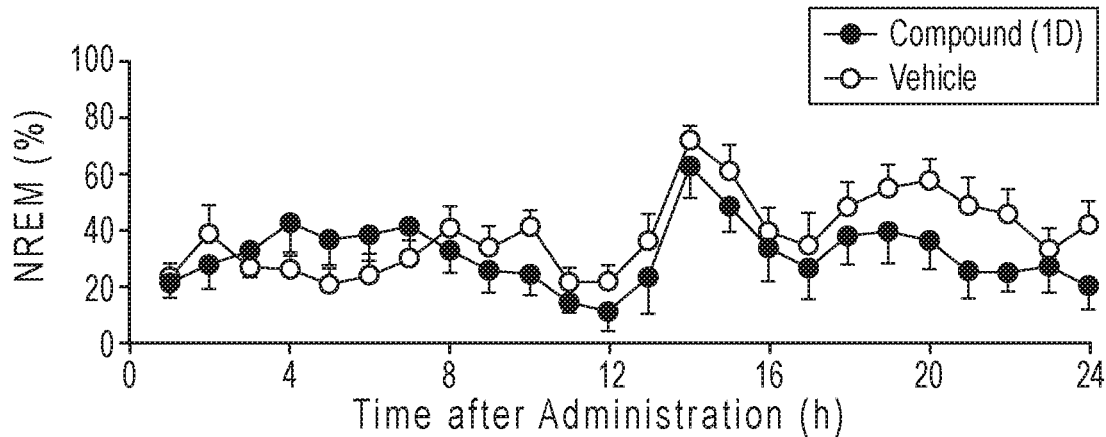
FIG. 9C shows a graph of the effects of 30 mg/kg/day of Compound (1D) on rat NREM sleep during the 24 hour period after Day 7 dosing.
Figure 10A:
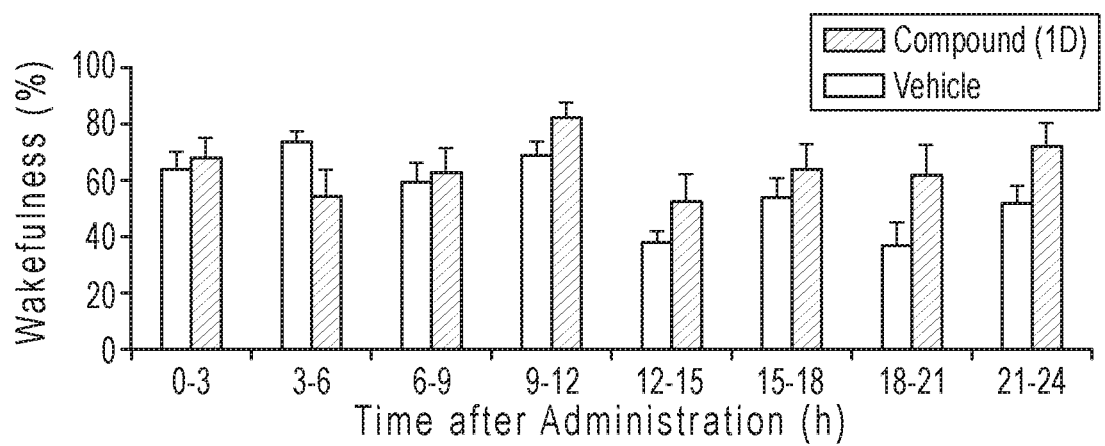
FIG. 10A shows a bar chart summarizing the effects of 30 mg/kg/day of Compound (1D) on rat wakefulness every 3 hours during the 24 hour period after Day 7 dosing.
Figure 10B:
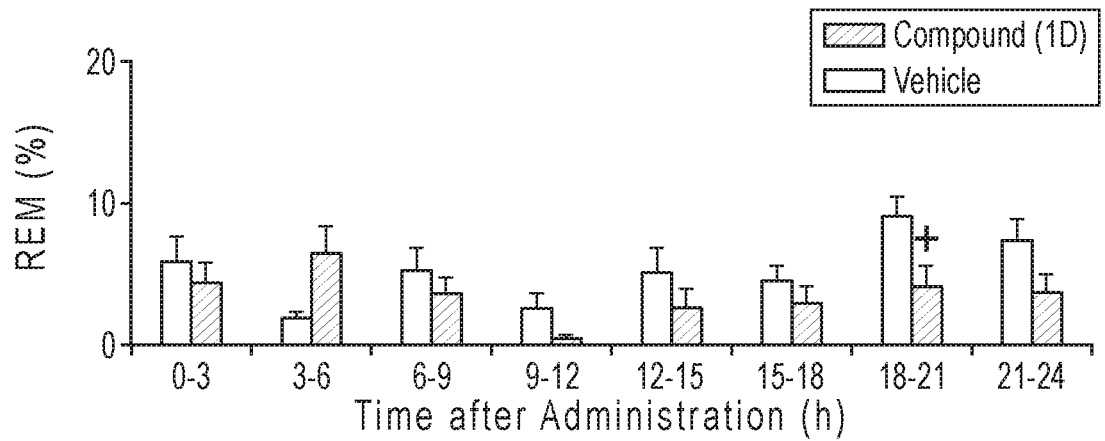
FIG. 10B shows a bar chart summarizing the effects of 30 mg/kg/day of Compound (1D) on rat REM sleep every 3 hours during the 24 hour period after Day 7 dosing.
Figure 10C:
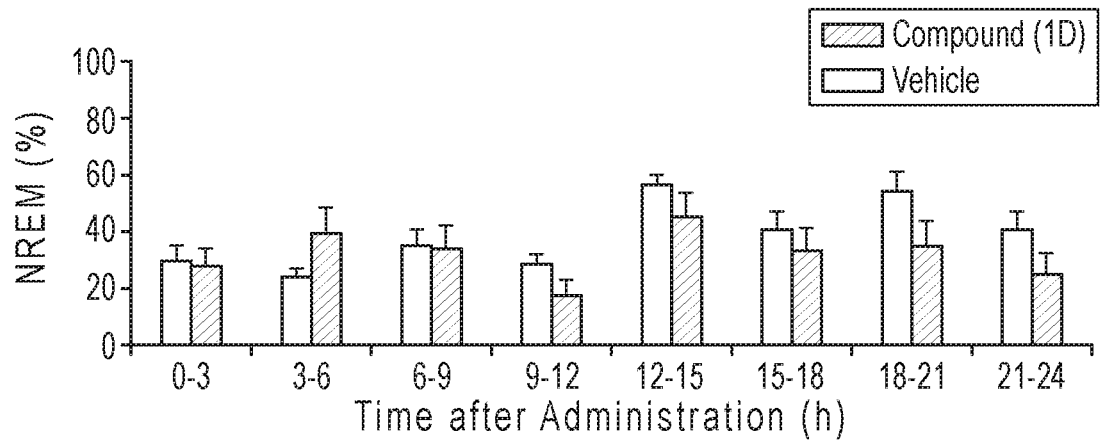
FIG. 10C shows a bar chart summarizing the effects of 30 mg/kg/day of Compound (1D) on rat NREM sleep every 3 hours during the 24 hour period after Day 7 dosing.

On Day 7, FIG. 9A illustrates that the percentage of time spent in wakefulness showed a decreasing tendency at several time points during the lights-out period. Concurrently, FIG. 9C illustrates that the percentage of time spent in desirable NREM sleep also showed an increased tendency at several time points during the Day 7 lights-out period compared to the vehicle group. FIG. 9B illustrates that there were relatively minor effects and no significant effects on the percentage of time spent in REM sleep. From FIG. 10A, it can be noted that at 3 to 6 hours after dosing the total amount of wakefulness again showed a decreased tendency while, pursuant to FIG. 10C, the total amount of NREM sleep again showed an increased tendency when compared to the vehicle group. FIG. 10B illustrates that there were relatively minor effects and no significant effects on the percentage of time spent in REM sleep.

The results of Compound (1D) administration over the seven day period demonstrate that there was minimal tachyphylaxis, i.e., the diminishing response to successive doses of a drug thus rendering it less effective over time. It can also be noted from FIGS. 5-10 that, desirably, administration or repeated administration of 30 mg/kg/day of Compound (1D) had no significant deleterious effect on either the percentage of time spent in wakefulness or the percentage of time spent in NREM sleep during the time following the lights-out period (the "lights-on period", i.e., from about 13 hours to about 24 hours after administration). Thus, repeated administration for 7 days did not induce either tolerance or residual effects in rats at a Compound (1D) dose of 30 mg/kg/day.

Collectively, these data demonstrated that the administration of a 30 mg/kg/day dose of Compound (1D) brought about significant sleep-enhancing effects in rats.

Figure 11A:
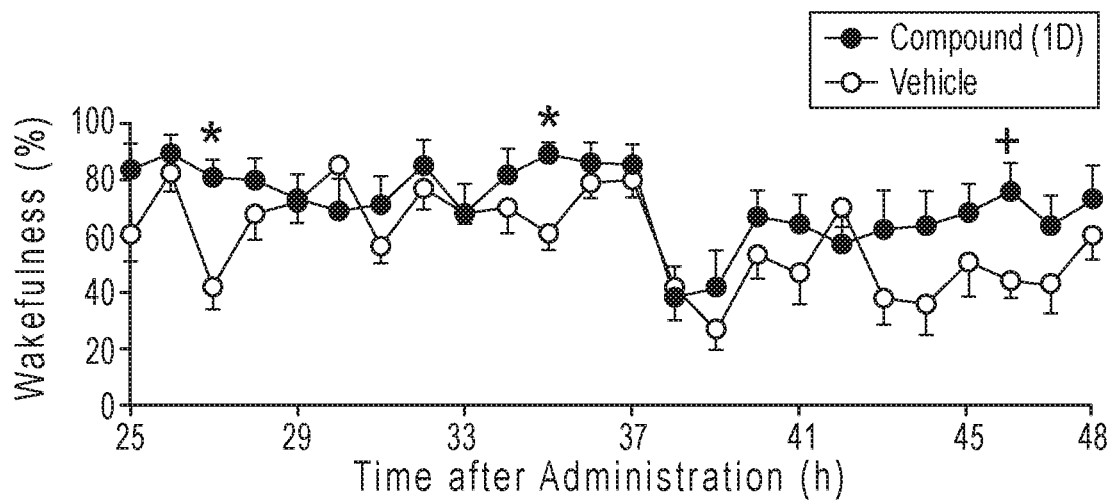
FIG. 11A shows a graph of the effects of 30 mg/kg/day of Compound (1D) on rat wakefulness during the 24 hour period on Day 8.
Figure 11B:
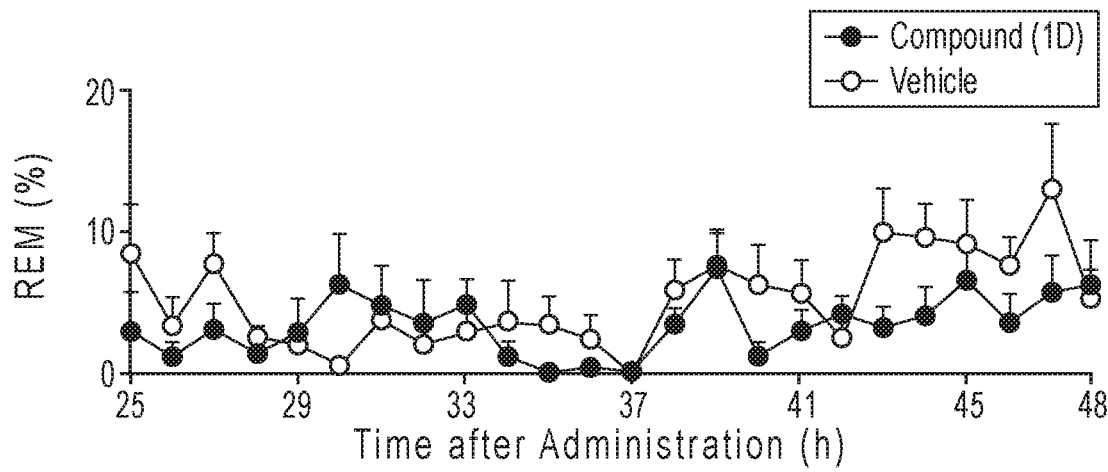
FIG. 11B shows a graph of the effects of 30 mg/kg/day of Compound (1D) on rat REM sleep during the 24 hour period on Day 8.
Figure 11C:
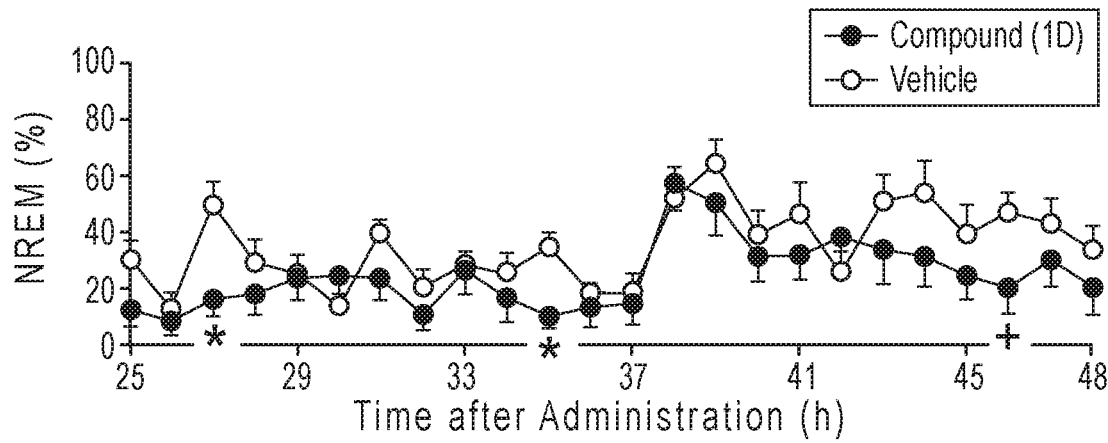
FIG. 11C shows a graph of the effects of 30 mg/kg/day of Compound (1D) on rat NREM sleep during the 24 hour period on Day 8.
Figure 12A:
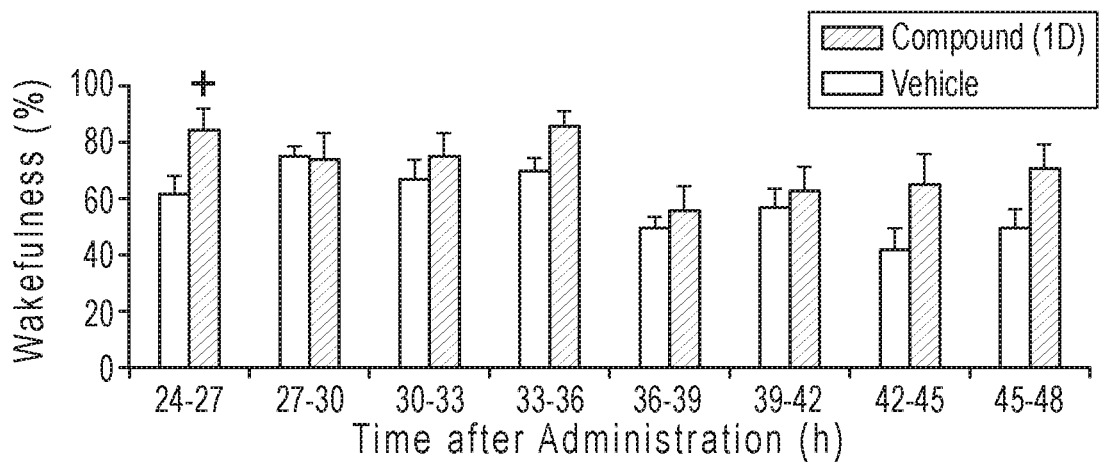
FIG. 12A shows a bar chart summarizing the effects of 30 mg/kg/day of Compound (1D) on rat wakefulness every 3 hours during the 24 hour period on Day 8.
Figure 12B:
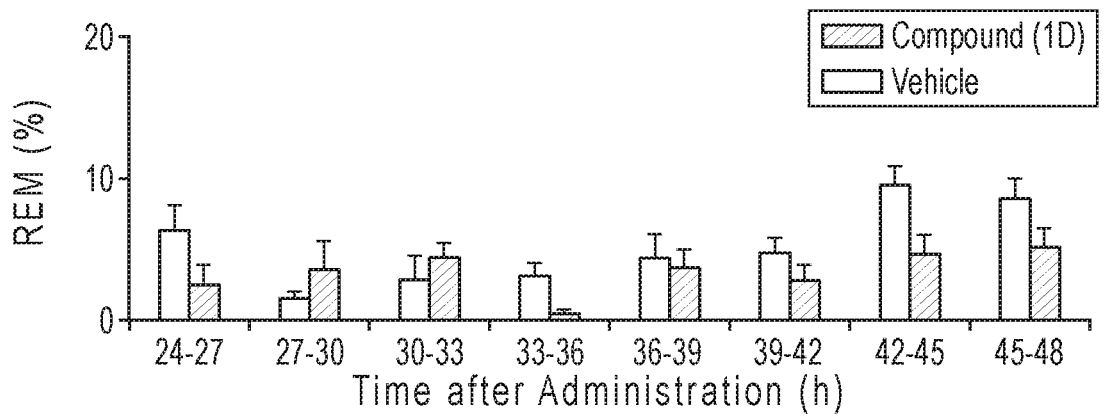
FIG. 12B shows a bar chart summarizing the effects of 30 mg/kg/day of Compound (1D) on rat REM sleep every 3 hours during the 24 hour period on Day 8.
Figure 12C:
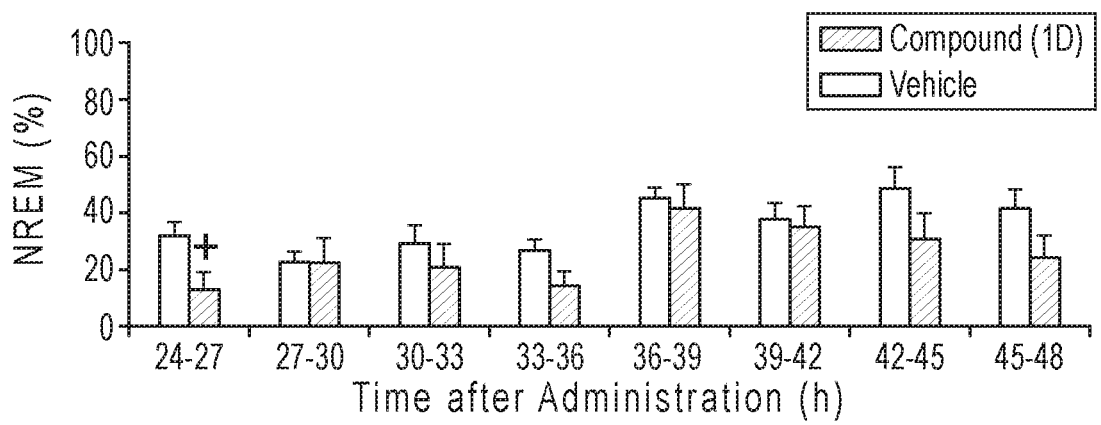
FIG. 12C shows a bar chart summarizing the effects of 30 mg/kg/day of Compound (1D) on rat NREM sleep every 3 hours during the 24 hour period on Day 8.

The data shown in FIG. 11A for Day 8, which began about 25 hours after the Day 7 final administration of Compound (1D), shows that the percentage of time spent in wakefulness was significantly increased at several time points, e.g., at 27, 35, and 46 hours, while, pursuant to FIG. 11C, the percentage of time spent in NREM sleep was significantly decreased at the same time points during the lights-out and lights-on periods when compared to vehicle group. These data might possibly be interpreted to suggest that repeated administration of 30 mg/kg/day of Compound (1D) for 7 days followed by a 1 day cessation of dosing induced Day 8 rebound insomnia in rats. However, such an interpretation is contradicted by other findings. For example, FIG. 11B illustrates that the prior administration of Compound (1D) had no effect in Day 8 on the time spent in REM sleep. Moreover, from FIGS. 12A-12C it can be noted that the prior administration of Compound (1D) had no significant effect during most of the lights-out period, having a significant effect only during the initial lights-out period (24-27 hours) in Day 8 on the percentage amounts of wakefulness and NREM sleep, increasing the former and decreasing the latter, respectfully.

6.15 Example 15: In Vivo Administration of Compound (1D) as Compared to Zolpidem Compound (1D) was administered in a 0.5 w/v % methylcellulose aqueous solution once orally to a rat population as described in Example 14 at a dose level of either 10 mg/kg or 100 mg/kg and its effects on brain waves (via EEG) and limb movements (via EMG) evaluated. Control rats received either the 0.5% MC vehicle or a positive control of 10 mg/kg of the sleep moderating drug zolpidem (Sigma-Aldrich Japan K.K., Tokyo) in 0.5% MC once orally in a similar manner. Note that, pursuant to the March 2017 prescribing information for zolpidem tartrate, the recommended human single-administration oral dose is either 5 or 10 mg, i.e., either 0.083 or 0.17 mg/kg, respectively, for a 60 kg human. An earlier study established that at a far greater 10 mg/kg zolpidem single oral dose, the induction of NREM sleep in rats was expected. Unless otherwise disclosed to the contrary in this example, the experimental procedures for this example were as described in Example 14.

EEG and EMG recording was begun 1 hour before dosing and continued for at least 24 hours after dosing. The cross-over experimental dosing design shown in Table 19 was used to assess the effects of Compound (1D) or zolpidem on the sleep-wake cycle by EEG/EMG analysis as compared with vehicle treated rats.

TABLE 19

Cross-over Experimental Dosing Design

| Period | Test Substance | Dose (mg/kg/day) | Group Designation/ Number of Rats |
|---|---|---|---|
| 15.1 | Vehicle | 0 | Group C/4 |
|  | Compound (1D) | 10 | Group D/4 |
| 15.2 | Compound (1D) | 10 | Group C/4 |
|  | Vehicle | 0 | Group D/4 |
| 15.3 | Vehicle | 0 | Group E/4 |
|  | Compound (1D) | 100 | Group F/3 |
| 15.4 | Compound (1D) | 100 | Group E/4 |
|  | Vehicle | 0 | Group F/3 |
| 15.5 | Vehicle | 0 | Group G/3 |
|  | Zolpidem | 10 | Group H/4 |
| 15.6 | Zolpidem | 10 | Group G/3 |
|  | Vehicle | 0 | Group H/4 |

A 7 day wash-out period was used between Periods 15.1 and 15.2, Periods 15.3 and 15.4, and Periods 15.5 and 15.6. The results obtained from the testing are illustrated in FIGS. 13-18. In FIGS. 13-18, the symbol+adjacent to a particular data point or bar indicates that, for that data point or bar, there is a significant difference from the vehicle by the unpaired student's t-test with p<0.05. Also in these figures, the symbol * adjacent to a particular data point or bar indicates that, for that data point or bar, there is a significant difference from the vehicle by the unpaired student's t-test with p<0.01 and the symbol A adjacent to a particular data point or bar indicates that, for that data point or bar, there is a significant difference from the vehicle by the unpaired student's t-test with p<0.001.

Figure 13A:
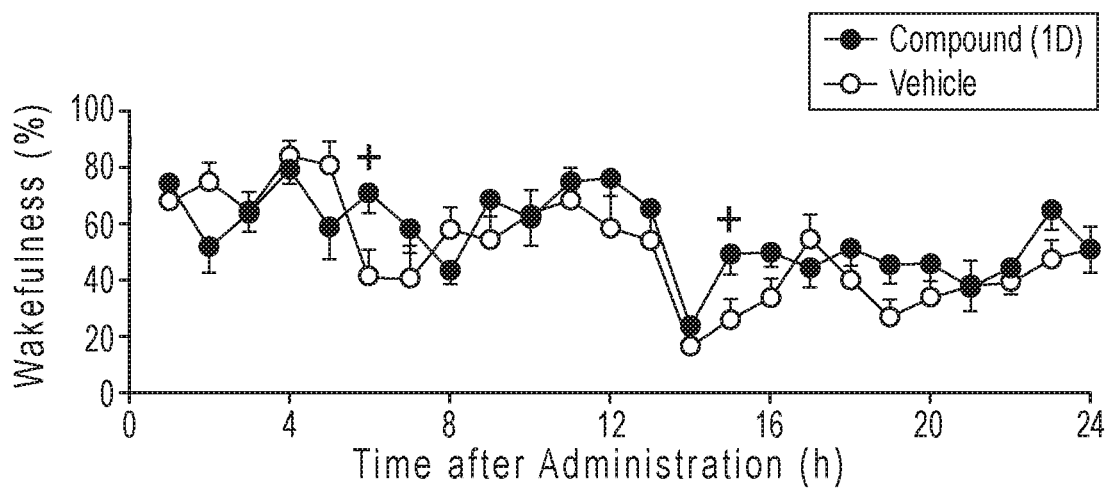
FIG. 13A shows a graph of the effects of 10 mg/kg of Compound (1D) on rat wakefulness during the 24 hour period after dosing.
Figure 13B:
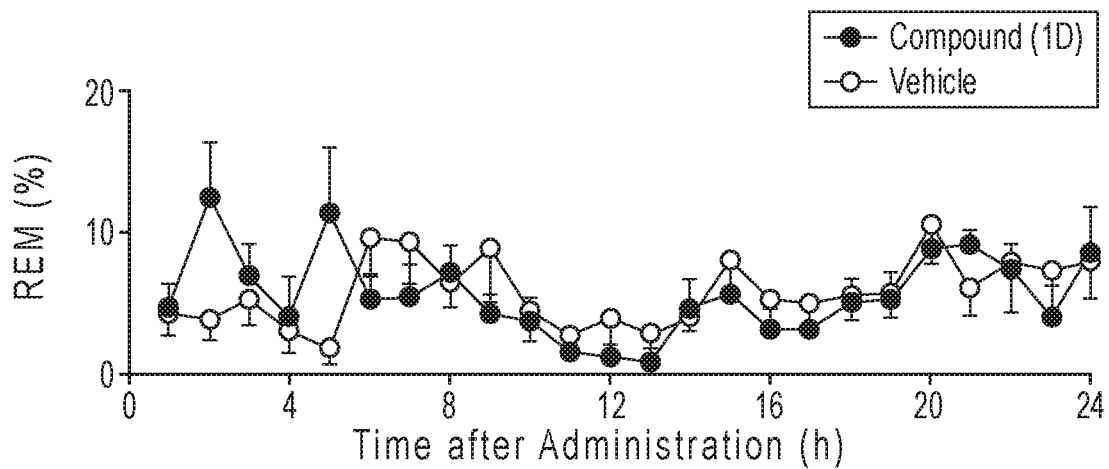
FIG. 13B shows a graph of the effects of 10 mg/kg of Compound (1D) on rat REM sleep during the 24 hour period after dosing.
Figure 13C:
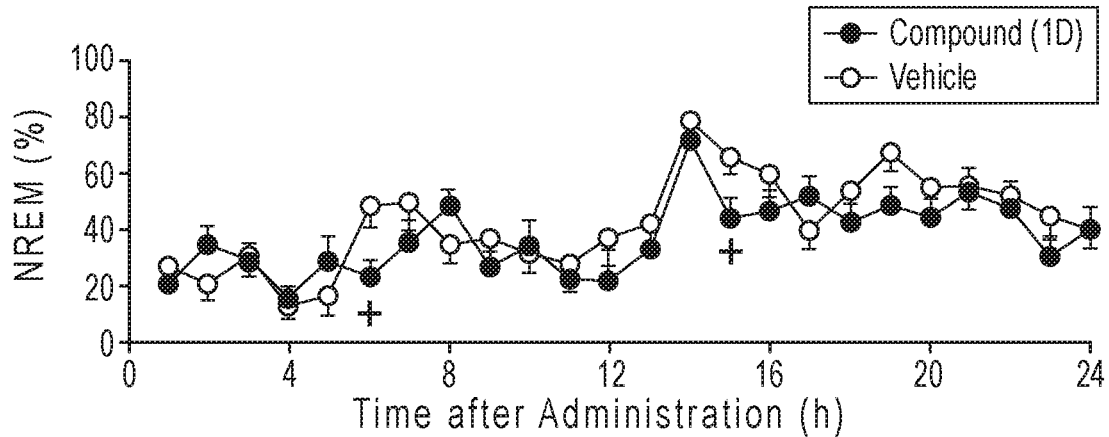
FIG. 13C shows a graph of the effects of 10 mg/kg of Compound (1D) on rat NREM sleep during the 24 hour period after dosing.
Figure 14A:
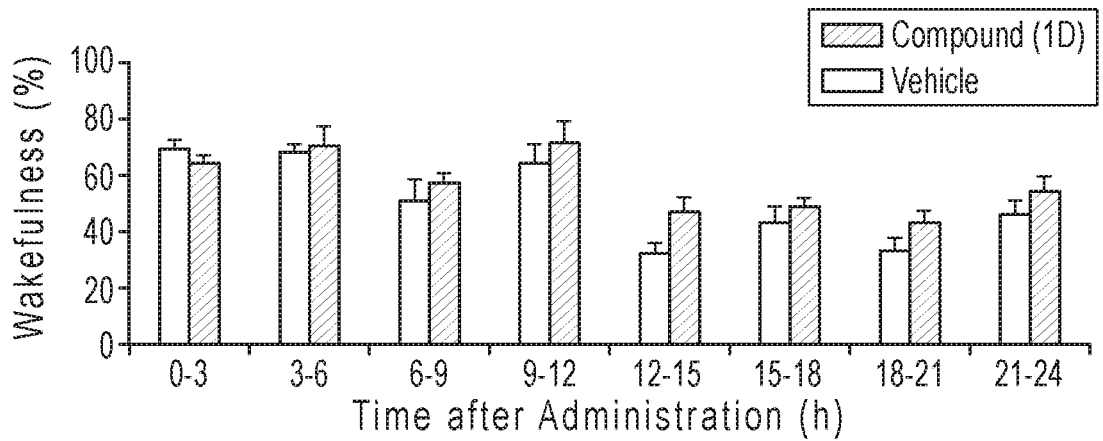
FIG. 14A shows a bar chart summarizing the effects of 10 mg/kg of Compound (1D) on rat wakefulness every 3 hours during the 24 hour period after dosing.
Figure 14B:
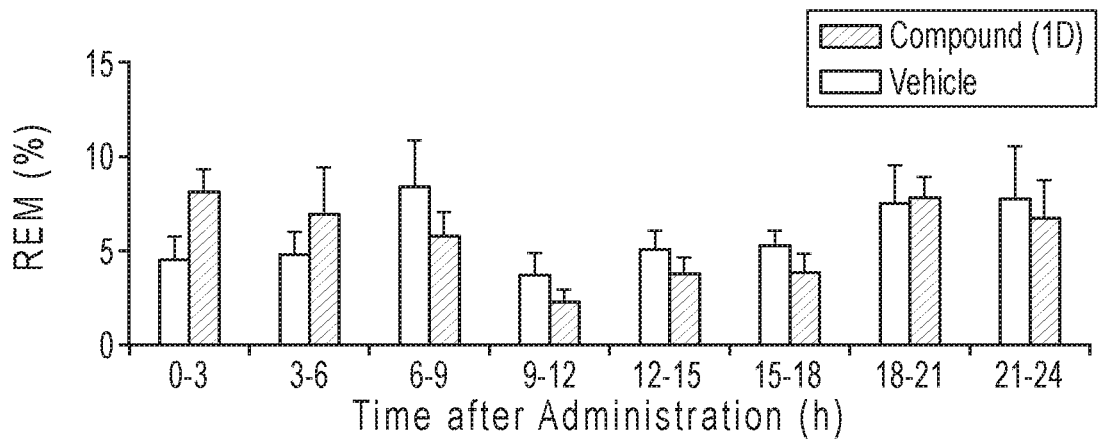
FIG. 14B shows a bar chart summarizing the effects of 10 mg/kg of Compound (1D) on rat REM sleep every 3 hours during the 24 hour period after dosing.
Figure 14C:
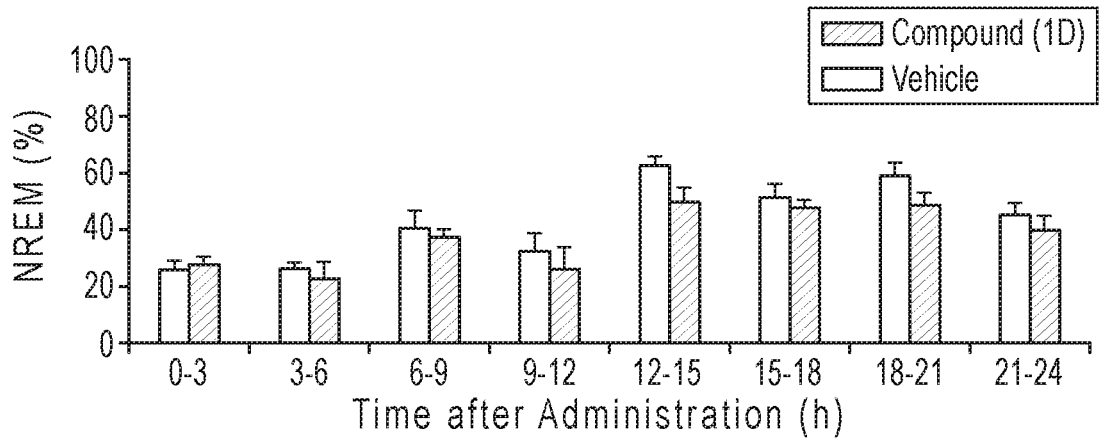
FIG. 14C shows a bar chart summarizing the effects of 10 mg/kg of Compound (1D) on rat NREM sleep every 3 hours during the 24 hour period after dosing.

At a 10 mg/kg dose of Compound (1D), FIG. 13A illustrates that the percentage of time spent in wakefulness, collected into 1 hour "time blocks", was lower at 2, 5, and 8 hours after dosing during the lights-out period with Compound (1D) relative to the vehicle group. However, wakefulness was significantly increased at 6 hours after dosing, i.e., during the lights-out period, and at 15 hours after dosing, i.e., during the lights-on period, when compared to the vehicle group. FIG. 13C illustrates that the percentage of time spent in NREM sleep was higher at 2, 5, and 8 hours after dosing with Compound (1D) relative to the vehicle group. However, NREM sleep was significantly decreased at 6 and 15 hours after dosing, when compared to the vehicle group. FIG. 13B illustrates that there were relatively minor effects and no significant effects on the percentage of time spent in REM sleep. There were also relatively minor effects and no significant changes in the percentage amounts of wakefulness, REM sleep, and NREM sleep when the data were collected into 3 hour "time blocks" as shown in FIGS. 14A-14C, respectfully. Collectively, these data suggested that the administration of a single 10 mg/kg dose of Compound (1D) had minor sleep-enhancing effects in rats.

Figure 15A:
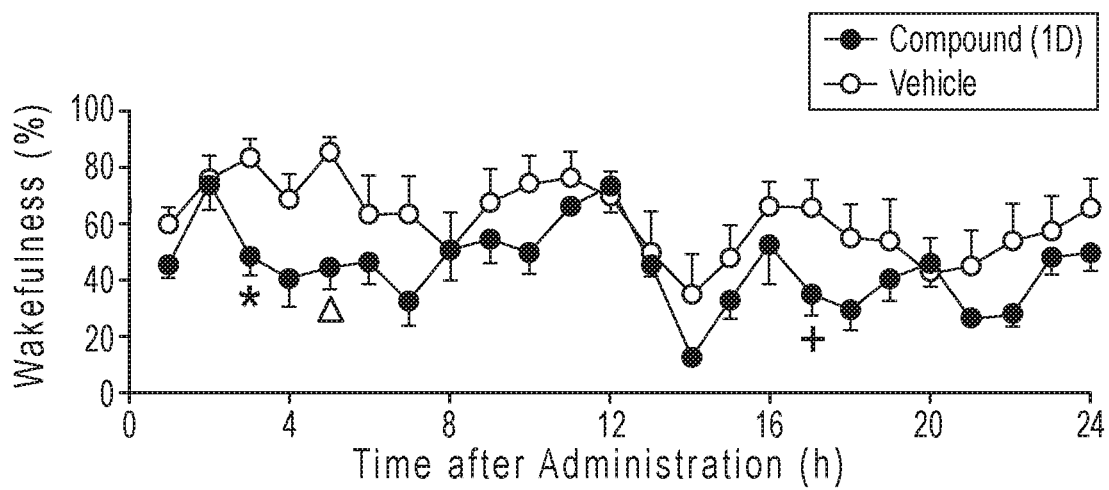
FIG. 15A shows a graph of the effects of 100 mg/kg of Compound (1D) on rat wakefulness during the 24 hour period after dosing.
Figure 15B:
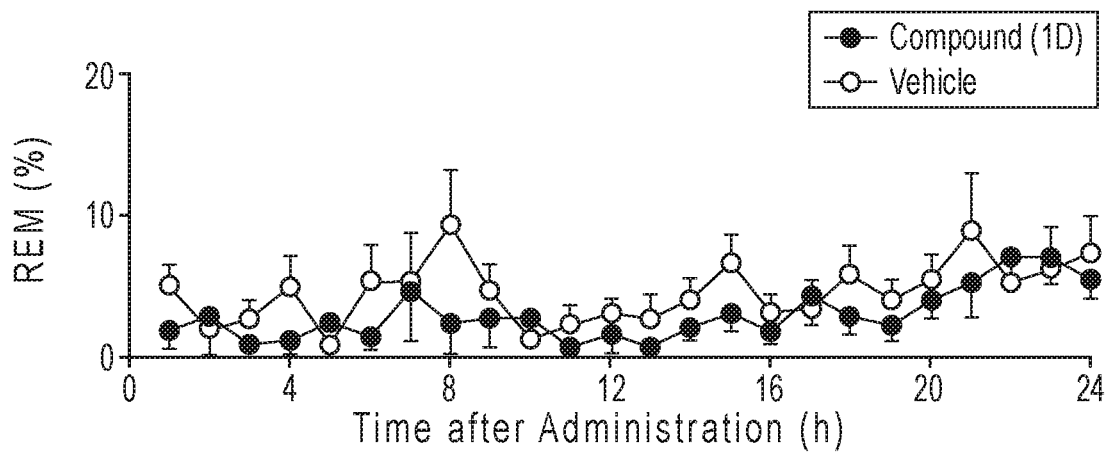
FIG. 15B shows a graph of the effects of 100 mg/kg of Compound (1D) on rat REM sleep during the 24 hour period after dosing.
Figure 15C:
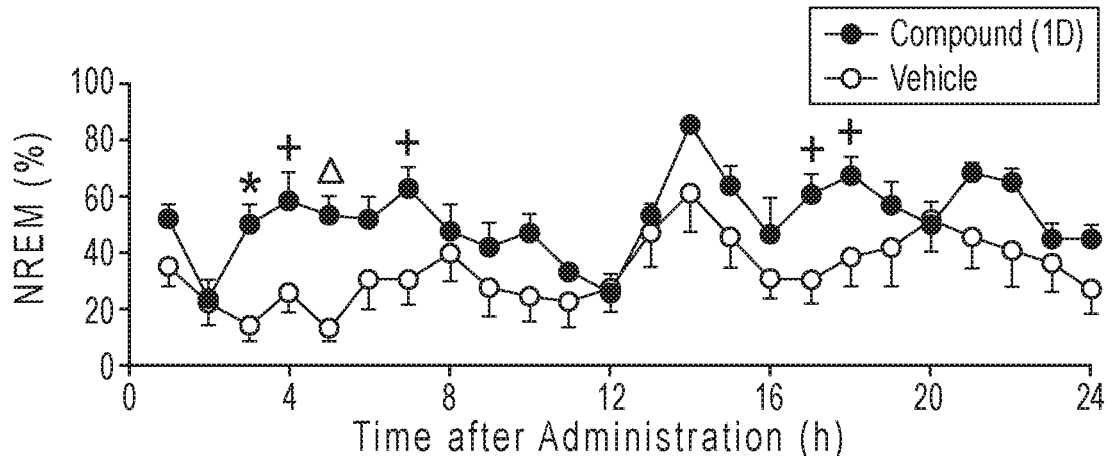
FIG. 15C shows a graph of the effects of 100 mg/kg of Compound (1D) on rat NREM sleep during the 24 hour period after dosing.
Figure 16A:
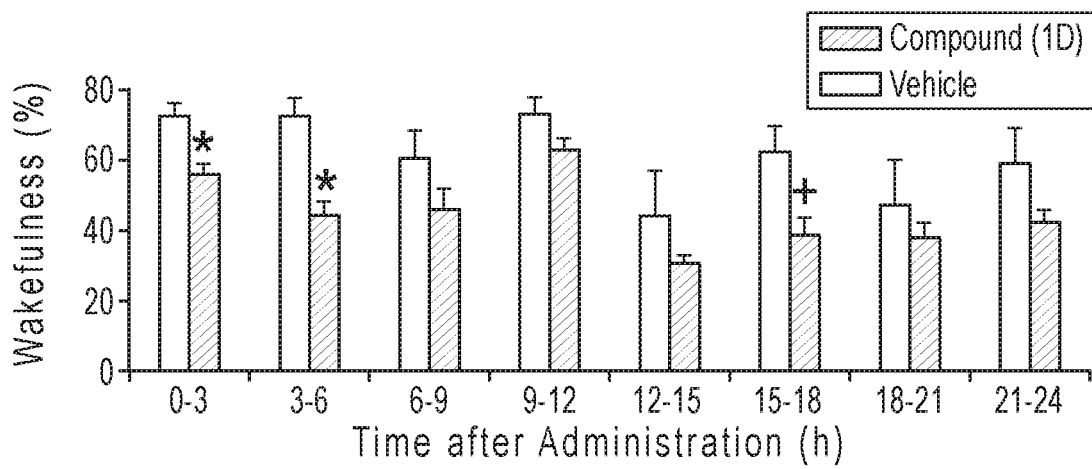
FIG. 16A shows a bar chart summarizing the effects of 100 mg/kg of Compound (1D) on rat wakefulness every 3 hours during the 24 hour period after dosing.
Figure 16B:
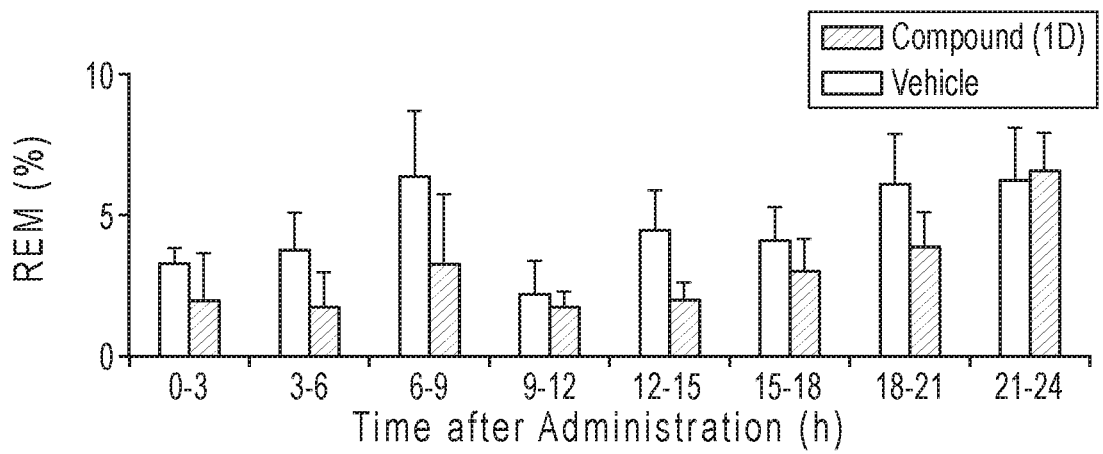
FIG. 16B shows a bar chart summarizing the effects of 100 mg/kg of Compound (1D) on rat REM sleep every 3 hours during the 24 hour period after dosing.
Figure 16C:
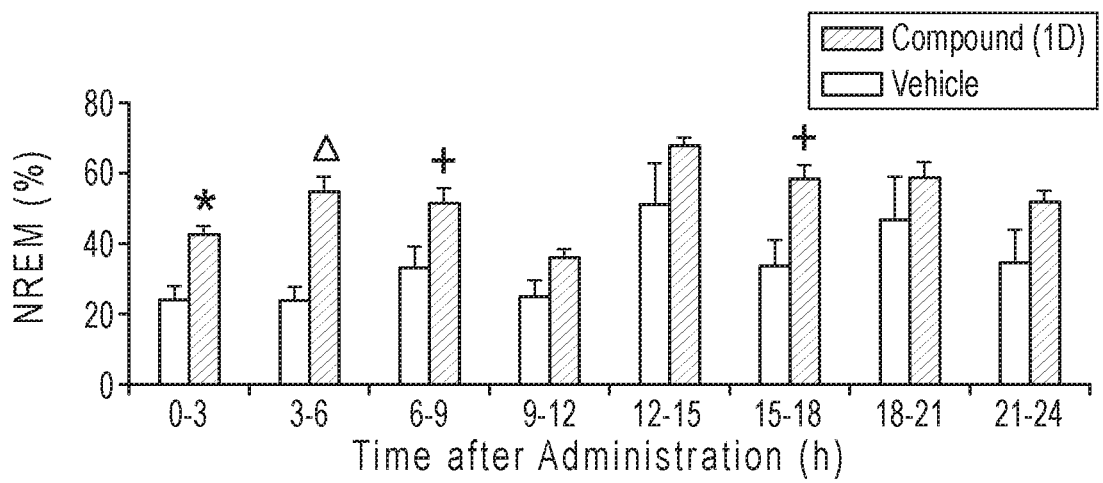
FIG. 16C shows a bar chart summarizing the effects of 100 mg/kg of Compound (1D) on rat NREM sleep every 3 hours during the 24 hour period after dosing.

At a 100 mg/kg dose of Compound (1D), FIG. 15A illustrates that the percentage of time spent in wakefulness was significantly decreased at 3 and 5 hours after dosing during the lights-out period and at 17 hours after dosing during the lights-on period, when compared to the vehicle group. FIG. 15C illustrates that the percentage of time spent in NREM sleep was significantly increased at 3, 4, 5, and 7 hours after dosing during the lights-out period and at 17 and 18 hours after dosing during the lights-on period, when compared to the vehicle group. FIG. 15B illustrates that there were relatively minor effects and no significant effects on the percentage of time spent in REM sleep. Comparable significant changes in the percentage amounts of wakefulness and NREM sleep were evident when the data were collected into 3 hour blocks as shown in FIGS. 16A and 16C, respectfully—significant increases in wakefulness at from 0-3, 3-6, and 15-18 hours and significant decreases in NREM sleep at from 0-3, 3-6, 6-9, and 15-18 hours. FIG. 16B illustrates that there were relatively minor effects and no significant effects on the percentage of time spent in REM sleep. Collectively, these data demonstrated that the administration of a single 100 mg/kg dose of Compound (1D) had significant sleep-enhancing effects in rats especially during the lights-out period.

Figure 17A:
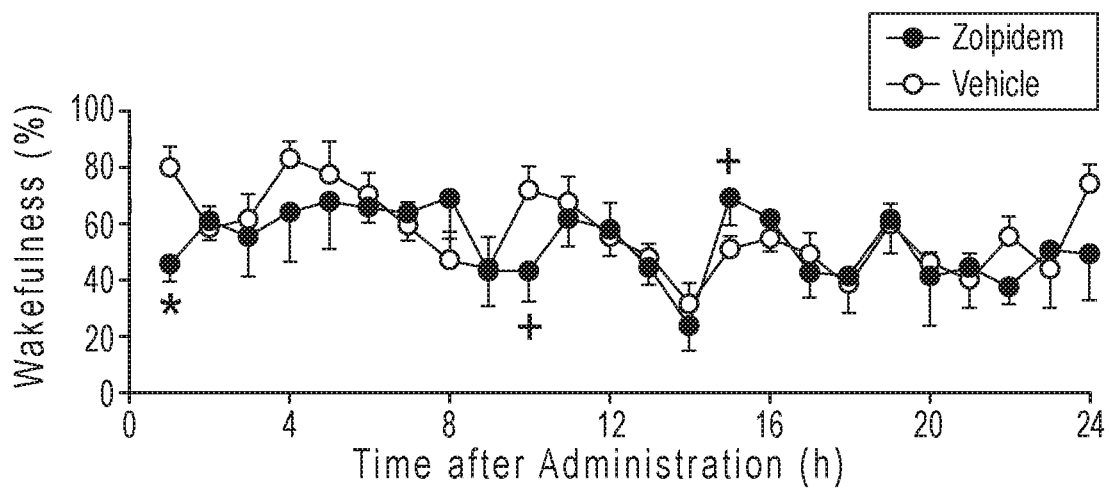
FIG. 17A shows a graph of the effects of 10 mg/kg zolpidem on rat wakefulness during the 24 hour period after dosing.
Figure 17B:
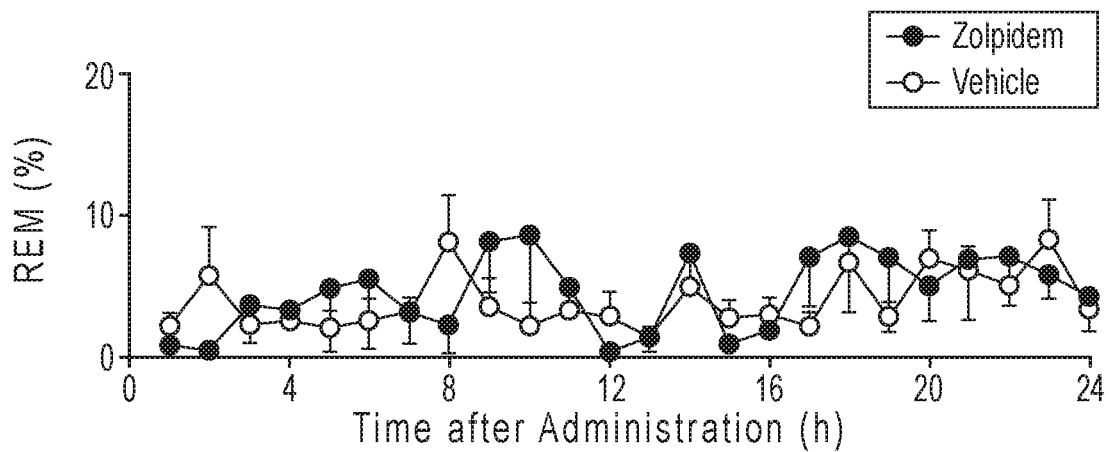
FIG. 17B shows a graph of the effects of 10 mg/kg zolpidem on rat REM sleep during the 24 hour period after dosing.
Figure 17C:
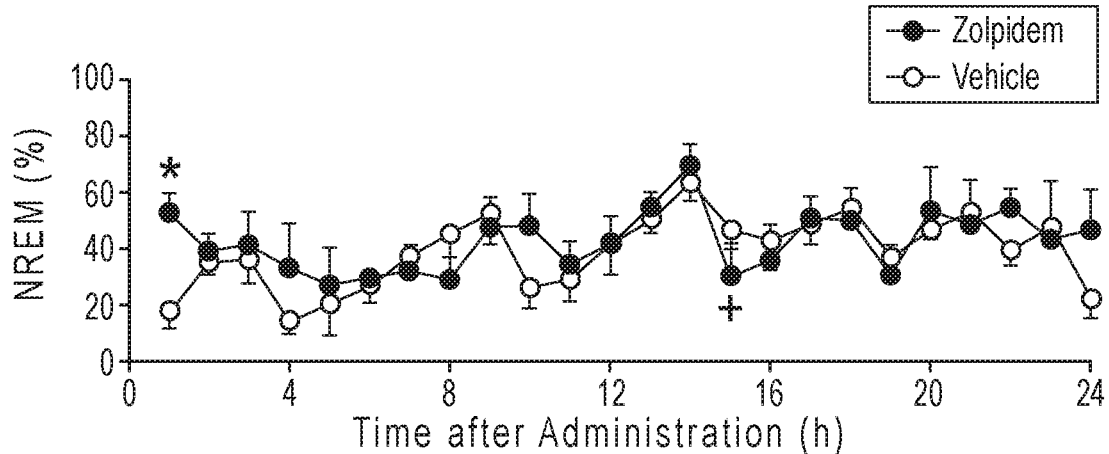
FIG. 17C shows a graph of the effects of 10 mg/kg zolpidem on rat NREM sleep during the 24 hour period after dosing.
Figure 18A:
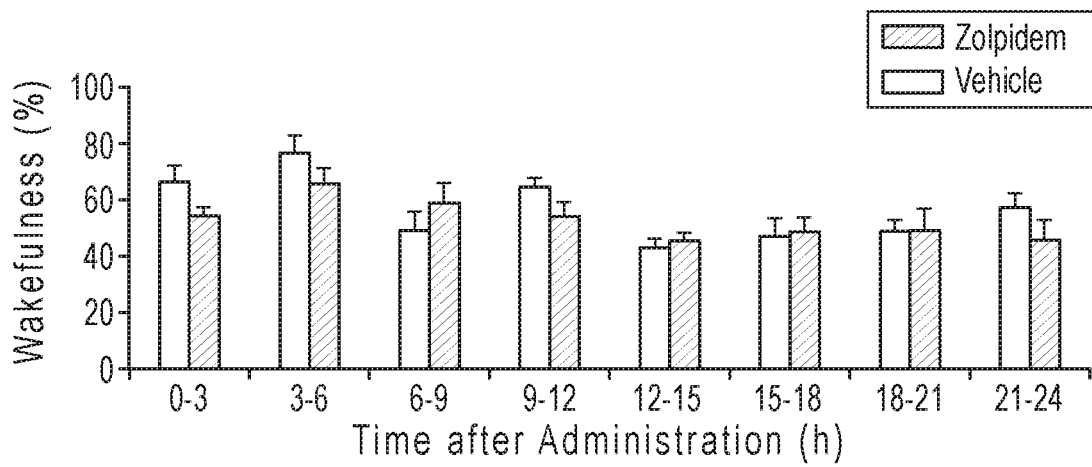
FIG. 18A shows a bar chart summarizing the effects of 10 mg/kg zolpidem on rat wakefulness every 3 hours during the 24 hour period after dosing.
Figure 18B:
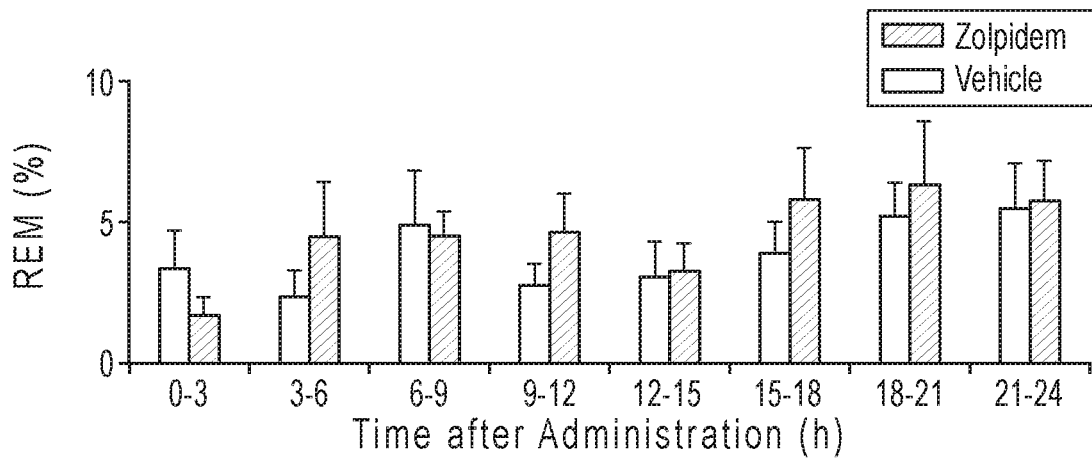
FIG. 18B shows a bar chart summarizing the effects of 10 mg/kg zolpidem on rat REM sleep every 3 hours during the 24 hour period after dosing.
Figure 18C:
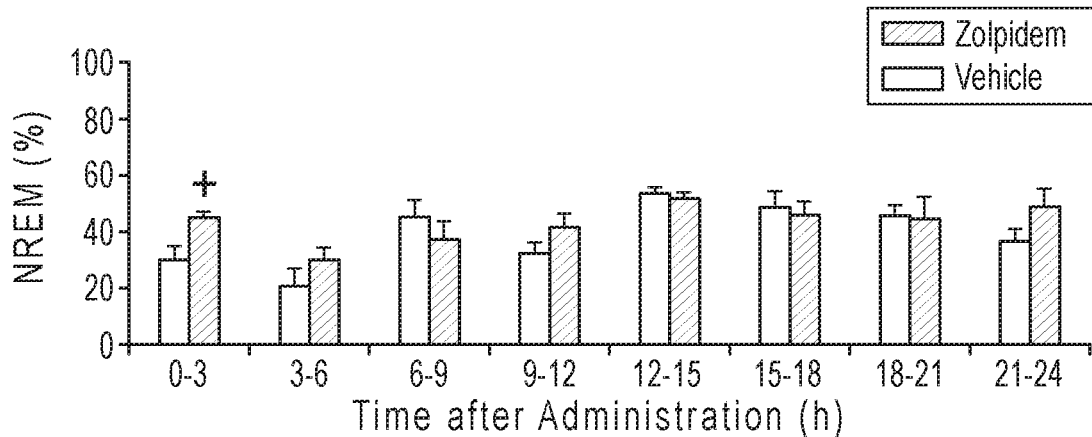
FIG. 18C shows a bar chart summarizing the effects of 10 mg/kg zolpidem on rat NREM sleep every 3 hours during the 24 hour period after dosing.

At a 10 mg/kg dose of zolpidem, FIG. 17A illustrates that the percentage of time spent in wakefulness was significantly decreased at 1 and 10 hours after dosing during the lights-out period—about 46% and 43%, respectively—when each is compared to the vehicle group (about 79% and 71%, respectively). Additionally, the percentage of time spent in wakefulness significantly increased at 15 hours after dosing during the lights-on period—about 69%—when compared to the vehicle group (about 51%). FIG. 17C illustrates that the percentage of time spent in NREM sleep was significantly increased during the lights-out period at 1 hour after dosing and significantly decreased during the lights-on period at 15 hours after dosing—about 53% and 30%, respectively—when compared to the vehicle group (about 18% and 47%, respectively). FIG. 17B illustrates that there were relatively minor effects and no significant effects on the percentage of time spent in REM sleep. FIGS. 18C and 18A, respectively, where the data were collected into 3 hour blocks, confirm the significant increase in NREM sleep at 0-3 hours after dosing and illustrate a decreased tendency in wakefulness over the period between 0-12 hours after administration, when compared to the vehicle group. FIG. 18B illustrates that there were relatively minor effects and no significant effects on the percentage of time spent in REM sleep. Collectively, these results demonstrated that a single zolpidem dose of 10 mg/kg provided a sleep-enhancing effect and induced sleep during the lights-out period. These results also demonstrated that the experiments performed under these conditions were sufficiently sensitive to detect the sleep-enhancing effects of Compound (1D) in rats.

6.16 Example 16: Safety Factor of Compound (1D)

Example 13 demonstrated that, because there were no effects on the general physical condition or behavior of rats even at a dose of up to 600 mg/kg, the NOAEL of Compound (1D) was at least 600 mg/kg. In contrast to Example 15, which showed a 10 mg/kg dose of Compound (1D) had minor sleep-enhancing effects, Example 14 demonstrated that Compound (1D) was effective in mitigating insomnia/inducing NREM sleep at a dose of 30 mg/kg. From the data provided by these examples, it can be determined that the safety factor for Compound (1D) is at least 20 fold, i.e., (>600 mg/kg)/30 mg/kg.

6.17 Example 17: Binding Efficacy and Activity Response of Compounds (1C), 405, and W-212393

The binding efficacy, of Compound (1C) or 405, the free acid and free base forms of these compounds, to the ORL-1, mu-opioid, kappa-opioid, and delta-opioid receptors was determined in Example 18 of U.S. Pat. No. 8,476,271 by radioligand dose-displacement assays. Similarly, the binding efficacy of Compound W-212393, the free base form of this compound, to the ORL-1 receptor was determined according to the procedures provided in Example 18 of U.S. Pat. No. 8,476,271 and in the Examples therein to which it refers, all of which are hereby incorporated by reference in their entirety. The binding efficacy results are summarized in Table 20.

TABLE 20

Efficacy of Receptor Binding

| | $K_i$ (nM) [Average ± SD] | | | |
| | | Opioid Receptor | | |
| Test Substance | ORL-1 | Mu | Kappa | Delta |
| Compound (1C) | 2.4 ± 0.2 | 1631 ± 77 | 2280 ± 213 | 4763 ± 509 |
| Compound 405 | 1.1 ± 0.1 | 61.6 ± 8.7 | 75.4 ± 7.8 | 691 ± 57 |
| Compound W-212393 | 0.7 ± 0.1 | ND | ND | ND |

ND = Not determined

The activity response of Compounds (1C) and 405 to the ORL-1, mu-opioid, and kappa-opioid receptors was determined in Example 18 of U.S. Pat. No. 8,476,271 by functional [$^{35}$S]GTPγS binding assays. Similarly, the activity response of Compound W-212393 to the ORL-1 receptor was determined according to the procedures provided in Example 18 of U.S. Pat. No. 8,476,271 and in the Examples therein to which it refers, all of which are hereby incorporated by reference in their entirety. The activity response results are summarized in Table 21.

TABLE 21

Activity Response

GTPγS ($EC_{50}$: nM, Emax: %) [Mean ± Standard Error of the Mean]

| Test Substance | ORL-1 | | Opioid Receptor | | | |
|---|---|---|---|---|---|---|
| | $EC_{50}$ | $E_{max}$ | Mu | | Kappa | |
| | | | $EC_{50}$ | $E_{max}$ | $EC_{50}$ | $E_{max}$ |
| Compound (1C) | 4.03 ± 0.86 | 47.8 ± 1.3 | >20,000 | 0 | >20,000 | 3.0 ± 0.6 |
| Compound 405 | 0.55 ± 0.1 | 47.5 ± 3.5 | >20,000 | 0 | >20,000 | 0 |
| Compound W-212393 | 2.04 ± 0.14 | 102.7 ± 0.3 | ND | ND | ND | ND |

ND = Not determined

It can be noted from the ORL-1 $E_{max}$ results in Table 21 that Compounds (1C) and 405, with values of about 47-48%, are each partial agonists. In contrast, Compound W-212393, having an $E_{max}$ of about 103%, is an agonist, i.e., a full agonist.

6.18 Example 18: In Vivo Plasma Concentration in of Compound (1D) in Humans

The plasma concentration of Compound (1D) was evaluated in humans for up to 36 hours after administration of a single oral dose of 3, 10, or 30 mg of Compound (1D) in the form of a methyl cellulose suspension. Four healthy male subjects were administered each dose.

Figure 19A:
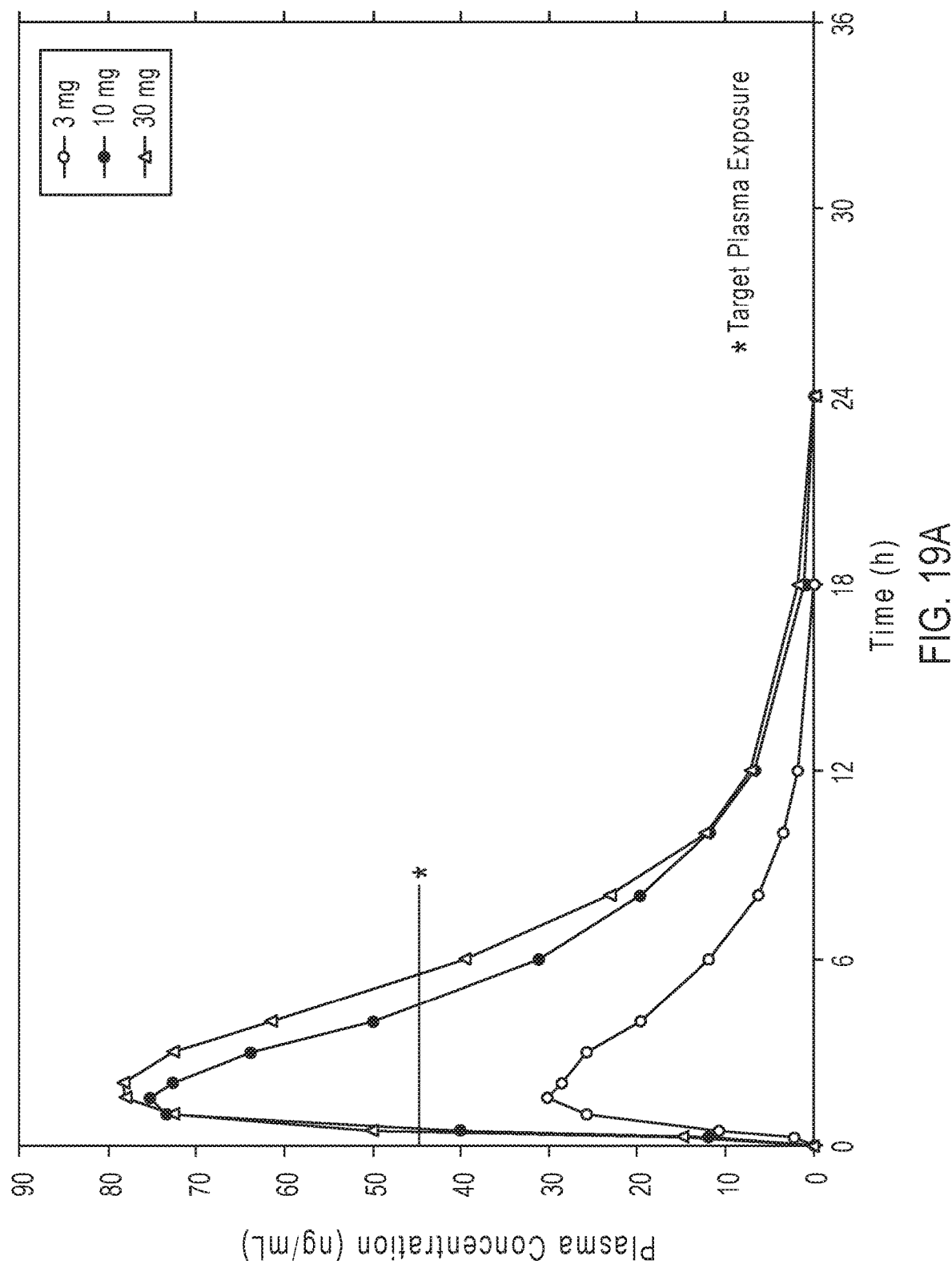
FIG. 19A shows a graph of the human plasma concentration of Compound (1D) on a linear scale versus linear time after the administration at three different single doses.
Figure 19B:
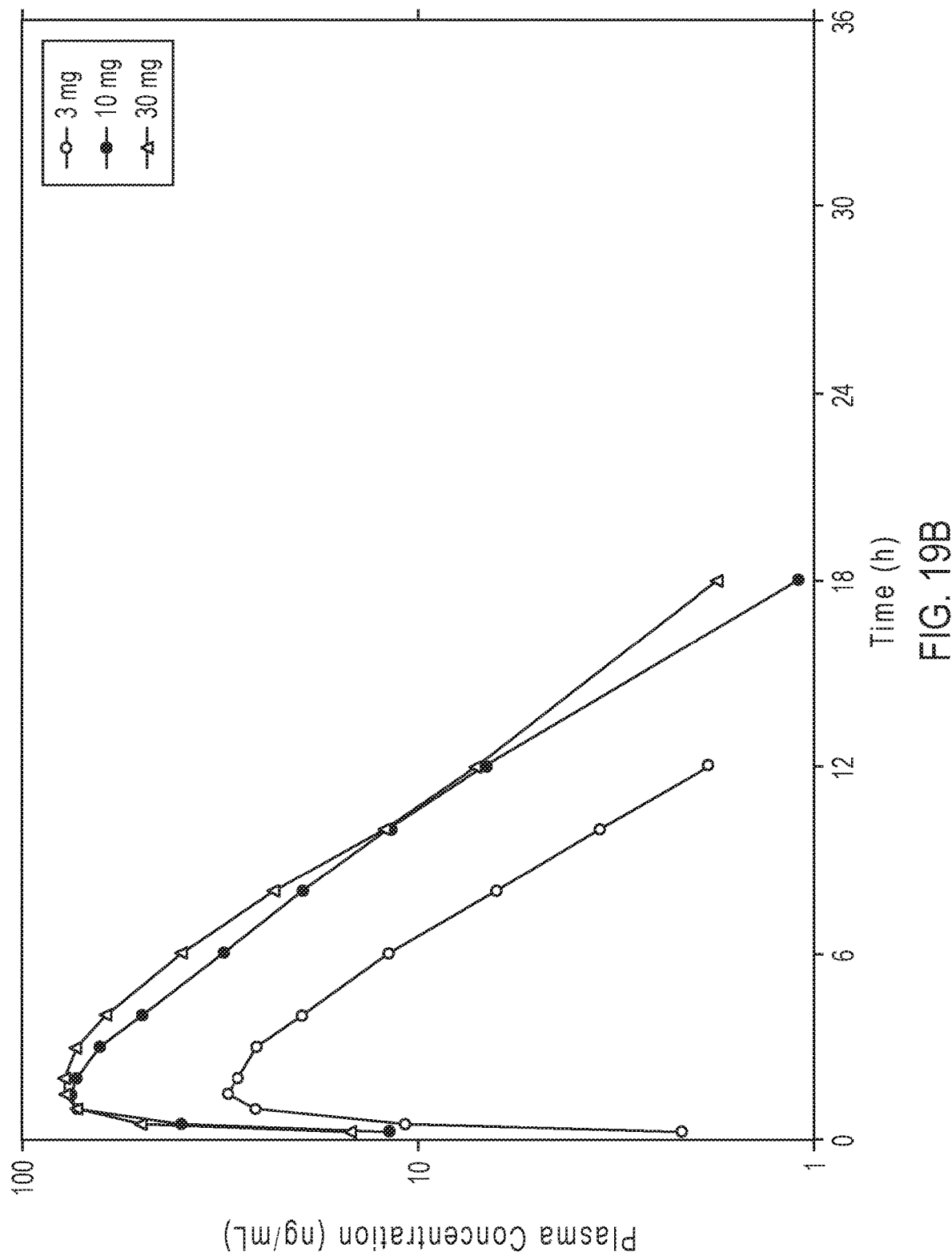
FIG. 19B shows a graph of the human plasma concentration of Compound (1D) on a logarithmic scale versus linear time after the administration at three different single doses.

FIG. 19A provides a plot of the human plasma concentration of Compound (1D) on a linear scale versus linear time in hours at each dose: 3, 10, and 30 mg. FIG. 19B provides the same results in a plot of human plasma concentration of Compound (1D) on a logarithmic scale versus linear time at each dose. The target plasma exposure indicated in FIG. 19A relates to the effective dose in 80% of subjects from rat modeling results.

The pharmacokinetic information obtained from such plots is summarized in Table 22 below, where $AUC_t$ represents the area under the curve determined from the time of administration to the final scheduled sampling time point where the an increase in the area was measurable (i.e., 12 h at the 3 mg dose, 18 hours for 3 of the 4 subjects at the 10 mg dose (12 h for the other subject), and 18 h at the 30 mg dose); $AUC_{inf}$ represents the area under the curve determined from the time of administration to an extrapolation to infinite time; $C_{max}$ is the maximum plasma concentration of Compound (1D); $t_{max}$ is the time at which $C_{max}$ is achieved; $t_{1/2}$ is the half-life; and CV % is the coefficient of variation in percent.

TABLE 22

Pharmacokinetic Summary Statistics for Human Administration of Compound (1D)

| Compound (1D) Dose | | 3 mg | 10 mg | 30 mg |
|---|---|---|---|---|
| $AUC_t$ (ng h/mL) | Mean | 154 | 438 | 505 |
| | SD | 14 | 107 | 140 |
| | Minimum | 135 | 300 | 388 |
| | Maximum | 168 | 550 | 708 |
| | CV % | 9.1 | 24 | 28 |
| $AUC_{inf}$ (ng h/mL) | Mean | 161 | 447 | 512 |
| | SD | 14 | 101 | 139 |
| | Minimum | 144 | 320 | 398 |
| | Maximum | 176 | 557 | 714 |
| | CV % | 8.7 | 23 | 27 |

TABLE 22-continued

Pharmacokinetic Summary Statistics for Human Administration of Compound (1D)

| Compound (1D) Dose | | 3 mg | 10 mg | 30 mg |
|---|---|---|---|---|
| $C_{max}$ (ng/mL) | Mean | 30 | 77 | 83 |
| | SD | 5 | 17 | 17 |
| | Minimum | 23 | 56 | 69 |
| | Maximum | 34 | 98 | 106 |
| | CV % | 17 | 22 | 21 |
| $t_{max}$ (hours) | Mean | 1.6 | 1.5 | 1.8 |
| | SD | 0.25 | 0.4 | 1.0 |
| | Minimum | 1.5 | 1.0 | 1.0 |
| | Median | 1.5 | 1.5 | 1.5 |
| | Maximum | 2.0 | 2.0 | 3.0 |
| $t_{1/2}$ (hours) | Mean | 2.3 | 2.6 | 2.8 |
| | SD | 0.3 | 0.3 | 0.3 |
| | Minimum | 2.1 | 2.4 | 2.6 |
| | Maximum | 2.6 | 3.0 | 3.2 |

The results in Table 22 demonstrate that there was rapid gastrointestinal absorption of Compound (1D) across the three doses. In particular, the mean $t_{max}$ was similar across the three doses, i.e., 1.6, 1.5 and 1.8 hours, and ranged from a minimum of about 1 hour to a maximum of about 3 hours. The results in Table 22 also demonstrate that there was a short terminal elimination half-life. In particular, the mean $t_{1/2}$ was short and similar across the three doses, i.e., 2.3, 2.6 and 2.8 hours, and ranged from a minimum of about 2.1 hours to a maximum of about 3.2 hours.

6.19 Example 19: In Vivo Clearance of Radiolabeled Compound (1D) in Animals

The clearance of Compound (1D) from rats, dogs, and monkeys was determined by analyzing excreta samples from the animals (and controls as required) for a radiolabeled form of the compound.

Specifically, liquid scintillation counting ("LSC") was used for the determination of total radiolabeled Compound (1D) material, i.e., the original or parent compound and its metabolites. The radiolabeled Compound (1D) that was synthesized comprised $^{14}C$ as a phenyl group carbon atom of the quinoxaline skeleton of the molecule and is denoted herein as [$^{14}C$]-Compound (1D). Using $^{14}C$ as a radiolabel for pharmacokinetic studies is a recognized technique and embedding the radiolabel into the ring structure was done to limit migration or exchange of the radiolabel to non-Compound (1D)-related molecules. The specific radioactivity for the lot of [$^{14}C$]-Compound (1D) synthesized was 2.50 MBq/mg (67.6 µCi/mg) [3.49 MBq/mg (94.4 µCi/mg) if the material were to be present as the free base form] with a radiochemical purity of greater than 98.5% as determined by HPLC. The synthesized radiolabeled [$^{14}$C]-Compound (1D) was stored away from light at a temperature of −80° C. before use.

Following oral administration of [$^{14}$C]-Compound (1D) (in an appropriate vehicle, e.g., a methyl cellulose suspension) to the experimental animals, excreta samples were collected over specified time intervals. Urine samples were collected at fixed intervals post dosing. Fecal samples were homogenized and diluted prior to being solubilized. Aliquots of these samples were counted following the addition of liquid scintillation fluid thereto. Detection limits for radioactivity in the excreta samples were set at twice the background count (from blank samples) as determined by LSC. The [$^{14}$C]-Compound (1D) was stable for about 4-5 hours in urine at a temperature of about 25° C. and, when kept refrigerated at 4° C., for up to 15 days (rat urine) and 36 days (dog urine). Recovery of [$^{14}$C]-Compound (1D) from rat urine was typically from about 91.6 to about 99.1%. Recovery of [$^{14}$C]-Compound (1D) from dog urine was typically from about 100.9 to about 105.0%.

Oral doses of [$^{14}$C]-Compound (1D) given to rats were rapidly absorbed, widely distributed, and rapidly eliminated. The organs with the highest [$^{14}$C]-Compound (1D) burden following oral dosing of rats were the liver and kidney. However, it should be noted from Example 8 herein that although the radiolabeled compound appeared in rat livers because of the high blood flow therein, the non-radiolabeled Compound (1F) was negligibly metabolized by either rat liver microsomes or human liver microsomes. Only trace levels (below the limit of quantification) of [$^{14}$C]-Compound (1D)-derived radioactivity were found in any rat tissues 72 hours post dose.

There were no major metabolites of [$^{14}$C]-Compound (1D) detected in all species tested. Only a few minor metabolites were identified by high performance liquid chromatography with tandem mass spectrometry detection ("HPLC-MS-MS") in animal bile, urine, and feces. These metabolites were the 6-hydroxide, the 1-hydroxide, the decarboxylate, and the +2 form of [$^{14}$C]-Compound (1D).

In a one week study, the elimination of [$^{14}$C]-Compound (1D) was largely through feces in male rats and monkeys but through both the urine and feces in dogs; Table 23 below provides a summary of the results where the average % elimination is determined from the average of the ratio of the recovered $^{14}$C amount to amount of $^{14}$C administered as [$^{14}$C]-Compound (1D).

TABLE 23

% Elimination of [$^{14}$C]-Compound (1D)-Derived Radioactivity Within 168 Hours of Oral Dosing

| Elimination Route | Average % Elimination | | |
|---|---|---|---|
| | Rat (male)[a] | Monkey (female) | Dog (male) |
| Fecal[b] | 84.1 | 81.3 | 46.3 |
| Urinary | 14.9 | 20.7 | 50.3 |
| Fecal + Urinary | 99.0 | 102.0 | 96.6 |

[a] Renal drug clearance in female rats is about twice that of males.
[b] Includes unabsorbed and biliary excreted drug In a shorter duration study, female rats eliminated more of Compound (1D) via the urine than male rats; Table 24 below summarizes these results.

TABLE 24

% Elimination of Compound (1D)-Derived Radioactivity Within 48 Hours of Oral Dosing

| Elimination Route | Average % Elimination | |
|---|---|---|
| | Rat (male) | Rat (female) |
| Fecal | 41.6 | 27.9 |
| Urinary | 54.4 | 66.8 |
| Fecal + Urinary | 96.0 | 94.7 |

However, it should be noted from the data in Table 24 that the total amount eliminated was substantially identical for male and female rats.

As can be noted from this example, the total average % elimination was extremely high for all species tested, ranging from a low value of about 95% to essentially 100%. In summary, as is evident from the results in this example, [$^{14}$C]-Compound (1D) was poorly metabolized in vivo in all animal species tested.

6.20 Example 20: In Vivo Renal Clearance of Compound (1D) in Humans

The renal clearance of Compound (1D) was evaluated in humans for up to 36 hours after administration of a single oral dose of 3, 10, or 30 mg of Compound (1D) in the form of a methyl cellulose suspension. Four healthy male subjects were administered each dose. Table 25 below provides the results in the form of the mean renal clearance, mean total amount excreted unchanged ad Compound (1D), and mean percentage dose excreted unchanged.

TABLE 25

Renal Clearance and Elimination of Compound (1D)

| Dose (mg) | Mean Renal Clearance (mL/minute) | Mean Total Amount Excreted Unchanged (mg) | Mean % Dose Excreted Unchanged |
|---|---|---|---|
| 3.0 | 275 | 2.66 | 89 |
| 10 | 266 | 6.95 | 70 |
| 30 | 270 | 8.37 | 28 |

The results in Table 25 demonstrated that Compound (1D) was excreted largely unchanged in human urine. Additionally, there was active renal tubular secretion in addition to glomerular filtration. In particular, a 3 mg oral dose of Compound (1D) was essentially completely absorbed from an aqueous suspension from the gastrointestinal tract and, for the 3 and 10 mg doses, there was relatively rapid absorption and elimination of Compound (1D).

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:

1. A method for treating a sleep disorder, comprising administering to a human patient in need thereof from about 0.05 mg to about 100 mg of a compound of Formula (1)

(1)

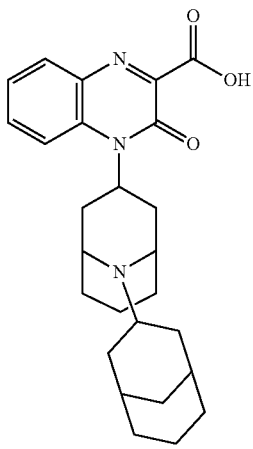

or a pharmaceutically acceptable salt thereof.

2. The method of claim 1, wherein the compound is a compound of Formula (1A)

(1A)

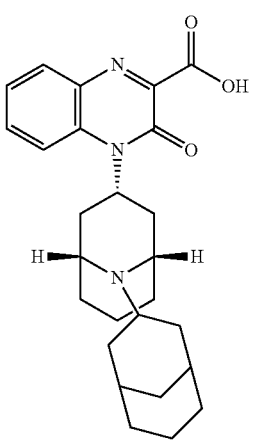

or a pharmaceutically acceptable salt thereof.

3. The method of claim 1, wherein the compound is a compound of Formula (1B)

(1B)

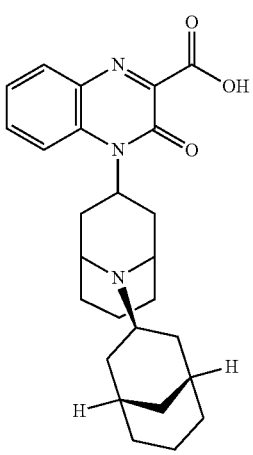

or a pharmaceutically acceptable salt thereof.

4. The method of claim 1, wherein the compound is a compound of Formula (1C)

(1C)

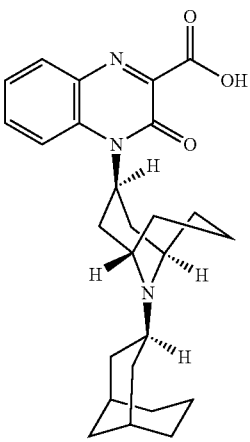

or a pharmaceutically acceptable salt thereof.

5. The method of claim 1, wherein the sleep disorder is an insomnia condition, a hypersomnia condition, a circadian rhythm sleep-wake disorder, an alcohol-induced sleep disorder, or any combination thereof.

6. The method of claim 5, wherein the alcohol-induced sleep disorder is insomnia-type alcohol-induced sleep disorder, daytime sleepiness type alcohol-induced sleep disorder, parasomnia type alcohol-induced sleep disorder, mixed type alcohol-induced sleep disorder, insomnia in alcohol use disorder, a sleep disorder associated with alcohol cessation, insomnia associated with alcohol cessation, or any combination thereof.

7. The method of claim 1, wherein administration of the compound of Formula (1) or a pharmaceutically acceptable salt thereof is by at least one route selected from oral, parenteral, intravenous, intramuscular, buccal, gingival, sublingual, intraocular, transdermal, and transmucosal.

8. The method of claim 7, wherein administration of the compound of Formula (1) or a pharmaceutically acceptable salt thereof is by oral, sublingual, gingival, or buccal administration.

9. The method of claim 1, wherein said administration is a single daily human dose of the compound of Formula (1) or a pharmaceutically acceptable salt thereof from about 0.10 mg to about 15 mg.

10. The method of claim 9, wherein the single daily human dose of the compound of Formula (1) or a pharmaceutically acceptable salt thereof is from about 0.2 mg to about 6.0 mg.

11. The method of claim 1, wherein said administration is a single daily dose of the compound of Formula (1) or a pharmaceutically acceptable salt thereof and is administered to the patient on at least two consecutive days; and wherein the patient exhibits an average improvement versus baseline in Total Sleep Time (TST), Sleep Efficiency (SE), Latency to Persistent Sleep (LPS), Total Wake Time (TWT), Wake During Sleep (WDS), Wake After Sleep Onset (WASO), Number of Awakenings (NAW), REM latency, or any combination thereof.

12. The method of claim 11, wherein the patient exhibits an average improvement in total sleep time, sleep efficiency, latency to persistent sleep, wake after sleep onset, or any combination thereof.

13. The method of claim 12, wherein the patient exhibits an average improvement in total sleep time, sleep efficiency, latency to persistent sleep, and wake after sleep onset.

14. A method for preventing a sleep disorder, comprising administering to a human patient in need thereof from about 0.05 mg to about 100 mg of a compound of Formula (1)

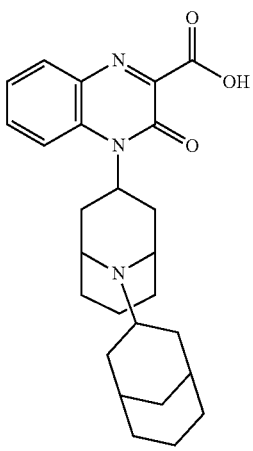

(1)

or a pharmaceutically acceptable salt thereof.

15. The method of claim 14, wherein the sleep disorder is an insomnia condition, a hypersomnia condition, a circadian rhythm sleep-wake disorder, an alcohol-induced sleep disorder, or any combination thereof.

16. The method of claim 15, wherein the alcohol-induced sleep disorder is insomnia-type alcohol-induced sleep disorder, daytime sleepiness type alcohol-induced sleep disorder, parasomnia type alcohol-induced sleep disorder, mixed type alcohol-induced sleep disorder, insomnia in alcohol use disorder, a sleep disorder associated with alcohol cessation, insomnia associated with alcohol cessation, or any combination thereof.

17. The method of claim 16, wherein administration of the compound of Formula (1) or a pharmaceutically acceptable salt thereof is by at least one route selected from oral, parenteral, intravenous, intramuscular, buccal, gingival, sublingual, intraocular, transdermal, and transmucosal.

18. The method of claim 17, wherein administration of the compound of Formula (1) or a pharmaceutically acceptable salt thereof is by oral, sublingual, gingival, or buccal administration.

19. The method of claim 14, wherein said administration is a single daily human dose of the compound of Formula (1) or a pharmaceutically acceptable salt thereof from about 0.10 mg to about 15 mg.

20. The method of claim 19, wherein the single daily human dose of the compound of Formula (1) or a pharmaceutically acceptable salt thereof is from about 0.2 mg to about 6.0 mg.

* * * * *